United States Patent
Krupat et al.

(10) Patent No.: US 10,401,860 B2
(45) Date of Patent: Sep. 3, 2019

(54) IMAGE ANALYSIS FOR TWO-SIDED DATA HUB

(71) Applicant: Affectiva, Inc., Boston, MA (US)

(72) Inventors: Jason Krupat, Needham, MA (US); Rana el Kaliouby, Milton, MA (US); Jason Radice, Sharon, NH (US); Gabriele Zijderveld, Somerville, MA (US); Chilton Lyons Cabot, Dedham, MA (US)

(73) Assignee: Affectiva, Inc., Boston, MA (US)

(*) Notice: Subject to any disclaimer, the term of this patent is extended or adjusted under 35 U.S.C. 154(b) by 0 days.

(21) Appl. No.: 15/918,122

(22) Filed: Mar. 12, 2018

(65) Prior Publication Data
US 2018/0196432 A1     Jul. 12, 2018

Related U.S. Application Data

(63) Continuation-in-part of application No. 15/886,275, filed on Feb. 1, 2018, which is a continuation of
(Continued)

(51) Int. Cl.
*A61B 5/00*     (2006.01)
*A61B 5/16*     (2006.01)
(Continued)

(52) U.S. Cl.
CPC ......... *G05D 1/0088* (2013.01); *A61B 5/0013* (2013.01); *A61B 5/0077* (2013.01);
(Continued)

(58) Field of Classification Search
CPC ........... G06K 9/00275; G06K 9/00281; G06K 9/0028; G06K 9/00295; G06K 9/00302;
(Continued)

(56) References Cited

U.S. PATENT DOCUMENTS 3,034,500 A    5/1962   Backster, Jr.
3,548,806 A   12/1970   Fisher
(Continued)

FOREIGN PATENT DOCUMENTS

JP           08115367       7/1996
KR   10-2005-0021759 A    3/2005
(Continued)

OTHER PUBLICATIONS

Rana Ayman El Kaliouby, Mind-reading machines: automated inference of complex mental states, Jul. 2005, University of Cambridge, Cambridge, United Kingdom.
(Continued)

*Primary Examiner* — Wesley J Tucker
(74) *Attorney, Agent, or Firm* — Adams Intellex, PLC

(57) ABSTRACT

Image analysis is performed for a two-sided data hub. Data reception on a first computing device is enabled by an individual and a content provider. Cognitive state data including facial data on the individual is collected on a second computing device. The cognitive state data is analyzed on a third computing device and the analysis is provided to the individual. The cognitive state data is evaluated and the evaluation is provided to the content provider. A mood dashboard is displayed to the individual based on the analyzing. The individual opts in to enable data reception for the individual. The content provider provides content via a website.

17 Claims, 20 Drawing Sheets

Related U.S. Application Data application No. 15/875,644, filed on Jan. 19, 2018, which is a continuation-in-part of application No. 15/273,765, filed on Sep. 23, 2016, which is a continuation-in-part of application No. 14/796,419, filed on Jul. 10, 2015, now abandoned, which is a continuation-in-part of application No. 14/460,915, filed on Aug. 15, 2014, which is a continuation-in-part of application No. 13/153,745, filed on Jun. 6, 2011, now abandoned, said application No. 15/886,275 is a continuation-in-part of application No. 14/144,413, filed on Dec. 30, 2013, now Pat. No. 9,934,425, which is a continuation of application No. 14/064,136, filed on Oct. 26, 2013, now Pat. No. 9,204,836, which is a continuation-in-part of application No. 13/153,745, filed on Jun. 6, 2011, now abandoned.

(60) Provisional application No. 62/637,567, filed on Mar. 2, 2018, provisional application No. 62/611,780, filed on Dec. 29, 2017, provisional application No. 62/593,440, filed on Dec. 1, 2017, provisional application No. 62/593,449, filed on Dec. 1, 2017, provisional application No. 62/557,460, filed on Sep. 12, 2017, provisional application No. 62/541,847, filed on Aug. 7, 2017, provisional application No. 62/524,606, filed on Jun. 25, 2017, provisional application No. 62/503,485, filed on May 9, 2017, provisional application No. 62/469,591, filed on Mar. 10, 2017, provisional application No. 62/448,448, filed on Jan. 20, 2017, provisional application No. 62/370,421, filed on Aug. 3, 2016, provisional application No. 62/301,558, filed on Feb. 29, 2016, provisional application No. 62/273,896, filed on Dec. 31, 2015, provisional application No. 62/265,937, filed on Dec. 10, 2015, provisional application No. 62/222,518, filed on Sep. 23, 2015, provisional application No. 62/128,974, filed on Mar. 5, 2015, provisional application No. 62/082,579, filed on Nov. 20, 2014, provisional application No. 62/047,508, filed on Sep. 8, 2014, provisional application No. 62/023,800, filed on Jul. 11, 2014, provisional application No. 61/972,314, filed on Mar. 30, 2014, provisional application No. 61/953,878, filed on Mar. 16, 2014, provisional application No. 61/927,481, filed on Jan. 15, 2014, provisional application No. 61/924,252, filed on Jan. 7, 2014, provisional application No. 61/916,190, filed on Dec. 14, 2013, provisional application No. 61/867,007, filed on Aug. 16, 2013, provisional application No. 61/467,209, filed on Mar. 24, 2011, provisional application No. 61/447,464, filed on Feb. 28, 2011, provisional application No. 61/447,089, filed on Feb. 27, 2011, provisional application No. 61/439,913, filed on Feb. 6, 2011, provisional application No. 61/414,451, filed on Nov. 17, 2010, provisional application No. 61/388,002, filed on Sep. 30, 2010, provisional application No. 61/352,166, filed on Jun. 7, 2010, provisional application No. 61/844,478, filed on Jul. 10, 2013, provisional application No. 61/789,038, filed on Mar. 15, 2013, provisional application No. 61/790,461, filed on Mar. 15, 2013, provisional application No. 61/793,761, filed on Mar. 15, 2013, provisional application No. 61/798,731, filed on Mar. 15, 2013, provisional application No. 61/747,651, filed on Dec. 31, 2012, provisional application No. 61/747,810, filed on Dec. 31, 2012, provisional application No. 61/719,383, filed on Oct. 27, 2012, provisional application No. 62/625,274, filed on Feb. 1, 2018.

(51) Int. Cl.

| | | |
|---|---|---|
| *A61B 5/18* | (2006.01) | |
| *G05D 1/00* | (2006.01) | |
| *G05D 1/02* | (2006.01) | |
| *G06K 9/00* | (2006.01) | |
| *G06K 9/46* | (2006.01) | |
| *G06K 9/62* | (2006.01) | |
| *G10L 15/18* | (2013.01) | |
| *G10L 15/22* | (2006.01) | |
| *G10L 25/63* | (2013.01) | |
| *G10L 25/90* | (2013.01) | |
| *A61B 5/1171* | (2016.01) | |
| *G08G 1/0962* | (2006.01) | |

(52) U.S. Cl.
CPC ............ *A61B 5/1176* (2013.01); *A61B 5/165* (2013.01); *A61B 5/18* (2013.01); *A61B 5/4803* (2013.01); *A61B 5/6893* (2013.01); *G05D 1/0221* (2013.01); *G05D 1/0291* (2013.01); *G06K 9/00302* (2013.01); *G06K 9/00845* (2013.01); *G06K 9/4652* (2013.01); *G06K 9/6255* (2013.01); *G06K 9/6269* (2013.01); *G08G 1/0962* (2013.01); *G10L 15/1815* (2013.01); *G10L 15/22* (2013.01); *G10L 25/63* (2013.01); *A61B 2576/02* (2013.01); *G10L 15/1807* (2013.01); *G10L 25/90* (2013.01)

(58) Field of Classification Search
CPC ........... G06K 9/00308; G06K 9/00315; G06K 9/00335; G06K 9/00342; G06K 9/00348; G06K 9/00355; G06K 9/00362; G06K 9/00241; G06K 9/00845; G05D 1/0088; G05D 1/0291; G10L 25/63; A61B 5/18; A61B 5/1176; A61B 5/4803; A61B 5/165; G08G 1/0962
See application file for complete search history.

(56) References Cited

U.S. PATENT DOCUMENTS

| | | |
|---|---|---|
| 3,870,034 A | 3/1975 | James |
| 4,353,375 A | 10/1982 | Colburn et al. |
| 4,448,203 A | 5/1984 | Williamson et al. |
| 4,794,533 A | 12/1988 | Cohen |
| 4,807,642 A | 2/1989 | Brown |
| 4,817,628 A | 4/1989 | Zealear et al. |
| 4,950,069 A | 8/1990 | Hutchinson |
| 4,964,411 A | 10/1990 | Johnson et al. |
| 5,016,282 A | 5/1991 | Tomono et al. |
| 5,031,228 A | 7/1991 | Lu |
| 5,219,322 A | 6/1993 | Weathers |
| 5,247,938 A | 9/1993 | Silverstein et al. |
| 5,259,390 A | 11/1993 | Maclean |
| 5,507,291 A | 4/1996 | Stirbl et al. |
| 5,572,596 A | 11/1996 | Wildes et al. |
| 5,619,571 A | 4/1997 | Sandstorm et al. |
| 5,647,834 A | 7/1997 | Ron |
| 5,649,061 A | 7/1997 | Smyth |
| 5,663,900 A | 9/1997 | Bhandari et al. |
| 5,666,215 A | 9/1997 | Fredlund et al. |
| 5,725,472 A | 3/1998 | Weathers |
| 5,741,217 A | 4/1998 | Gero |
| 5,760,917 A | 6/1998 | Sheridan |
| 5,762,611 A | 6/1998 | Lewis et al. |
| 5,772,508 A | 6/1998 | Sugita et al. |
| 5,772,591 A | 6/1998 | Cram |

(56) References Cited

U.S. PATENT DOCUMENTS

| | | |
|---|---|---|
| 5,774,591 A | 6/1998 | Black et al. |
| 5,802,220 A | 9/1998 | Black et al. |
| 5,825,355 A | 10/1998 | Palmer et al. |
| 5,886,683 A | 3/1999 | Tognazzini et al. |
| 5,898,423 A | 4/1999 | Tognazzini et al. |
| 5,920,477 A | 7/1999 | Hoffberg et al. |
| 5,945,988 A | 8/1999 | Williams et al. |
| 5,959,621 A | 9/1999 | Nawaz et al. |
| 5,969,755 A | 10/1999 | Courtney |
| 5,983,129 A | 11/1999 | Cowan et al. |
| 5,987,415 A | 11/1999 | Breese et al. |
| 6,004,061 A | 12/1999 | Manico et al. |
| 6,004,312 A | 12/1999 | Finneran et al. |
| 6,008,817 A | 12/1999 | Gilmore, Jr. |
| 6,026,321 A | 2/2000 | Miyata et al. |
| 6,026,322 A | 2/2000 | Korenman et al. |
| 6,056,781 A | 5/2000 | Wassick et al. |
| 6,067,565 A | 5/2000 | Horvitz |
| 6,088,040 A | 7/2000 | Oda et al. |
| 6,099,319 A | 8/2000 | Zaltman et al. |
| 6,134,644 A | 10/2000 | Mayuzumi et al. |
| 6,182,098 B1 | 1/2001 | Selker |
| 6,185,534 B1 | 2/2001 | Breese et al. |
| 6,195,651 B1 | 2/2001 | Handel et al. |
| 6,212,502 B1 | 4/2001 | Ball et al. |
| 6,222,607 B1 | 4/2001 | Szajewski et al. |
| 6,309,342 B1 | 10/2001 | Blazey et al. |
| 6,327,580 B1 | 12/2001 | Pierce et al. |
| 6,349,290 B1 | 2/2002 | Horowitz et al. |
| 6,351,273 B1 | 2/2002 | Lemelson et al. |
| 6,437,758 B1 | 8/2002 | Nielsen et al. |
| 6,443,840 B2 | 9/2002 | Von Kohorn |
| 6,530,082 B1 | 3/2003 | Del Sesto et al. |
| 6,577,329 B1 | 6/2003 | Flickner et al. |
| 6,606,102 B1 | 8/2003 | Odom |
| 6,629,104 B1 | 9/2003 | Parulski et al. |
| 6,792,458 B1 | 9/2004 | Muret et al. |
| 6,847,376 B2 | 1/2005 | Engeldrum et al. |
| 7,003,135 B2 | 2/2006 | Hsieh et al. |
| 7,013,478 B1 | 3/2006 | Hendricks et al. |
| 7,027,621 B1 * | 4/2006 | Prokoski ............ G06K 9/00248 180/272 |
| 7,113,916 B1 | 9/2006 | Hill |
| 7,120,880 B1 | 10/2006 | Dryer et al. |
| 7,197,459 B1 | 3/2007 | Harinarayan et al. |
| 7,233,684 B2 | 6/2007 | Fedorovskaya et al. |
| 7,246,081 B2 | 7/2007 | Hill |
| 7,263,474 B2 | 8/2007 | Fables et al. |
| 7,266,582 B2 | 9/2007 | Stelting |
| 7,307,636 B2 | 12/2007 | Matraszek et al. |
| 7,319,779 B1 | 1/2008 | Mummareddy et al. |
| 7,327,505 B2 | 2/2008 | Fedorovskaya et al. |
| 7,350,138 B1 | 3/2008 | Swaminathan et al. |
| 7,353,399 B2 | 4/2008 | Ooi et al. |
| 7,355,627 B2 | 4/2008 | Yamazaki et al. |
| 7,428,318 B1 | 9/2008 | Madsen et al. |
| 7,474,801 B2 | 1/2009 | Teo et al. |
| 7,496,622 B2 | 2/2009 | Brown et al. |
| 7,549,161 B2 | 6/2009 | Poo et al. |
| 7,551,755 B1 | 6/2009 | Steinberg et al. |
| 7,555,148 B1 | 6/2009 | Steinberg et al. |
| 7,558,408 B1 | 7/2009 | Steinberg et al. |
| 7,564,994 B1 | 7/2009 | Steinberg et al. |
| 7,573,439 B2 | 8/2009 | Lau et al. |
| 7,580,512 B2 | 8/2009 | Batni et al. |
| 7,584,435 B2 | 9/2009 | Bailey et al. |
| 7,587,068 B1 | 9/2009 | Steinberg et al. |
| 7,610,289 B2 | 10/2009 | Muret et al. |
| 7,620,934 B2 | 11/2009 | Falter et al. |
| 7,644,375 B1 | 1/2010 | Anderson et al. |
| 7,676,574 B2 | 3/2010 | Glommen et al. |
| 7,757,171 B1 | 7/2010 | Wong et al. |
| 7,826,657 B2 | 11/2010 | Zhang et al. |
| 7,830,570 B2 | 11/2010 | Morita et al. |
| 7,881,493 B1 | 2/2011 | Edwards et al. |
| 7,921,036 B1 | 4/2011 | Sharma |
| 8,010,458 B2 | 8/2011 | Galbreath et al. |
| 8,401,248 B1 | 3/2013 | Moon et al. |
| 8,442,638 B2 | 5/2013 | Libbus et al. |
| 8,522,779 B2 | 9/2013 | Lee et al. |
| 8,600,120 B2 | 12/2013 | Gonion et al. |
| 8,640,021 B2 | 1/2014 | Perez et al. |
| 9,466,161 B2 * | 10/2016 | Ricci ........................ H04W 4/21 |
| 2001/0033286 A1 | 10/2001 | Stokes et al. |
| 2001/0041021 A1 | 11/2001 | Boyle et al. |
| 2002/0007249 A1 | 1/2002 | Cranley |
| 2002/0030665 A1 | 3/2002 | Ano |
| 2002/0042557 A1 | 4/2002 | Bensen et al. |
| 2002/0054174 A1 | 5/2002 | Abbott et al. |
| 2002/0084902 A1 | 7/2002 | Zadrozny et al. |
| 2002/0171551 A1 | 11/2002 | Eshelman |
| 2002/0182574 A1 | 12/2002 | Freer |
| 2003/0035567 A1 | 2/2003 | Chang et al. |
| 2003/0037041 A1 | 2/2003 | Hertz |
| 2003/0060728 A1 | 3/2003 | Mandigo |
| 2003/0093784 A1 * | 5/2003 | Dimitrova .............. H04N 7/163 725/10 |
| 2003/0191682 A1 | 10/2003 | Shepard et al. |
| 2003/0191816 A1 | 10/2003 | Landress et al. |
| 2004/0181457 A1 | 9/2004 | Biebesheimer |
| 2005/0187437 A1 | 8/2005 | Matsugu |
| 2005/0283055 A1 | 12/2005 | Shirai et al. |
| 2005/0289582 A1 | 12/2005 | Tavares et al. |
| 2006/0011399 A1 * | 1/2006 | Brockway ................ A61B 5/18 180/272 |
| 2006/0019224 A1 | 1/2006 | Behar et al. |
| 2006/0143647 A1 | 6/2006 | Bill |
| 2006/0235753 A1 | 10/2006 | Kameyama |
| 2007/0167689 A1 | 7/2007 | Ramadas et al. |
| 2007/0239787 A1 | 10/2007 | Cunningham et al. |
| 2007/0255831 A1 | 11/2007 | Hayashi et al. |
| 2007/0265507 A1 | 11/2007 | de Lemos |
| 2007/0299964 A1 | 12/2007 | Wong et al. |
| 2008/0059570 A1 | 3/2008 | Bill |
| 2008/0091512 A1 | 4/2008 | Marci et al. |
| 2008/0091515 A1 | 4/2008 | Thieberger et al. |
| 2008/0101660 A1 | 5/2008 | Seo |
| 2008/0103784 A1 | 5/2008 | Wong et al. |
| 2008/0184170 A1 | 7/2008 | Periyalwar |
| 2008/0208015 A1 | 8/2008 | Morris et al. |
| 2008/0221472 A1 | 9/2008 | Lee et al. |
| 2008/0287821 A1 | 11/2008 | Jung et al. |
| 2008/0292151 A1 | 11/2008 | Kurtz et al. |
| 2009/0002178 A1 | 1/2009 | Guday et al. |
| 2009/0006206 A1 | 1/2009 | Groe |
| 2009/0083421 A1 | 3/2009 | Glommen et al. |
| 2009/0094286 A1 | 4/2009 | Lee et al. |
| 2009/0112694 A1 | 4/2009 | Jung et al. |
| 2009/0112810 A1 | 4/2009 | Jung et al. |
| 2009/0133048 A1 | 5/2009 | Gibbs et al. |
| 2009/0150919 A1 | 6/2009 | Lee et al. |
| 2009/0156907 A1 | 6/2009 | Jung et al. |
| 2009/0210290 A1 | 8/2009 | Elliott et al. |
| 2009/0217315 A1 * | 8/2009 | Malik ................ G06K 9/00362 725/9 |
| 2009/0259518 A1 | 10/2009 | Harvey |
| 2009/0270170 A1 | 10/2009 | Patton |
| 2009/0271417 A1 | 10/2009 | Toebes et al. |
| 2009/0292528 A1 * | 11/2009 | Kameyama .......... G08G 1/0962 704/9 |
| 2009/0299840 A1 | 12/2009 | Smith |
| 2010/0070523 A1 | 3/2010 | Delgo et al. |
| 2010/0099955 A1 | 4/2010 | Thomas et al. |
| 2010/0266213 A1 | 10/2010 | Hill |
| 2010/0274847 A1 | 10/2010 | Anderson et al. |
| 2010/0324437 A1 | 12/2010 | Freeman |
| 2011/0126226 A1 | 5/2011 | Makhlouf |
| 2011/0134026 A1 | 6/2011 | Kang et al. |
| 2011/0143728 A1 | 6/2011 | Holopainen et al. |
| 2011/0144971 A1 | 6/2011 | Danielson |
| 2011/0196855 A1 | 8/2011 | Wable et al. |
| 2011/0231240 A1 | 9/2011 | Schoen et al. |
| 2011/0251493 A1 | 10/2011 | Poh et al. |
| 2011/0263946 A1 | 10/2011 | el Kaliouby et al. |

(56) References Cited

U.S. PATENT DOCUMENTS

| | | |
|---|---|---|
| 2012/0324491 A1 | 12/2012 | Bathiche et al. |
| 2013/0023337 A1 | 1/2013 | Bowers et al. |
| 2013/0116587 A1 | 5/2013 | Sommo et al. |
| 2013/0197409 A1 | 8/2013 | Baxter et al. |
| 2016/0104486 A1* | 4/2016 | Penilla .................... H04L 67/12 704/232 |
| 2017/0021282 A1* | 1/2017 | Comploi ................ A63G 25/00 |
| 2019/0079540 A1* | 3/2019 | Yoon .................... G05D 1/0295 |

FOREIGN PATENT DOCUMENTS

| | | |
|---|---|---|
| KR | 10-2008-0016303 A | 2/2008 |
| KR | 1020100048688 A | 5/2010 |
| WO | WO 2011/045422 A1 | 4/2011 |

OTHER PUBLICATIONS

International Search Report dated Nov. 14, 2011 for PCT/US2011/39282.

International Search Report dated Apr. 16, 2012 for PCT/US2011/054125.

International Search Report dated May 24, 2012 for PCT/US2011/060900.

Xiaoyu Wang, An HOG-LBP human detector with partial occlusion handling, Sep. 29, 2009, IEEE 12th International Conference on Computer Vision, Kyoto, Japan.

Zhihong Zeng, A Survey of Affect Recognition Methods: Audio, Visual, and Spontaneous Expressions, Jan. 2009, IEEE Transactions on Pattern Analysis and Machine Intelligence, vol. 31, No. 1.

Nicholas R. Howe and Amanda Ricketson, Improving the Boosted Correlogram, 2004, Lecture Notes in Computer Science, ISSN 0302-9743, Springer-Verlag, Germany.

Xuming HE, et al, Learning and Incorporating Top-Down Cues in Image Segmentation, 2006, Lecture Notes in Computer Science, ISBN 978-3-540-33832-1, Springer-Verlag, Germany.

Ross Eaton, et al, Rapid Training of Image Classifiers through Adaptive, Multi-frame Sampling Methods, Oct. 2008, IEEE 37th Applied Imagery Pattern Recognition Workshop, Washington DC.

Verkruysse, Wim, Lars O. Svaasand, and J. Stuart Nelson. "Remote plethysmographic imaging using ambient light." Optics express 16.26 (2008): 21434-21445.

Albiol, Alberto, et al. "Face recognition using HOG-EBGM." Pattern Recognition Letters 29.10 (2008): 1537-1543.

* cited by examiner

IMAGE ANALYSIS FOR TWO-SIDED DATA HUB

RELATED APPLICATIONS

This application claims the benefit of U.S. provisional patent applications "Image Analysis for Two-sided Data Hub" Ser. No. 62/469,591, filed Mar. 10, 2017, "Vehicle Artificial Intelligence Evaluation of Mental States" Ser. No. 62/503,485, filed May 9, 2017, "Image Analysis for Emotional Metric Generation" Ser. No. 62/524,606, filed Jun. 25, 2017, "Image Analysis and Representation for Emotional Metric Threshold Evaluation" Ser. No. 62/541,847, filed Aug. 7, 2017, "Multimodal Machine Learning for Emotion Metrics" Ser. No. 62/557,460, filed Sep. 12, 2017, "Speech Analysis for Cross-Language Mental State Identification" Ser. No. 62/593,449, filed Dec. 1, 2017, "Avatar Image Animation Using Translation Vectors" Ser. No. 62/593,440, filed Dec. 1, 2017, "Directed Control Transfer for Autonomous Vehicles" Ser. No. 62/611,780, filed Dec. 29, 2017, "Cognitive State Vehicle Navigation Based on Image Processing" Ser. No. 62/625,274, filed Feb. 1, 2018, and "Cognitive State Based Vehicle Manipulation Using Near-Infrared Image Processing" Ser. No. 62/637,567, filed Mar. 2, 2018.

This application is also a continuation-in-part of U.S. patent application "Vehicular Cognitive Data Collection Using Multiple Devices" Ser. No. 15/886,275, filed Feb. 1, 2018, which claims the benefit of U.S. provisional patent applications "Image Analysis for Two-sided Data Hub" Ser. No. 62/469,591, filed Mar. 10, 2017, "Vehicle Artificial Intelligence Evaluation of Mental States" Ser. No. 62/503,485, filed May 9, 2017, "Image Analysis for Emotional Metric Generation" Ser. No. 62/524,606, filed Jun. 25, 2017, "Image Analysis and Representation for Emotional Metric Threshold Evaluation" Ser. No. 62/541,847, filed Aug. 7, 2017, "Multimodal Machine Learning for Emotion Metrics" Ser. No. 62/557,460, filed Sep. 12, 2017, "Speech Analysis for Cross-Language Mental State Identification" Ser. No. 62/593,449, filed Dec. 1, 2017, "Avatar Image Animation Using Translation Vectors" Ser. No. 62/593,440, filed Dec. 1, 2017, and "Directed Control Transfer for Autonomous Vehicles" Ser. No. 62/611,780, filed Dec. 29, 2017.

The patent application "Vehicular Cognitive Data Collection Using Multiple Devices" Ser. No. 15/886,275, filed Feb. 1, 2018 is also a continuation-in-part of U.S. patent application "Collection of Affect Data from Multiple Mobile Devices" Ser. No. 14/144,413, filed Dec. 30, 2013, which claims the benefit of U.S. provisional patent applications "Optimizing Media Based on Mental State Analysis" Ser. No. 61/747,651, filed Dec. 31, 2012, "Collection of Affect Data from Multiple Mobile Devices" Ser. No. 61/747,810, filed Dec. 31, 2012, "Mental State Analysis Using Heart Rate Collection Based on Video Imagery" Ser. No. 61/793,761, filed Mar. 15, 2013, "Mental State Data Tagging for Data Collected from Multiple Sources" Ser. No. 61/790,461, filed Mar. 15, 2013, "Mental State Analysis Using Blink Rate" Ser. No. 61/789,038, filed Mar. 15, 2013, "Mental State Well Being Monitoring" Ser. No. 61/798,731, filed Mar. 15, 2013, and "Personal Emotional Profile Generation" Ser. No. 61/844,478, filed Jul. 10, 2013.

The patent application "Collection of Affect Data from Multiple Mobile Devices" Ser. No. 14/144,413, filed Dec. 30, 2013 is also a continuation-in-part of U.S. patent application "Mental State Analysis Using Web Services" Ser. No. 13/153,745, filed Jun. 6, 2011, which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Data Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011.

The patent application "Collection of Affect Data from Multiple Mobile Devices" Ser. No. 14/144,413, filed Dec. 30, 2013 is also a continuation-in-part of U.S. patent application "Sporadic Collection of Mobile Affect Data" Ser. No. 14/064,136, filed Oct. 26, 2013, which claims the benefit of U.S. provisional patent applications "Sporadic Collection of Affect Data" Ser. No. 61/719,383, filed Oct. 27, 2012, "Optimizing Media Based on Mental State Analysis" Ser. No. 61/747,651, filed Dec. 31, 2012, "Collection of Affect Data from Multiple Mobile Devices" Ser. No. 61/747,810, filed Dec. 31, 2012, "Mental State Analysis Using Heart Rate Collection Based on Video Imagery" Ser. No. 61/793,761, filed Mar. 15, 2013, "Mental State Data Tagging for Data Collected from Multiple Sources" Ser. No. 61/790,461, filed Mar. 15, 2013, "Mental State Analysis Using Blink Rate" Ser. No. 61/789,038, filed Mar. 15, 2013, "Mental State Well Being Monitoring" Ser. No. 61/798,731, filed Mar. 15, 2013, and "Personal Emotional Profile Generation" Ser. No. 61/844,478, filed Jul. 10, 2013.

The patent application "Vehicular Cognitive Data Collection Using Multiple Devices" Ser. No. 15/886,275, filed Feb. 1, 2018 is also a continuation-in-part of U.S. patent application "Vehicle Manipulation using Occupant Image Analysis" Ser. No. 15/875,644, filed Jan. 19, 2018, which claims the benefit of U.S. provisional patent applications "Vehicle Manipulation using Occupant Image Analysis" Ser. No. 62/448,448, filed Jan. 20, 2017, "Image Analysis for Two-sided Data Hub" Ser. No. 62/469,591, filed Mar. 10, 2017, "Vehicle Artificial Intelligence Evaluation of Mental States" Ser. No. 62/503,485, filed May 9, 2017, "Image Analysis for Emotional Metric Generation" Ser. No. 62/524,606, filed Jun. 25, 2017, "Image Analysis and Representation for Emotional Metric Threshold Evaluation" Ser. No. 62/541,847, filed Aug. 7, 2017, "Multimodal Machine Learning for Emotion Metrics" Ser. No. 62/557,460, filed Sep. 12, 2017, "Speech Analysis for Cross-Language Mental State Identification" Ser. No. 62/593,449, filed Dec. 1, 2017, "Avatar Image Animation Using Translation Vectors" Ser. No. 62/593,440, filed Dec. 1, 2017, and "Directed Control Transfer for Autonomous Vehicles" Ser. No. 62/611,780, filed Dec. 29, 2017.

The patent application "Vehicle Manipulation Using Occupant Image Analysis" Ser. No. 15/875,644, filed Jan. 19, 2018 is also a continuation-in-part of U.S. patent application "Image Analysis in Support of Robotic Manipulation" Ser. No. 15/273,765, filed Sep. 23, 2016, which claims the benefit of U.S. provisional patent applications "Image Analysis In Support of Robotic Manipulation" Ser. No. 62/222,518, filed Sep. 23, 2015, "Analysis of Image Content with Associated Manipulation of Expression Presentation" Ser. No. 62/265,937, filed Dec. 10, 2015, "Image Analysis Using Sub-Sectional Component Evaluation To Augment Classifier Usage" Ser. No. 62/273,896, filed Dec. 31, 2015, "Analytics for Live Streaming Based on Image Analysis within a Shared Digital Environment" Ser. No. 62/301,558, filed Feb. 29, 2016, and "Deep Convolutional Neural Network Analysis of Images for Mental States" Ser. No. 62/370,421, filed Aug. 3, 2016.

The patent application "Image Analysis in Support of Robotic Manipulation" Ser. No. 15/273,765, filed Sep. 23, 2016 is a continuation-in-part of U.S. patent application "Mental State Event Definition Generation" Ser. No. 14/796,419, filed Jul. 10, 2015 which claims the benefit of U.S. provisional patent applications "Mental State Event Definition Generation" Ser. No. 62/023,800, filed Jul. 11, 2014, "Facial Tracking with Classifiers" Ser. No. 62/047,508, filed Sep. 8, 2014, "Semiconductor Based Mental State Analysis" Ser. No. 62/082,579, filed Nov. 20, 2014, and "Viewership Analysis Based On Facial Evaluation" Ser. No. 62/128,974, filed Mar. 5, 2015.

The patent application "Mental State Event Definition Generation" Ser. No. 14/796,419, filed Jul. 10, 2015 is also a continuation-in-part of U.S. patent application "Mental State Analysis Using Web Services" Ser. No. 13/153,745, filed Jun. 6, 2011, which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011.

The patent application "Mental State Event Definition Generation" Ser. No. 14/796,419, filed Jul. 10, 2015 is also a continuation-in-part of U.S. patent application "Mental State Analysis Using an Application Programming Interface" Ser. No. 14/460,915, Aug. 15, 2014, which claims the benefit of U.S. provisional patent applications "Application Programming Interface for Mental State Analysis" Ser. No. 61/867,007, filed Aug. 16, 2013, "Mental State Analysis Using an Application Programming Interface" Ser. No. 61/924,252, filed Jan. 7, 2014, "Heart Rate Variability Evaluation for Mental State Analysis" Ser. No. 61/916,190, filed Dec. 14, 2013, "Mental State Analysis for Norm Generation" Ser. No. 61/927,481, filed Jan. 15, 2014, "Expression Analysis in Response to Mental State Express Request" Ser. No. 61/953,878, filed Mar. 16, 2014, "Background Analysis of Mental State Expressions" Ser. No. 61/972,314, filed Mar. 30, 2014, and "Mental State Event Definition Generation" Ser. No. 62/023,800, filed Jul. 11, 2014.

The patent application "Mental State Analysis Using an Application Programming Interface" Ser. No. 14/460,915, Aug. 15, 2014 is also a continuation-in-part of U.S. patent application "Mental State Analysis Using Web Services" Ser. No. 13/153,745, filed Jun. 6, 2011, which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011.

Each of the foregoing applications is hereby incorporated by reference in its entirety.

FIELD OF INVENTION

This application relates generally to image analysis and more particularly to image analysis for a two-sided hub.

BACKGROUND

People spend remarkable amounts of time engaging with the internet. While some of that time is spent on productive, informational, or educational pursuits, other amounts—sometimes vast amounts—of time are spent viewing, interacting with, or "surfing" for web content found on various web pages. The webpages, and the websites that host the webpages, contain a wide variety of content with which the people choose to engage. The content includes news, shopping, sports, politics, cute puppy videos, and much, much more. Website analytics, commonly called simply "web analytics", are performed to collect, measure, analyze, and report useful information related to a given website. The website information is analyzed in order to understand how people use the website and how to optimize the manner in which the website is used. Website analytics have been performed by analyzing the amount of time a person spends on a webpage, and the path through the internet that the person has taken to reach the webpage. Web analytics are often used by the enterprises that manage the websites, as well as by various market research groups, to measure how effectively the websites are performing for them. So, whether the enterprise is launching a new product, or the marketing research group is testing their advertising campaign, web analytics are used to determine website engagement and effectiveness.

Web analytics typically derive from a few basic actions. These actions include collecting and processing of data, developing key performance indicators (KPI), and formulating an online strategy. The online strategy is intended to further the goals of the website owner, whether those goals are to increase sales, to better provide important information, or to increase clicks on those cute puppy videos. Based on the results of these actions, enterprises can move forward with website improvement, and the advertising groups can boost their campaign performance.

The evaluation of the cognitive states of individuals who are visiting a webpage is key to understanding the individuals. The evaluation is also key to understanding the ways in which those individuals react to the world around them. Cognitive states run the gamut from happiness to sadness, from contentedness to worry, from excitement to calmness, from boredom to attentiveness, among numerous others. These cognitive states are experienced in response to everyday events such as frustration which stuck a traffic jam, boredom while waiting in line, impatience while waiting for that first cup of coffee, and even as people interact with their computers and the internet. Individuals perceive and empathize with other people by consciously or unconsciously evaluating and understanding the cognitive states of those other people. For example, an empathetic person may perceive in another person anxiety or joy and may respond accordingly. The ability and means by which one person perceives the emotional state of another is often quite difficult to summarize and has often been communicated as visceral or as a "gut feel." Yet, automated evaluation of the cognitive states of people is far more challenging.

Cognitive states, such as confusion, concentration, and worry, may be identified to aid in the understanding of an individual or group of people. People can collectively respond with fear or anxiety, such as after witnessing a catastrophe. Similarly, people can collectively respond with happy enthusiasm, such as when their sports team obtains a victory. Certain facial expressions and head gestures may be used as cues to identify a cognitive state that a person is experiencing. Limited automation has been performed in the evaluation of cognitive states based on facial expressions. Certain physiological conditions may provide telling indications of a person's state of mind and have been evaluated in a crude fashion, as with an apparatus used for lie detection or polygraph tests.

SUMMARY

Image analysis is used for a two-sided data hub. The two-sided data hub, which can include a cognitive reaction data hub, can be part of a two-sided marketplace. A two-sided marketplace can connect individuals seeking content with providers who can deliver the content. Data reception is enabled on a first computing device by both an individual and a content provider. The enabling can be accomplished using the cognitive reaction data hub. Cognitive state data including facial data of the individual is collected on a second computing device. The collecting cognitive state data including facial data on the individual can be accomplished using a webcam. The webcam can be integrated into a device displaying content from the content provider, or the webcam can be included in a device different from the device displaying content from the content provider. A third computing device is used to analyze the cognitive state data including facial data on the individual. The third computing device for analysis can include the collecting computing device, a server, a remote server, a cloud-based server, and so on. The cognitive state data is evaluated for providing information to the content provider. The evaluating can include generating a cognitive profile, and the cognitive profile can be used on the cognitive reaction data hub. The evaluating can further include aggregating the cognitive state data from the individual with cognitive state data from other individuals. The cognitive state data from other individuals can be based on demographics, and the cognitive state data from other individuals based on demographics can be used to provide a worldwide cognitive state map. The evaluating the cognitive state data can further include using a temporal signature for the cognitive state data. The evaluating can be used to enable the content provider to analyze cognitive engagement. The evaluating can be augmented using audio data from the individual.

In embodiments, a computer program product is embodied in a non-transitory computer readable medium for image analysis, the computer program product comprising code which causes one or more processors to perform operations of: enabling, on a first computing device, data reception by an individual and a content provider; collecting, on a second computing device, cognitive state data including facial data on the individual; analyzing, on a third computing device, the cognitive state data for providing analysis of the cognitive state data to the individual; and evaluating the cognitive state data for providing evaluation of the cognitive state data to the content provider. In embodiments, a computer system for image analysis comprises: a memory which stores instructions; one or more processors attached to the memory wherein the one or more processors, when executing the instructions which are stored, are configured to: enable data reception by an individual and a content provider; collect cognitive state data including facial data on the individual; analyze the cognitive state data for providing analysis of the cognitive state data to the individual; and evaluate the cognitive state data for providing evaluation of the cognitive state data to the content provider.

In some embodiments, a computer-implemented method for image analysis comprises: enabling, on a first computing device, data reception by an individual and a content provider; collecting, on a second computing device, cognitive state data including facial data on the individual; analyzing, on a third computing device, the cognitive state data for providing analysis of the cognitive state data to the individual; and evaluating the cognitive state data for providing evaluation of the cognitive state data to the content provider.

Various features, aspects, and advantages of numerous embodiments will become more apparent from the following description.

BRIEF DESCRIPTION OF THE DRAWINGS

The following detailed description of certain embodiments may be understood by reference to the following figures wherein.

DETAILED DESCRIPTION

Figure 1:
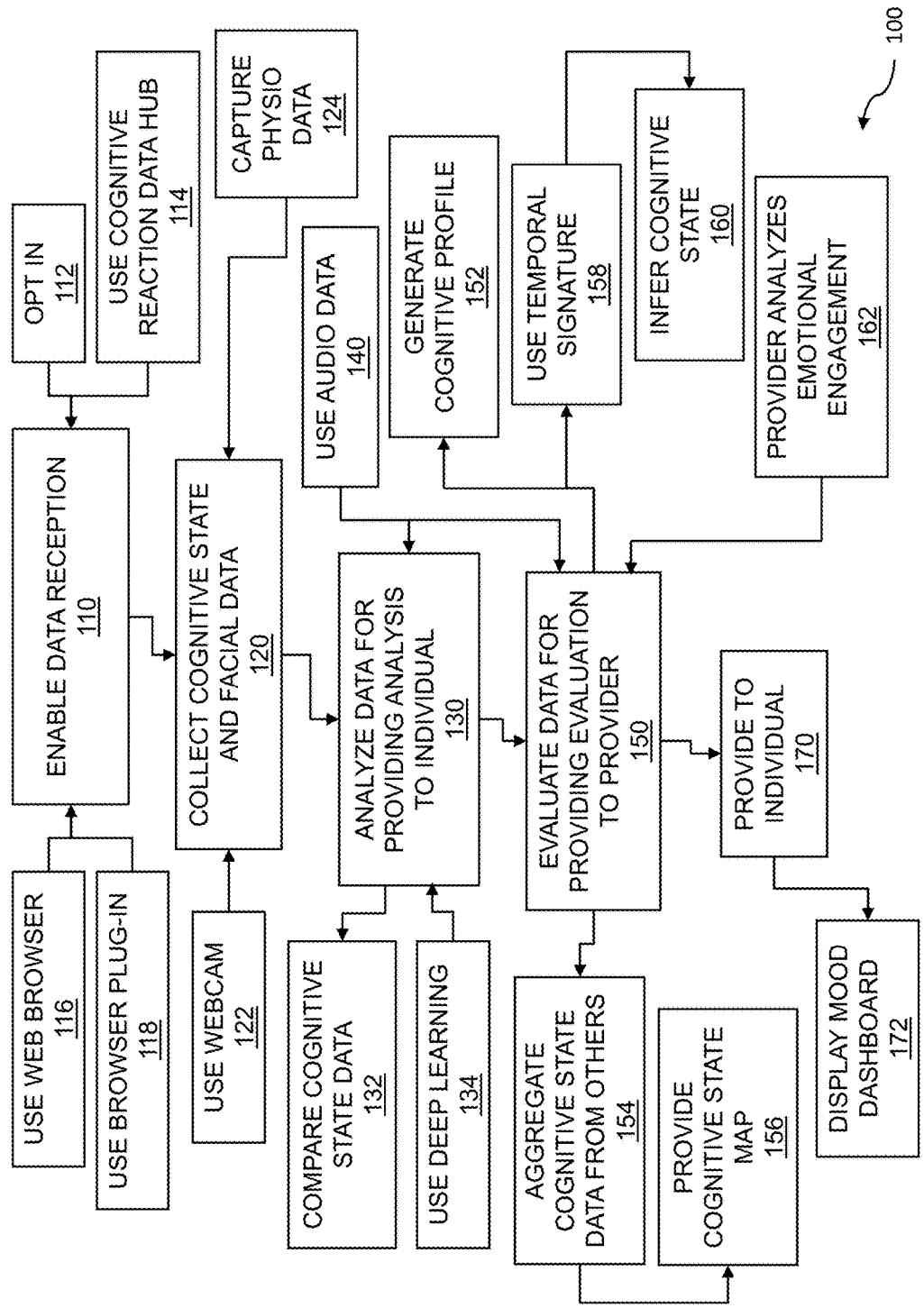
FIG. 1 is a flow diagram for image analysis for a two-sided hub.

Individuals interact with websites, streaming media, social media, and many other digital mediums. These content channels, which are supplied by content providers, induce cognitive states, emotional states, mental states, and moods in the individuals. The channels can inform, amuse, entertain, annoy, anger, bore, etc., those who view the channels. As a result, the cognitive states of a given individual can be directly influenced by their viewing the content provided by the content provider. From the perspective of the individual, she or he may want to find and view content that makes them happy, while skipping content they find to be boring, and avoiding content that irks, annoys, or angers them. The content that the individual views could be used to cheer up the individual, entertain or inform them, stir them to action, etc. From the perspective of the content provider, the content needs to effectively convey a particular message, where the message can inform, amuse, motivate, etc. The content provider is motivated to quantify the effectiveness of the delivery of the message. Ideally, the message effectively delivers the content to individuals of different ages, genders, races, and so on.

The cognitive state of an individual can be determined by capturing cognitive state data including facial data. By analyzing the facial data, the individual can be provided with analysis of her or his cognitive state. By evaluating the facial data of the individual, the content provider can be provided evaluation of the cognitive state of the individual. The individual can receive recommendations for channels such as websites, news feeds, streaming video, etc., that match the desired mood of the individual. The recommended channels can be used to help the individual attain goals such as numbers of smiles, reduced incidents of angry responses, and the like. The content provider can evaluate emotional engagement of the individual with the content provided by the content provider. A mutually beneficial arrangement can be attained, where the individual receives content that makes her or him happy, and the content provider receives benefits such as increased "face time" with the individual, increased mouse clicks, increased website traffic, an effectively delivered message, financial remuneration, and so on.

In disclosed techniques, image analysis is used for a two-sided data hub. Data reception is enabled on a first computing device by an individual and a content provider. In embodiments, the enabling can be accomplished using a web browser, where the user can fill in a web form, check a box, etc. In other embodiments, the enabling can be accomplished using a browser plug-in or browser extension (add-on), where the browser plug-in or extension can be a plug-in or extension appropriate to the web browser preferred by the individual (e.g. Chrome™ Edge™, Firefox™, Opera™, Safari™, etc.) Cognitive state data including facial data on the individual is collected on a second computing device. The cognitive state data and the facial data can be captured using a webcam, where the webcam can be integrated into a device displaying content from the content provider, or can be included in a device different from the device displaying content from the content provider, etc. The cognitive state data is analyzed on a third computing device and the results are provided to the individual. The computing device can include the device being used by the individual to observe content, another nearby device, a server, a remote server, a cloud-based server, and so on. In embodiments, augmenting the analyzing can be performed using audio data from the individual. The cognitive state data is evaluated and the results are provided to the content provider. As for the analyzing, augmenting the evaluating can use audio data from the individual. A mood dashboard can be displayed to the individual based on the analyzing. The mood dashboard can be displayed on an electronic device with which the individual is interacting.

FIG. 1 is a flow diagram for image analysis for a two-sided hub. Various disclosed techniques include image analysis for a two-sided data hub. The flow 100 includes enabling, on a first computing device, data reception 110 by an individual and a content provider. The individual can choose to enable reception of data such as web content, streaming media, social media, advertisements, political content, public service announcements, and so on. The content provider can enable data reception for data such as content requests from the individual, feedback from the individual, etc. The content provider can supply content to the individual via a website, a streaming site, a social media site, an app, etc. The enabling can include opting in 112 by the individual to the enabling data reception 110 by the individual. The opting in can be accomplished by an action deliberately taken by the individual as opposed to an inaction (opting in by default), where the deliberate action can include agreeing to opt in using an online form, a paper form, nodding assent toward a camera, etc. In embodiments, the enabling is accomplished using a cognitive reaction data hub 114. The cognitive reaction data hub can be used by the individual and by the content provider to transfer cognitive state data related to the individual. The cognitive reaction data hub can be part of a two-sided marketplace. The two-sided marketplace can include providing content from the content provider to the individual. The content can be selected by the individual and/or recommended by the content provider, etc., and can affect the mood, emotional state, mental state, cognitive state, etc., of the individual. In other embodiments, the enabling is accomplished using a web browser 116. The enabling can be accomplished by the individual filling in a web form, checking a box in a popup window, proceeding to a given website, and so on. In other embodiments, the enabling can be accomplished using a browser plug-in 118 or browser extension (add-on). The browser plug-in can be downloaded from an online store such as iTunes Store™, Google Play Store™, Chrome Web Store™, Add-ons for Firefox™, from a vendor website, from a content provider website, etc.

The flow 100 includes collecting, on a second computing device, cognitive state data including facial data 120 on the individual. The first computing device and the second computing device can be a common device. The common device can be a handheld electronic device as discussed, a local computer, a remote computer, a cloud computer, a mesh computer, etc. The individual can be outdoors, indoors, in a public space, in an office, in their home, and so on. In embodiments, the collecting of cognitive state data can be accomplished within a vehicle and the individual can be an occupant of the vehicle. The vehicle can be an automobile, a bus, a train, an airplane, a truck, a van, a sport utility vehicle (SUV), a motorcycle, a bicycle, a scooter, etc. In embodiments, the occupant can be a driver or operator of the vehicle. In other embodiments, the occupant can be a passenger. The collecting of cognitive state data and facial data can include using a video camera, a still camera, a thermal imager, a CCD device, a smartphone camera, a three-dimensional camera, a depth camera, a light field (plenoptic) camera, multiple cameras used to show different views of an individual, or any other type of image capture apparatus that can allow captured data to be used in an electronic system. In embodiments, the collecting cognitive state data, including facial data on the individual, is accomplished using a webcam 122. More than one webcam can be used. The webcam can be integrated into a device displaying content from the content provider, such as a smartphone, a personal digital assistant (PDA), a tablet computer, a laptop computer, etc. The webcam can be included in a different device from the device displaying content from the content provider. The webcam could be mounted in a room, coupled to a device with a view of the individual, and so on. The collecting cognitive state data further can further include capturing physiological data 124. The physiological data can include electrodermal activity (EDA)—also known as skin conductance (SC) or galvanic skin response (GSR), skin temperature, heart rate, heart rate variability, respiratory rate, and various other data.

The flow 100 includes analyzing, on a third computing device, the cognitive state data for providing the results to the individual 130. The second computing device and the third computing device can be a common device, such as a nearby computer for collecting cognitive state data, a remote computer, a cloud-based computer, etc. The analyzing the cognitive state data describes an emotional mood for the individual. The emotional mood of the individual can include happy, sad, bored, concentrating, confused, inattentive, angry, and so on. The analyzing can further include comparing the cognitive state data with collected cognitive state data from other individuals 132. The comparing can include determining whether the individual experienced a cognitive state, a mood, etc., similar to or different from the other individuals. The cognitive state data from other individuals can be based on demographics, where the demographics can include age, gender, race, geographic location, educational level, household income, etc. In embodiments, the analyzing is performed using deep learning 134. The deep learning can be based on a convolutional neural network (CNN), a deep neural network (DNN), and so on. The deep learning can adjust layers and weights to improve analysis for the individual.

The flow 100 includes augmenting the analyzing using audio data 140 from the individual. The audio data can include voice data. The audio data and the voice data can be collected using a microphone, a transducer, or other audio capture apparatus. The audio data can include noises and sounds made by the individual. In embodiments, the audio data can include non-speech vocalizations. The non-speech vocalizations can include grunts, yelps, squeals, snoring, sighs, laughter, filled pauses, unfilled pauses, or yawns. The collected facial data and the collected voice data can be for the individual, for more than one individual, etc. The voice data can be collected from the individual as the individual is interacting with a website, a social media site, or other content provided by the content provider. The collected audio data can include ambient room sounds, physiological sounds such as breathing or coughing, noises made by the individual such as tapping and drumming, and so on. The audio data and the voice data can be analyzed. The voice data can be evaluated for timbre, prosody, vocal register, vocal resonance, pitch, loudness, speech rate, or language content. The analyzing of the voice data can be used to determine one or more cognitive states. The augmenting the cognitive state data can be based on lexical analysis of the voice data that looks at sentiment. The lexical analysis can be based on converting voice data to text, and analyzing the text for keywords, key phrases, syntax, semantics, and so on. The lexical analysis of the voice data can look at sentiment of the individual. The flow can include using the audio data and the voice data for performing voice recognition for the individual. The voice recognition can be based on voice features, voice characteristics, etc. The voice recognition can be based on using classifiers. The classifiers can be uploaded by the content provider, downloaded from the Internet, and so on.

The flow 100 includes evaluating the cognitive state data and providing the results to the content provider 150. The evaluation of the cognitive state data can assist the content provider in determining whether the individual has understood the intended message of the content. The intended message can include a humorous advertisement message resulting in laughter from the individual, a serious message eliciting concentration from the individual, and so on. The evaluating can include augmenting the evaluating using audio data from the individual 140. The audio data includes voice data from the individual. The evaluating can include generating a cognitive profile 152. The cognitive profile can be a cognitive or emotion profile for the individual, an aggregated cognitive or emotion profile for a plurality of individuals, a cognitive profile for content provided by the content provider, etc. The cognitive profile can be used on the cognitive reaction data hub. The cognitive profile can be used to determine what material such as videos and images provided by the content provider can best emotionally connect with the individual. The evaluating can further include aggregating the cognitive state data 154 with cognitive state data from other individuals. The aggregating can be based on content, time, location, and so on. In embodiments, the aggregating can be based on time intervals. The time intervals can be periodic, based on times of day, at random times, etc. The cognitive state data from other individuals can be based on demographics, where the demographics can include age, gender, race, nationality, income level, educational level, content preferences, etc. The cognitive state data from other individuals based on demographics is used to provide a worldwide cognitive state map 156. The worldwide cognitive state map, or "hot spot" map, can be used to show cognitive states, cognitive states, emotional states, moods, etc., of individuals across towns, states, regions, countries, continents, and so on, including moods at a given time. The worldwide cognitive state map can be based on reactions to content.

The evaluating the cognitive state data can further include using a temporal signature 158 for the cognitive state data. The temporal signature can be tied to the content itself, delivery time of the content, cognitive states at the time of content delivery, and so on. The temporal signature can include an onset (e.g. rise time), a duration, a decay (e.g. a fall time), and so on. The temporal signature can be used to infer a cognitive state 160. The temporal signature can be based on detecting action units occurring at facial landmarks, in facial regions, etc. The evaluating can be used to enable the content provider to analyze emotional engagement 162. The emotional engagement analysis can determine whether the message being provided by the content provider is being understood by the individual, and if so, how well the message is being received. A well-received message can elicit desired moods and reactions, mouse clicks, website visits, click through actions, etc. The flow 100 includes the results of the evaluating of the cognitive state data being provided to the individual 170. The results can include statistics, websites visited and content consumed, durations of content consumption, selfies, emoji, and so on. The results of the evaluating can be provided by a website, a data stream, etc. The flow 100 includes displaying a mood dashboard 172 to the individual based on the analyzing. The mood dashboard can be rendered on an electronic device with which the individual is interacting and on another electronic device coupled to a display. The mood dashboard can be displayed using a web browser, an app, and so on. The mood dashboard can include a variety of information that can be useful to the individual such as a mood score, a smile meter, an anger level, heart rate, a happy browser score, a frustration score, a breathing goal, an eye blinks goal, a content goal, etc. The mood dashboard can include activity levels such as browsing levels, recommendations for goals, and so on. Various steps in the flow 100 may be changed in order, repeated, omitted, or the like without departing from the disclosed concepts. Various embodiments of the flow 100 can be included in a computer program product embodied in a non-transitory computer readable medium that includes code executable by one or more processors.

Figure 2:
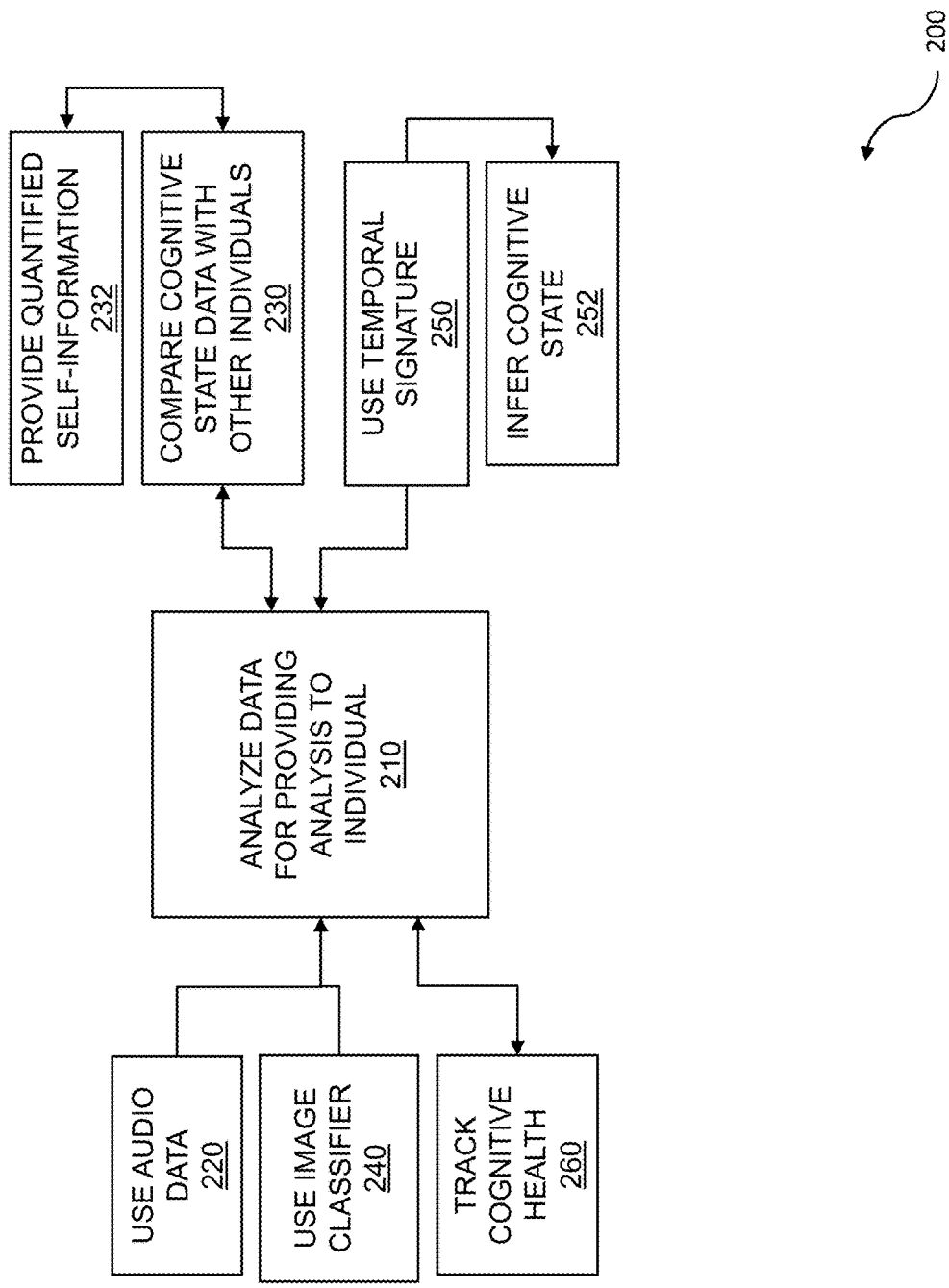
FIG. 2 is a flow diagram for analyzing data for providing to an individual.

FIG. 2 is a flow diagram for analyzing data and providing the analysis to an individual. Data analysis can include image analysis, where image analysis can support a two-sided data hub. The two-sided data hub can include a cognitive reaction data hub or other type of two-sided data hub. The cognitive reaction data hub can be part of a two-sided marketplace. Data reception is enabled by an individual and a content provider. Cognitive state data including facial data is collected on the individual. Other cognitive state may also be collected. Other cognitive state data can include audio data, voice data, speech data, non-speech vocalizations, physiological data, and so on. The cognitive state data can be collected for analysis and for evaluation. The flow 200 includes analyzing the cognitive state data and providing analysis of the cognitive state data to the individual 210. The analysis can include applying algorithms, heuristics, codes, and so on, to determine content of the facial data. The content of the facial data can include cognitive state content, emotional state content, mental state content, moods, and so on.

The flow 200 includes augmenting the analyzing using audio data 220 from the individual. The audio data can include audio from the individual and other audio. The other audio can include ambient audio from an open space, from a room, from beyond a vehicle, from within a vehicle, and so on. As mentioned before, the audio data can include voice data from the individual, speech data, non-speech vocalizations, etc. In embodiments, the non-speech vocalizations include grunts, yelps, squeals, snoring, sighs, laughter, filled pauses, unfilled pauses, or yawns. The flow 200 includes comparing the cognitive state data with collected cognitive state data from other individuals 230. The other individuals can include other individuals who have enabled data reception. The other individuals can represent a subset of a larger group of individuals, where the subset of individuals can have similar characteristics to the individual. The characteristics can be based on preferences, similar interests, adjacent locations, etc. The other individuals for comparison can be selected based on demographics such as age, gender, race, geographic location, educational level, household income, etc. In embodiments, the comparing can provide quantified self-information 232 on cognitive states for the individual. The quantified self-information can include total activity, number of steps taken, food eaten or calorie intake, amount of sleep, heart rate, cognitive states such as mood, etc. The quantified self-information can include a smile or other facial expression percentage, the number of times a smile or other facial expression occurred, the website or other content being observed by the individual, the time of the content viewing, the duration of content viewing, achievements of mood goals, and so on.

The flow 200 includes using an image classifier 240 from a plurality of image classifiers to detect emotional content within the facial data for the individual. The image classifier can be uploaded by a user, obtained from a library of image classifiers, downloaded over a computer network such as the Internet, and so on. The plurality of image classifiers can be used to detect one or more emotions (the emotional content) within the facial data. The emotions can include happy, sad, engaged, angry, bored, and the like. In the flow 200, the analyzing the cognitive state data can include using a temporal signature 250 for the cognitive state data. As stated elsewhere, the temporal signal can include a rise time, a duration, a decay time, and so on, of an event detected within the facial data. The event can include a smile, a frown, a smirk, an open mouth, etc. In embodiments, the flow 200 includes using the temporal signature to infer a cognitive state 252 such as those cognitive states described elsewhere (happy, sad, angry, bored, etc.). In the flow 200, the analyzing the cognitive state data is used to enable the individual to track cognitive health 260. The tracking of the cognitive health of the individual can be based on metrics such as the number of smiles, frowns, scowls, smirks, etc., that can occur during a period of time such as an hour, a day, a week, a month, and the like. The tracking the cognitive health of the individual can be based on attaining goals. The goals can be set by the individual, by a counselor, by an advisor, by a doctor, etc. Various steps in the flow 200 may be changed in order, repeated, omitted, or the like without departing from the disclosed concepts. Various embodiments of the flow 200 can be included in a computer program product embodied in a non-transitory computer readable medium that includes code executable by one or more processors.

Figure 3:
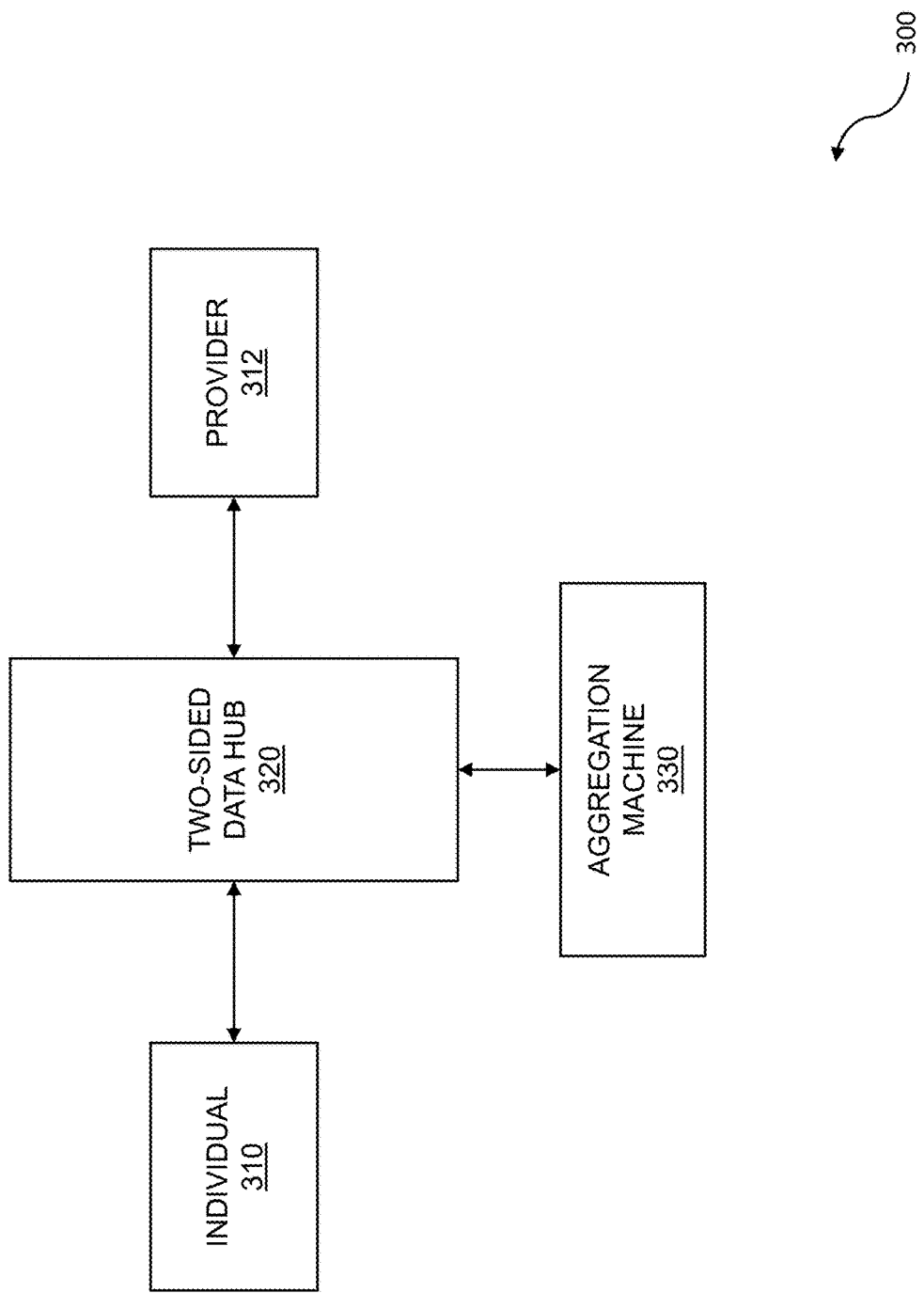
FIG. 3 illustrates a system for image analysis.

FIG. 3 illustrates a system for image analysis. Image analysis can be performed for a two-sided data hub. The image analysis includes enabling data reception by an individual and a content provider. The enabling can be accomplished using a cognitive reaction data hub. The individual can receive content from the content provider through a web browser, web browser plug-in, or other technique. Cognitive state data including facial data is collected on an individual. The collecting cognitive state data including facial data on the individual can be accomplished using a webcam, where the webcam can be integrated into a device displaying content from the content provider, or the webcam can be included in a device different from the device displaying content from the content provider. One or more processors are used to analyze the cognitive state data for providing analysis of the cognitive state data to the individual. The analysis can take place on the image capture device, a server, a remote server, a cloud-based service, and so on. The cognitive state data is evaluated for providing evaluation of the cognitive state data to the content provider. The system for image analysis 300 includes a two-sided data hub 320. The two-sided data hub can be enabled by an individual 310 and a content provider 312. The data hub can be a two-sided cognitive reaction data hub. The data hub can be part of a two-sided marketplace. The two-sided data hub 320 can interact with the individual 310 who has enabled the data reception. The enabling can be accomplished using a web browser. The enabling can be accomplished using a browser plug-in, a browser extension, a browser add-on, an opt-in form, a check box, and so on. The individual 310 can receive content from the content provider 312. The content provider can provide content via a website. The content can include web pages, videos, images, news articles, and so on. The system for image analysis includes an aggregation machine 330. The aggregation machine 330 can analyze data collected from an individual and/or a plurality of individuals. The analyzing can include using an image classifier from a plurality of image classifiers to detect emotional content within the facial data for the individual. Other analysis or evaluation techniques can be used to detect emotional content with the facial data for the individual.

The aggregation machine 330 can evaluate cognitive state data and other data collected from the individual and from the plurality of individuals. The evaluating can be used to enable the content provider to analyze emotional engagement. In embodiments, the evaluating the cognitive state data can further include using a temporal signature for the cognitive state data. The temporal signature can include a rise time, a duration, a decay time, and so on. The temporal signal can be associated with a facial expression, an intensity of a facial expression, etc. Further embodiments can include using the temporal signature to infer a cognitive state. The cognitive state data can be indicative of a variety of cognitive, mental, emotional, or other states. In embodiments, the cognitive state data can be indicative of drowsiness, fatigue, distraction, impairment, sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, depression, envy, sympathy, embarrassment, poignancy, or mirth. The evaluating can include aggregating the cognitive state data with cognitive state data from other individuals. The aggregating can be based on moods, emotions, cognitive states, and so on. The cognitive state data from other individuals can be based on demographics such as age, gender, race, ethnicity, geographic location, educational level, household income, etc.

Figure 4:
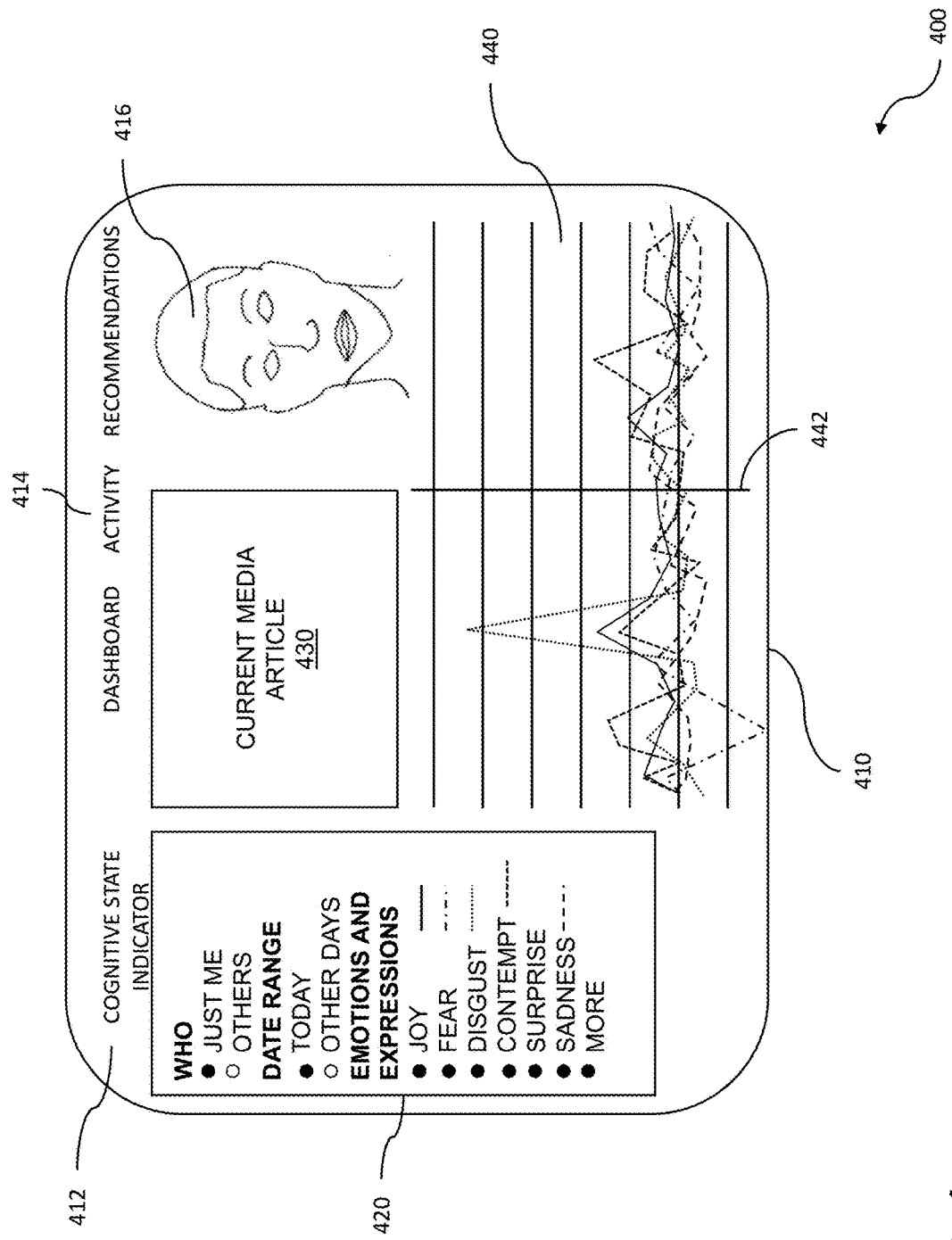
FIG. 4 shows an example dashboard for individual activity.

FIG. 4 shows an example dashboard 400 for individual activity. A dashboard for individual activity can be based on image analysis for a two-sided data hub. The data hub can be a cognitive reaction data hub, where the cognitive reaction data hub can be part of a two-sided marketplace. Data reception by an individual and a content provider is enabled. The enabling can be accomplished using a web browser, a plug-in to a web browser, etc. Cognitive state data including facial data is collected on the individual. The cognitive state data that is collected can further include audio data, physiological data, and the like. The collecting of the cognitive state data can be accomplished using a webcam or other video capture device such as a camera coupled to an electronic device associated with the individual, a camera coupled to a vehicle, and so on. Processors are used to analyze the cognitive state data and to provide the results to the individual. Cognitive state data is evaluated and the results are provided to the content provider.

An example dashboard is shown 410. The dashboard can include a variety of fields, panes, settings, etc., where the fields can be configured by a content provider, configured by the individual, and so on. The dashboard can include a title 412 for the dashboard. The dashboard can comprise fields 414, where the fields can include pulldown menus, radio buttons, settings, adjustments, etc., can be used to display cognitive state and other information to the individual. The dashboard can include controls for selecting among various dashboards. The dashboards can include a cognitive state dashboard, a mood dashboard, an emotional state dashboard, a mental state dashboard, etc. The dashboard can comprise a user pane 416. The user pane can show an image of the user, a video, a selfie, an emoji, a caricature, a cartoon, an animation, a selected image, and so on. A selected dashboard or default dashboard can display activity 420 of the individual. The activity of the individual can include a list of who may see a cognitive state indication, a range of dates over which cognitive state data can be shown, types of emotions, facial expressions, and so on. The activity pane can include the activity of others, a list of emotions and expressions, selfie settings, screenshot settings, and so on.

The dashboard can show a current media article 430. The current media article can include a webpage, a video, a media presentation, etc. The current media can include an image of a webpage being observed by the individual. The dashboard can include moment-by-moment metrics 440, where the moment-by-moment metrics can be based on cognitive state data. The cognitive state data can be indicative of drowsiness, fatigue, distraction, impairment, sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, depression, envy, sympathy, embarrassment, poignancy, or mirth. The moment-by-moment metrics can include physiological data that can be captured along with the collecting cognitive state data. A plurality of metrics can be displayed. A selector 442 can be used to determine values for one or metrics at a given time.

Figure 5:
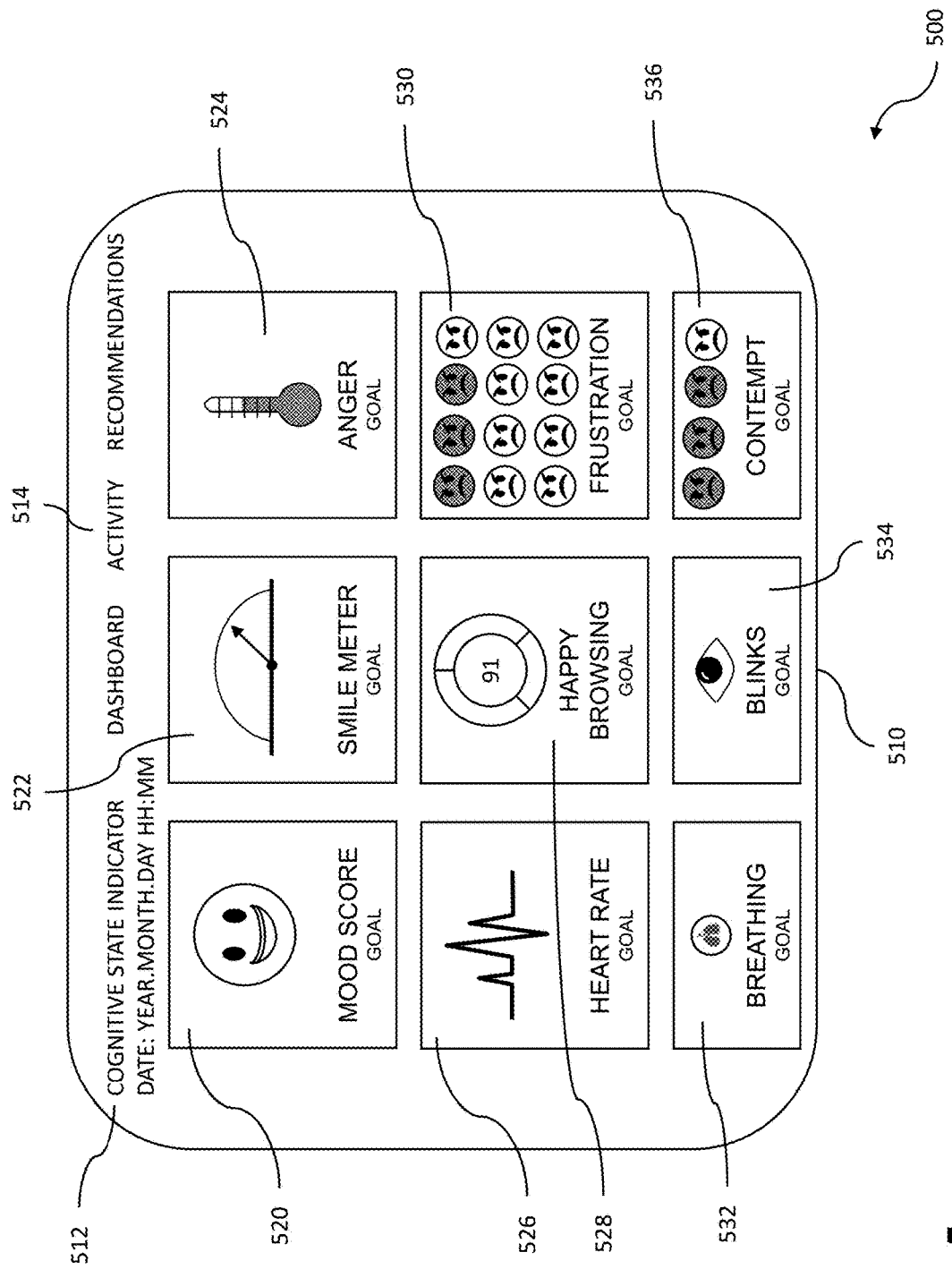
FIG. 5 illustrates an example dashboard.

FIG. 5 illustrates an example dashboard 500. A dashboard can be used to display information to an individual, where the information is based on image analysis for a two-sided data hub. Data reception, where the data can include web content, is enabled by an individual and a content provider. Cognitive state data including facial data is collected on the individual. The collecting cognitive state data including facial data on the individual can be accomplished using a webcam. In embodiments, the webcam can be integrated into a device displaying content from the content provider. In other embodiments, the webcam can be included in a device different from the device displaying content from the content provider. One or more processors are used to analyze the cognitive state data for providing analysis of the cognitive state data to the individual. The cognitive state data is evaluated and the results are provided to the content provider.

A dashboard, such as example dashboard 510, can display a variety of information to an individual. The dashboard can be rendered on a display such as a display coupled to an electronic device associated with the individual, an electronic display coupled to a vehicle, and so on. The electronic device can include a smartphone, a personal digital assistant, a tablet computer, a laptop computer, and the like. The electronic display can be coupled to a wearable electronic device such as a smart watch, smart glasses, etc. The electronic display that can be coupled to a vehicle can include an in-dashboard display, a dashboard mounted display, a "heads up" display, and the like. The example dashboard can include displayed information such as a mood score 520, a meter, such as a smile meter 522, and a target number of smiles per day, an anger meter 524 with daily goal, a heart rate with daily goal 526, a browsing mood such as happy browsing 528, a frustration meter and goal 530, a breathing meter and goal 532, an eye blinks meter and goal 534, a contempt meter and goal 536, and so on. The dashboard 510 can include controls 512 which can be used to select among multiple dashboards, to display time or date information, to display various activities 514, to take action or receive suggestions for such activities that would a mood, and so on.

Figure 6:
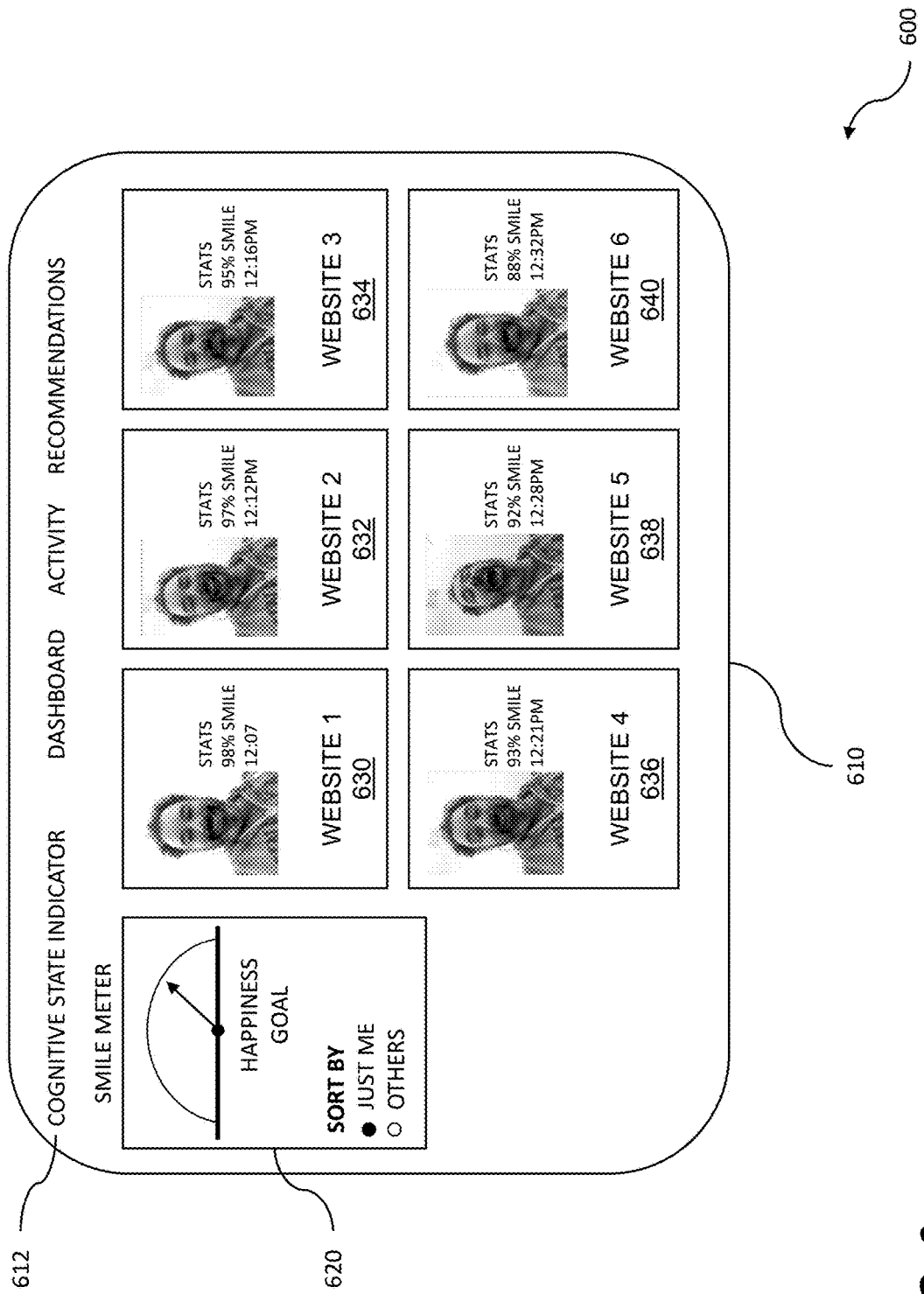
FIG. 6 shows statistical results.

FIG. 6 shows statistical results. Various statistical results can be determined using image analysis for a two-sided data hub. The statistics can be used to associate various cognitive states experienced by an individual as that individual views web content. The cognitive state data collected from the individual can be analyzed, and the results can be displayed to the individual. The cognitive state data collected from the individual can be evaluated, providing results to the content provider. Statistical results 600 based on the analyzing and the evaluating can be displayed to an individual using a dashboard 610. The dashboard can include a mood dashboard. The dashboard can display statistical results for a variety of cognitive states, moods, etc., such as happy, sad, confused, angry, annoyed, concentrating, bored, and so on. The dashboard can display statistical results based on a variety of cognitive states, emotional states, mental states, moods, etc. The displayed cognitive states, moods, emotions, mental states, and so on, can be based on cognitive state data associated with the individual or on aggregating the cognitive state data from the individual with cognitive state data from other individuals. The cognitive state data for the individual can be compared to the aggregated cognitive state data from the other individuals. The cognitive state data from other individuals can be based on demographics such as age, gender, race, geographic location, educational level, household income, etc.

The dashboard 610 can include controls 612. The controls 612 can be used to selected various views, activities, actions, recommendations, and so on. The dashboard can display a variety of cognitive states, facial expressions, emotional states, mental states, moods, and the like. The facial expressions, for example, can include smiles, frowns, smirks, neutral expressions, etc. The dashboard 610, when displaying smiles, can include a smile meter 620. The smile meter can include a display for level of happiness, a goal, sorting options such as most recent smile and biggest smiles, selfie settings, screenshot settings, etc. The statistical results of a mood such as a smile can be displayed with various statistics. The statistics for smiles can include a percentage of time smiling, the time at which the smile occurred, the most intense smile, the longest smile, the website for which the smile occurred, an image of the individual for whom the statistical results are being displayed, etc.

Several renderings of statistics for a cognitive state, emotional state, facial expression, mood, and so on, can be display simultaneously. The renderings can be associated with one or more websites. In the figure, the statistics for six websites are shown. While six renderings of statistics associated with the six websites are shown, other numbers of renderings of statistics can be displayed. The statics for website 1 630 are rendered. The rendering of the statistics for website 1 include an image such as a selfie of the individual, statics for a percentage smile, and the time at which the individual view website 1. The statistics for website 2 632 can be rendered. The individual has "surfed" from website 1 to web site 2. An image of the individual is shown and a percentage smile is determined for a second time, the time at which website 2 was viewed. The individual continues surfing the web to website 3 634. The rendering for website 3 includes an image of the individual, the percent smile, and the time at which the smile percentage was determined. The individual continues surfing the web to other websites, such as website 4 636, website 5 638, and website 6 640. For each of the websites, an image such as a selfie of the individual can be shown along with various statistics. Since the statistics include smiles, the percentages of smile analyzed and evaluated at each website are rendered along with a time at which the individual viewed the content at the websites. The percentages of smiles may change while the individual consumes web content from various websites. The percentages can change due to content that may not appeal to the individual, fatigue, distraction, and so on. Additional renderings can be displayed, where the additional renderings can be associated with cognitive states, facial expressions, emotional states, moods, etc. The other cognitive states can be indicative of drowsiness, fatigue, distraction, impairment, etc.

Figure 7:
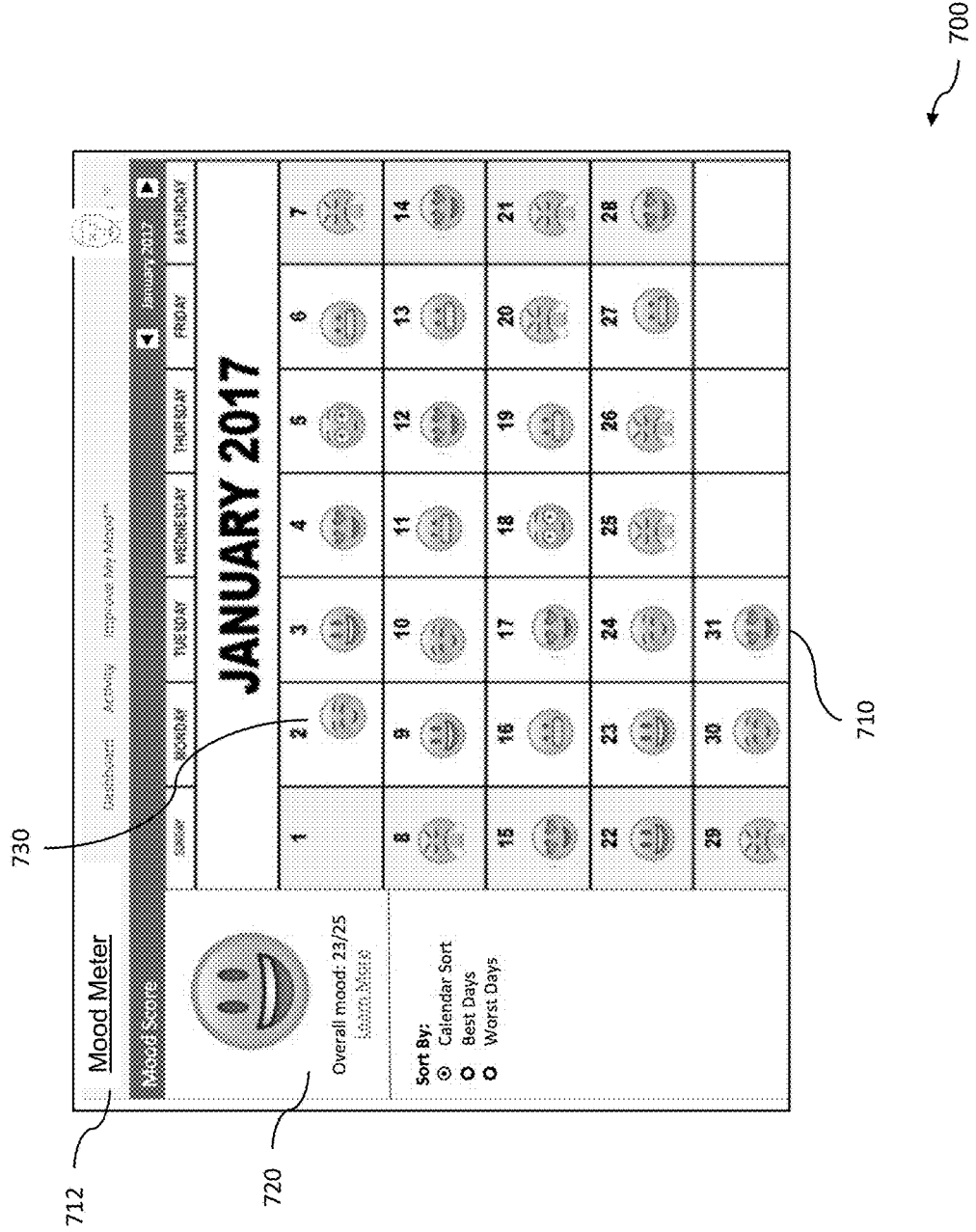
FIG. 7 illustrates a calendar displaying mood.

FIG. 7 illustrates a calendar displaying mood. The calendar displaying mood can be can be a part of a mood dashboard that can be displayed to an individual. The mood dashboard can be based on image analysis for a two-sided data hub. The two-sided data hub can include a cognitive reaction data hub. The cognitive reaction data hub can be part of a two-sided marketplace where data reception is enabled by both an individual and a content provider. Cognitive state data including facial data is collected on the individual. One or more processors analyze the cognitive state data and provide the results to the individual. Cognitive state data is also evaluated and the results are provided to the content provider. A calendar displaying mood 700 can include displaying a mood dashboard 710 to the individual based on the analyzing. The mood dashboard 710 can include controls 712 that can be used to select display options, to monitor activities, to take steps to improve a mood, to receive suggestions for improving a mood, and so on. The mood dashboard can be used to display the moods of an individual based on cognitive state data including facial data collected over a period of time such as a day, a week, a month, and so on. The calendar of the mood dashboard can display an overall mood 720. The overall mood can be based on comparing the cognitive state data collected from the individual with cognitive state data collected from other individuals. In embodiments, the comparing can provide quantified self-information on cognitive states for the individual. The calendar of the mood dashboard can be sorted using various criteria. The various criteria can include moods across a month, best days of the month, worst days of the month, and so on. One or more emoji 730 can be used to represent an overall mood of the individual for a given day.

Figure 8:
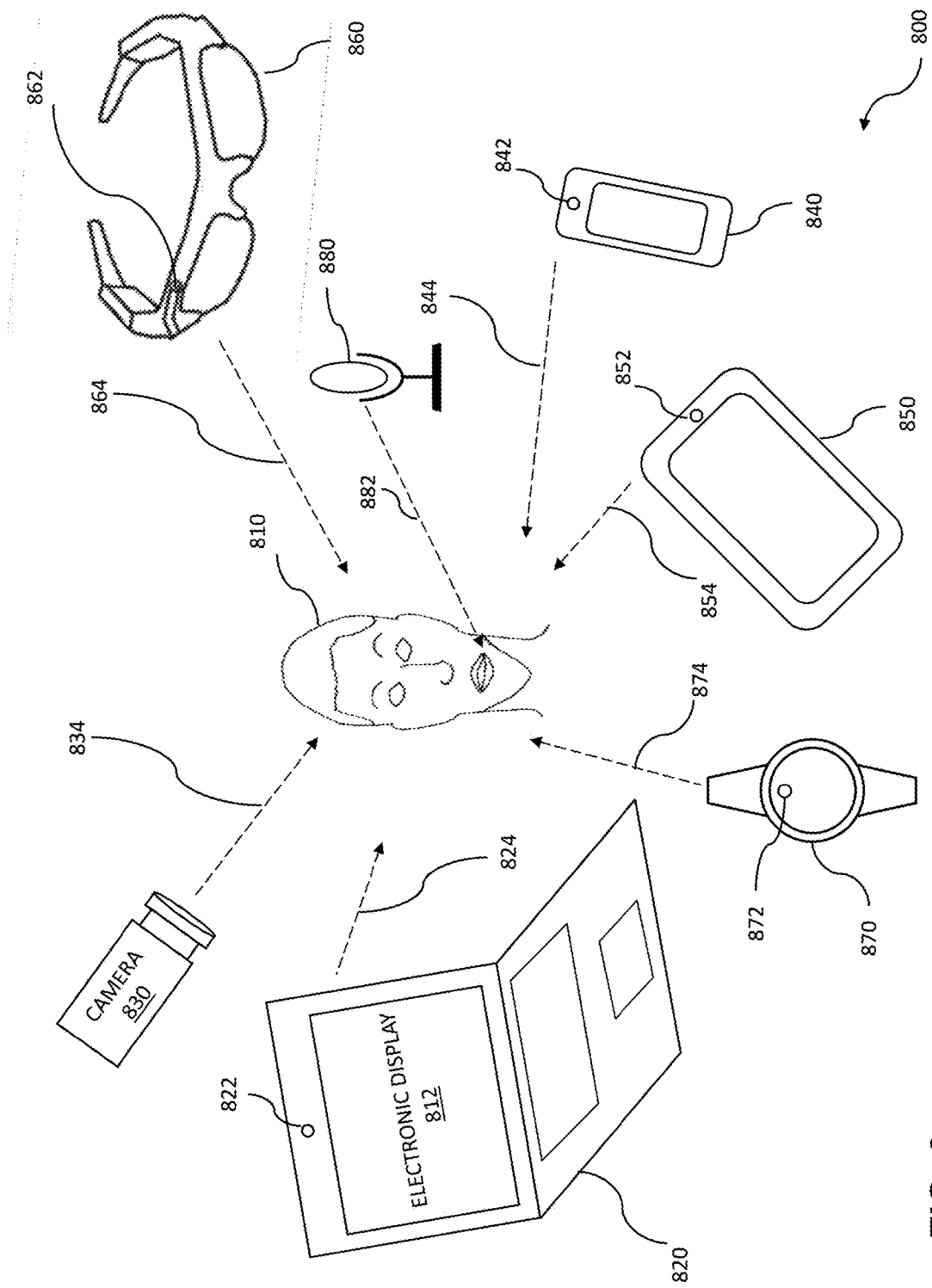
FIG. 8 shows example image and audio collection including multiple mobile devices.

FIG. 8 shows example image and audio collection including multiple mobile devices. Cognitive state data including image data, audio data, physiological data, etc., can be collected using multiple mobile devices. The collected cognitive state data can be used for image analysis for a two-sided data hub. Data reception is enabled by an individual and a content provider, and cognitive state data including facial data is collected on the individual. Analysis of the cognitive state data is provided to the individual, and evaluation of the cognitive state data is provided to the content provider. A mood dashboard is displayed to the individual. While one person is shown, in practice the video data or audio data on any number of people can be collected. In the diagram 800, the multiple mobile devices can be used separately or in combination to collect video data, audio data, or both video data and audio data on a user 810. A user 810 can be observed as she or he is performing a task, experiencing an event, viewing a media presentation, and so on. The user 810 can be shown one or more media presentations, political presentations, social media, or another form of displayed media. The one or more media presentations can be shown to a plurality of people. The media presentations can be displayed on an electronic display 812 or another display. The data collected on the user 810 or on a plurality of users can be in the form of one or more videos, video frames, and still images; one or more audio channels, etc. The plurality of video data and audio data can be of people who are experiencing different situations. Some example situations can include the user or plurality of users being exposed to TV programs, movies, video clips, social media, and other such media. The situations could also include exposure to media such as advertisements, political messages, news programs, and so on.

As noted before, video data and audio data can be collected on one or more users in substantially identical or different situations while viewing either a single media presentation or a plurality of presentations. The data collected on the user 810 can be analyzed and viewed for a variety of purposes including expression analysis, cognitive state analysis, mental state analysis, emotional state analysis, and so on. The electronic display 812 can be on a laptop computer 820 as shown, a tablet computer 850, a cell phone 840, a television, a mobile monitor, or any other type of electronic device. In one embodiment, video data including expression data is collected on a mobile device such as a cell phone 840, a tablet computer 850, a laptop computer 820, or a watch 870. Similarly, the audio data including speech data and non-speech vocalizations can be collected on one or more of the mobile devices. Thus, the multiple sources can include at least one mobile device, such as a phone 840 or a tablet 850, or a wearable device such as a watch 870 or glasses 860. A mobile device can include a forward-facing camera and/or a rear-facing camera that can be used to collect expression data. A mobile device can include a microphone, audio transducer, or other audio capture apparatus that can be used to capture the speech and non-speech vocalizations. Sources of expression data can include a webcam 822, a phone camera 842, a tablet camera 852, a wearable camera 862, and a mobile camera 830. A wearable camera can comprise various camera devices, such as a watch camera 872. Sources of audio data 882 can include a microphone 880.

As the user 810 is monitored, the user might move due to the nature of the task, boredom, discomfort, distractions, or for another reason. As the user moves, the camera with a view of the user's face can be changed. Thus, as an example, if the user is looking in a first direction, the line of sight 824 from the webcam 822 is able to observe the user's face, but if the user is looking in a second direction, the line of sight 834 from the mobile camera 830 is able to observe the user's face. Furthermore, in other embodiments, if the user is looking in a third direction, the line of sight 844 from the phone camera 842 is able to observe the user's face, and if the user is looking in a fourth direction, the line of sight 854 from the tablet camera 852 is able to observe the user's face. If the user is looking in a fifth direction, the line of sight 864 from the wearable camera 862, which can be a device such as the glasses 860 shown and can be worn by another user or an observer, is able to observe the user's face. If the user is looking in a sixth direction, the line of sight 874 from the wearable watch-type device 870, with a camera 872 included on the device, is able to observe the user's face. In other embodiments, the wearable device is another device, such as an earpiece with a camera, a helmet or hat with a camera, a clip-on camera attached to clothing, or any other type of wearable device with a camera or other sensor for collecting expression data. The user 810 can also use a wearable device including a camera for gathering contextual information and/or collecting expression data on other users. Because the user 810 can move her or his head, the facial data can be collected intermittently when she or he is looking in a direction of a camera. In some cases, multiple people can be included in the view from one or more cameras, and some embodiments include filtering out faces of one or more other people to determine whether the user 810 is looking toward a camera. All or some of the expression data can be continuously or sporadically available from the various devices and other devices.

The captured video data can include facial expressions and can be analyzed on a computing device such as the video capture device or on another separate device. The analysis can take place on one of the mobile devices discussed above, on a local server, on a remote server, and so on. In embodiments, some of the analysis takes place on the mobile device, while other analysis takes place on a server device. The analysis of the video data can include the use of a classifier. The video data can be captured using one of the mobile devices discussed above and sent to a server or another computing device for analysis. However, the captured video data including expressions can also be analyzed on the device which performed the capturing. The analysis can be performed on a mobile device where the videos were obtained with the mobile device and wherein the mobile device includes one or more of a laptop computer, a tablet, a PDA, a smartphone, a wearable device, and so on. In another embodiment, the analyzing comprises using a classifier on a server or another computing device other than the capturing device.

Figure 9:
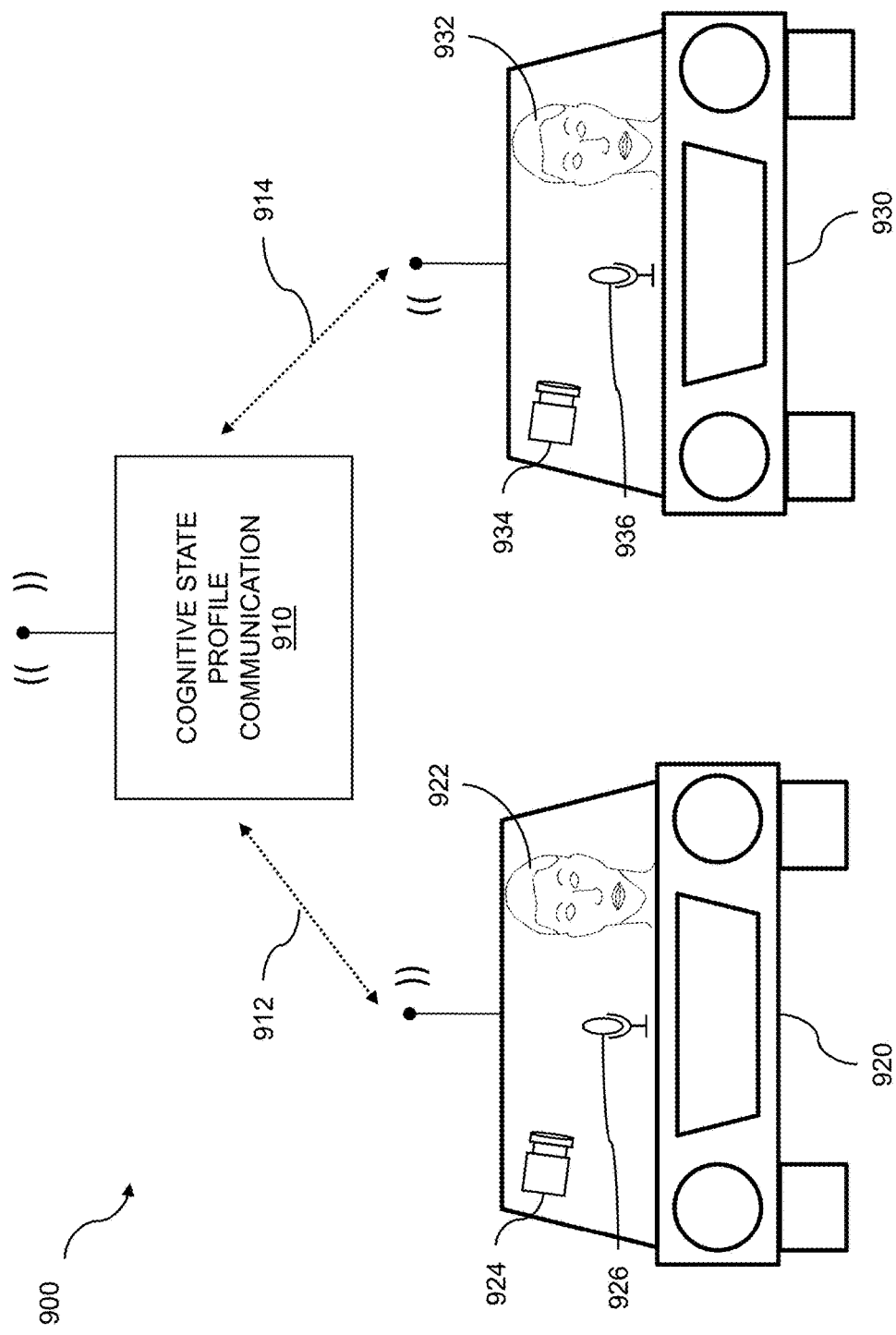
FIG. 9 is a system diagram for vehicle manipulation.

FIG. 9 is a system diagram for vehicle manipulation. Vehicle manipulation can be based on image analysis for a two-sided data hub. Data reception is enabled by an individual and a content provider. Cognitive state data, facial data, audio data, etc., can be collected on the individual. The cognitive state data is analyzed and provided to the individual. The cognitive state data is evaluated and provided for to the content provider. A system 900 for vehicle manipulation is shown. The system can include cognitive state profile communication 910. The communicating of the cognitive state profile communication can include sending cognitive state profile information to a first vehicle 920, to a second vehicle 930, and so on. The cognitive state profile communication can include manipulating the first vehicle 920, the second vehicle 930, etc. The manipulating can include a locking out operation; recommending a break for the occupant; recommending a different route; recommending how far to drive; responding to traffic; adjusting seats, mirrors, climate control, lighting, music, audio stimuli, interior temperature for the second vehicle; brake activation; steering control; and other vehicle control and manipulation techniques.

The cognitive state profile can be sent to a first vehicle 920 using a wireless link 912 or other data transfer technique. The cognitive state profile that can be sent can be based on cognitive state data including facial data from an occupant 922 of the first vehicle 920. The cognitive state data including facial data can be collected using a camera 924 or other image capture technique. The system 900 can include collecting voice data and augmenting the cognitive state data with the voice data. The voice data can be collected from the occupant 922 using a microphone 926 or other audio capture technique. The voice data can include audio data, where the audio data can include traffic sounds, road noise, music, news, eBooks, etc., that can be played by the occupant, and so on. The system 900 can include evaluating the voice data for timbre, prosody, vocal register, vocal resonance, pitch, loudness, speech rate, or language content. The evaluating the voice data can also be used in evaluating the cognitive state or states of the occupant 922 of the first vehicle 920. In embodiments, the augmenting can be based on lexical analysis of the voice data that considers sentiment. As for the first vehicle, the cognitive state profile can be sent to a second vehicle 930 using a wireless link 914 or other data transfer technique. The cognitive state profile can be based on cognitive state data including facial data from an occupant 932 of the second vehicle 930, can be based on the cognitive state data including facial data from the occupant 922 of the first vehicle 920, and so on. The cognitive state data including facial data can be collected using a camera 934 or other image capture technique. The system 900 can include collecting voice data from the occupant 932 using a microphone 936 or other audio capture technique.

Figure 10:
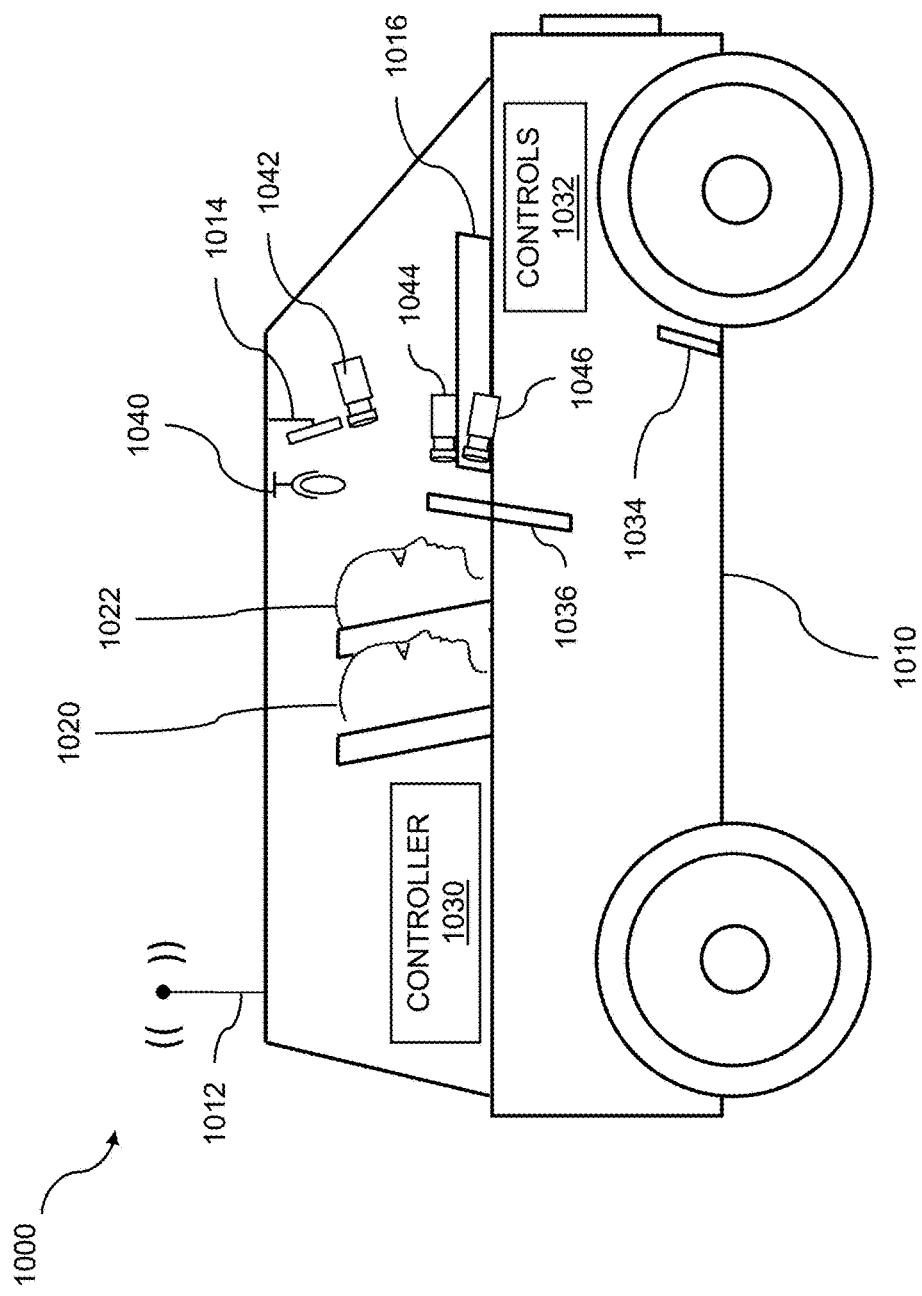
FIG. 10 is a system diagram for an interior of a vehicle

FIG. 10 is a system diagram for an interior of a vehicle 1000. Cognitive state data including facial data, audio data, and so on, can be collected from an individual while that individual is within a vehicle. The individual and a content provider can enable data reception, and the cognitive state data including the facial data can be collected on the individual. Analysis of the cognitive state data can be provided to the individual, and evaluation of the cognitive state data can be provided to the content provider. A mood dashboard can be rendered for the individual, where the rendering can be performed using a display or monitor within the vehicle. In embodiments, a cognitive state, mental state, emotional state, mood, etc., of the individual, can be used for manipulating the vehicle. One or more occupants of a vehicle 1010, such as occupants 1020 and 1022, can be observed using a microphone 1040, one or more cameras 1042, 1044, or 1046, and other audio and image capture techniques. The image data can include video data. The video data and the audio data can include cognitive state data, where the cognitive state data can include facial data, voice data, physiological data, and the like. The occupant can be a driver 1022 of the vehicle 1010, a passenger 1020 within the vehicle, and so on.

The cameras or imaging devices that can be used to obtain images including facial data from the occupants of the vehicle 1010 can be positioned to capture the face of the vehicle operator, the face of a vehicle passenger, multiple views of the faces of occupants of the vehicle, and so on. The cameras can be located near a rear-view mirror 1014 such as camera 1042, can be positioned near or on a dashboard 1016 such as camera 1044, can be positioned within the dashboard such as camera 1046, and so on. The microphone or audio capture device 1040 can be positioned within the vehicle such that voice data, speech data, non-speech vocalizations, and so on, can be easily collected with minimal background noise. In embodiments, additional cameras, imaging devices, microphones, audio capture devices, and so on, can be located throughout the vehicle. In further embodiments, each occupant of the vehicle could have multiple cameras, microphones, etc., positioned to capture video data and audio data from that occupant.

The interior of a vehicle 1010 can be a standard vehicle, an autonomous vehicle, a semi-autonomous vehicle, and so on. The vehicle can be a sedan or other automobile, a van, a sport utility vehicle (SUV), a truck, a bus, a special purpose vehicle, and the like. The interior of the vehicle 1010 can include standard controls such as a steering wheel 1036, a throttle control (not shown), a brake 1034, and so on. The interior of the vehicle can include other controls 1032 such as controls for seats, mirrors, climate controls, audio systems, etc. The controls 1032 of the vehicle 1010 can be controlled by a controller 1030. The controller 1030 can control the vehicle 1010 in various manners such as autonomously, semi-autonomously, assertively to a vehicle occupant 1020 or 1022, etc. In embodiments, the controller provides vehicle control or manipulation techniques, assistance, etc. The controller 1030 can receive instructions via an antenna 1012 or using other wireless techniques. The controller 1030 can be preprogrammed to cause the vehicle to follow a specific route. The specific route that the vehicle is programmed to follow can be based on the cognitive state of the vehicle occupant. The specific route can be chosen based on lowest stress, least traffic, most scenic view, shortest route, and so on.

Figure 11:
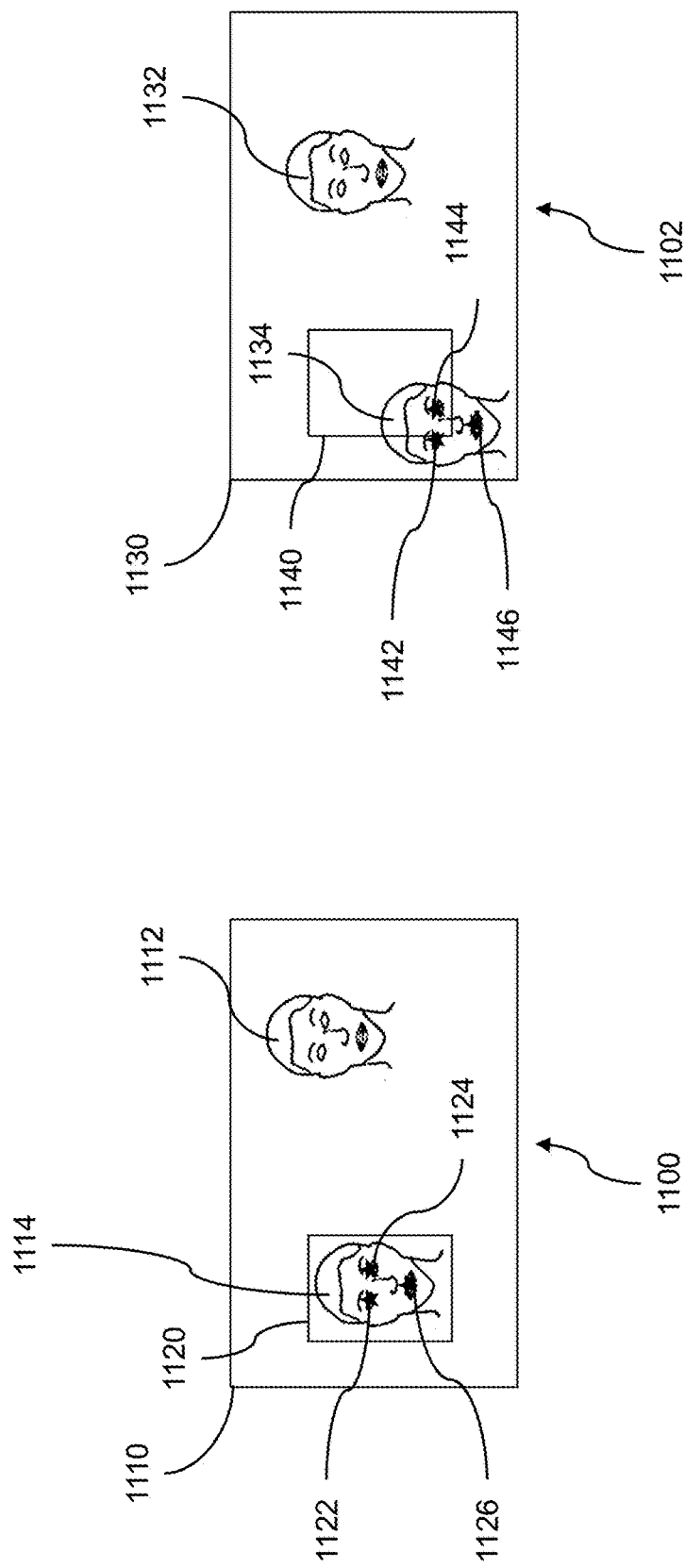
FIG. 11 illustrates feature extraction for multiple faces.

FIG. 11 illustrates feature extraction for multiple faces. Image analysis, including facial analysis, can be based on feature extraction from multiple faces. Feature extraction for one or more faces can be applied to image analysis for a two-sided hub. Data reception is enabled by an individual and a content provider. Cognitive state data including facial data is collected on the individual. Analysis of the cognitive state data is provided to the individual, and evaluation of the cognitive state data is provided to the content provider. A mood dashboard is displayed to the individual.

The feature extraction for multiple faces can be performed for faces detected in multiple images. In embodiments, the features of multiple faces are extracted for evaluating cognitive states. Features of a face or a plurality of faces can be extracted from collected video data. The feature extraction can be performed by analysis, by using one or more processors, by using one or more video collection devices, and by using a server. The analysis device can be used to perform face detection for a second face, as well as to perform facial tracking of the first face. One or more videos can be captured, where the videos contain one or more faces. The video or videos that contain the one or more faces can be partitioned into a plurality of frames, and the frames can be analyzed for the detection of the one or more faces. The analysis of the one or more video frames can be based on one or more classifiers. A classifier can be an algorithm, heuristic, function, or piece of code that can be used to identify into which of a set of categories a new or existing observation, sample, datum, etc. should be placed. The decision to place an observation into a category can be based on training the algorithm or piece of code by analyzing a known set of data, referred to as a training set. The training set can include data for which category memberships of the data can be known. The training set can be used as part of a supervised training technique. If a training set is not available, then a clustering technique can be used to group observations into categories. The latter approach, or unsupervised learning, can be based on a measure (i.e. distance) of one or more inherent similarities among the data that is being categorized. When a new observation is received, then the classifier can be used to categorize the new observation. Classifiers can be used for many analysis applications, including analysis of one or more faces. The use of classifiers can be the basis of analyzing the one or more faces for gender, ethnicity, and age; of detecting the one or more faces in one or more videos; of detecting facial features and landmarks; and so on. The observations can be analyzed based on one or more of a set of quantifiable properties. The properties can be described as features, and explanatory variables involving various data types can include numerical (integer-valued, real-valued), ordinal, categorical, and so on. Some classifiers can be based on a comparison between an observation and prior observations and can also be based on functions such as a similarity function, a distance function, and so on.

Classification can be based on various types of algorithms, heuristics, codes, procedures, statistics, and so on. Many techniques exist for performing classification. This classification of one or more observations into one or more groups can be based on distributions of the data values, probabilities, and so on. Classifiers can be binary, multiclass, linear, etc. Algorithms for classification can be implemented using a variety of techniques, including neural networks, kernel estimation, support vector machines, use of quadratic surfaces, and so on. Classification can be used in many application areas such as computer vision, and speech and handwriting recognition. Classification can be used for biometric identification of one or more people in a single frame or in multiple frames of one or more videos.

Returning to FIG. 11, the detection of the first face, the second face, and multiple faces can include identifying facial landmarks, generating a bounding box, and predicting a bounding box and landmarks for a next frame, where the next frame can be one of a plurality of frames of a video containing faces. A first video frame 1100 includes a frame boundary 1110, a first face 1112, and a second face 1114. The video frame 1100 also includes a bounding box 1120. Facial landmarks can be generated for the first face 1112. Face detection can be performed to initialize a second set of locations for a second set of facial landmarks for a second face within the video. Facial landmarks in the video frame 1100 can include the facial landmarks 1122, 1124, and 1126. The facial landmarks can include corners of a mouth, corners of eyes, eyebrow corners, the tip of the nose, nostrils, chin, the tips of ears, and so on. The performing of face detection on the second face can include performing facial landmark detection with the first frame from the video for the second face and can include estimating a second rough bounding box for the second face based on the facial landmark detection. The estimating of a second rough bounding box can include the bounding box 1120. Bounding boxes can also be estimated for one or more other faces within the boundary 1110. The bounding box can be refined, as can the one or more facial landmarks. The refining of the second set of locations for the second set of facial landmarks can be based on localized information around the second set of facial landmarks. The bounding box 1120 and the facial landmarks 1122, 1124, and 1126 can be used to estimate future locations for the second set of locations for the second set of facial landmarks in a future video frame from the first video frame.

A second video frame 1102 is also shown. The second video frame 1102 includes a frame boundary 1130, a first face 1132, and a second face 1134. The second video frame 1102 also includes a bounding box 1140 and the facial landmarks, or points, 1142, 1144, and 1146. In other embodiments, multiple facial landmarks are generated and used for facial tracking of the two or more faces of a video frame, such as the shown second video frame 1102. Facial points from the first face can be distinguished from other facial points. In embodiments, the other facial points include facial points of one or more other faces. The facial points can correspond to the facial points of the second face. The distinguishing of the facial points of the first face and the facial points of the second face can be used to differentiate between the first face and the second face, to track either the first face, the second face, or both faces, and so on. Other facial points can correspond to the second face. As mentioned above, multiple facial points can be determined within a frame. One or more of the other facial points that are determined can correspond to a third face. The location of the bounding box 1140 can be estimated, where the estimating can be based on the location of the generated bounding box 1120 shown in the first video frame 1100. The three facial points shown, facial points, or landmarks, 1142, 1144, and 1146, might lie within the bounding box 1140 or might not lie partially or completely within the bounding box 1140. For instance, the second face 1134 might have moved between the first video frame 1100 and the second video frame 1102. Based on the accuracy of the estimating of the bounding box 1140, a new estimation can be determined for a third, future frame from the video, and so on. The evaluation can be performed, all or in part, using semiconductor-based logic.

Figure 12:
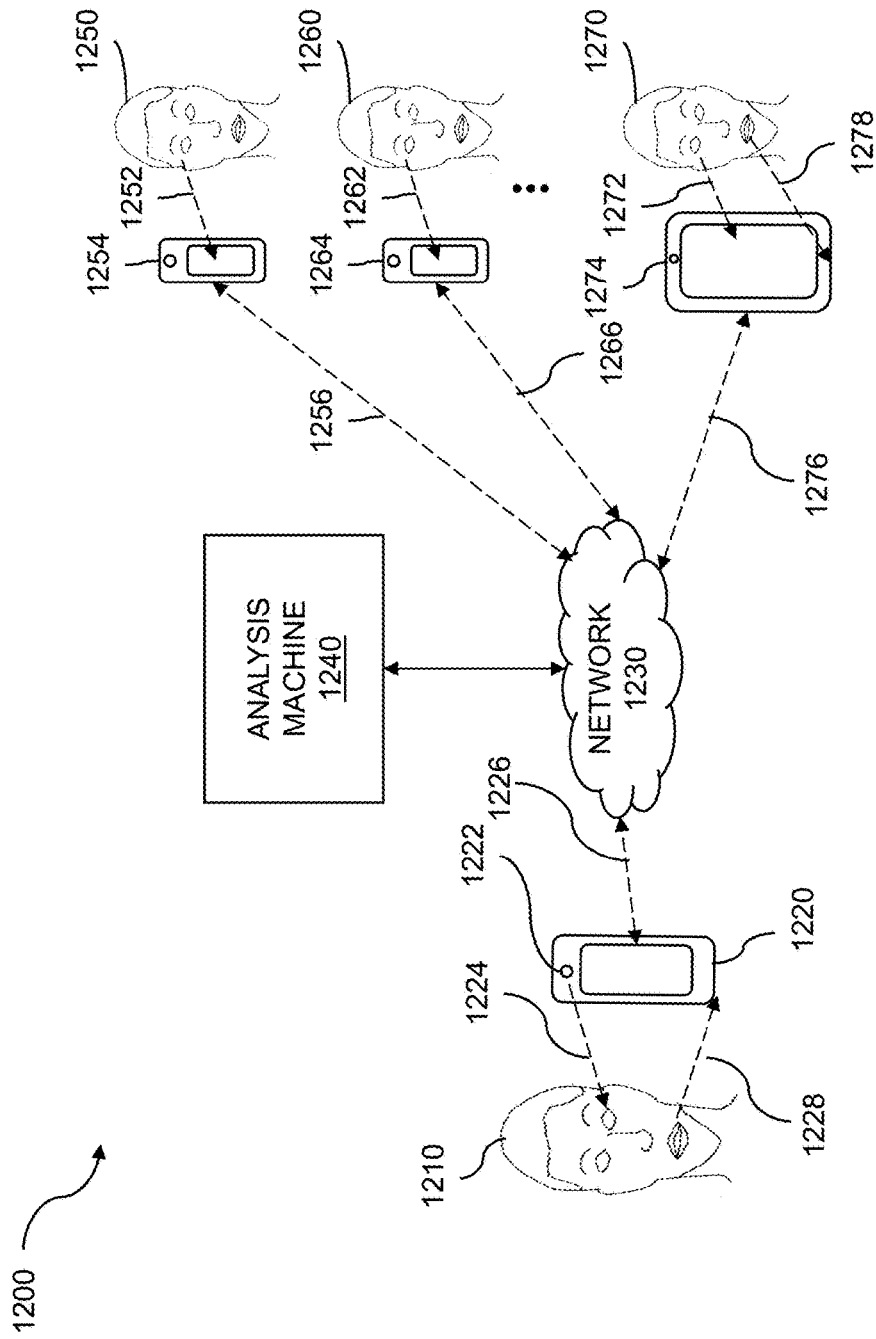
FIG. 12 shows an example of live streaming of social video and audio.

FIG. 12 shows an example of live streaming of social video and audio. The streaming of social video and social audio can be applied to image analysis for a two-sided data hub. The live streaming can include cognitive state data, image data, facial data, speech data, audio data, etc. An individual and a content provider enable data reception. Cognitive state data including facial data is collected on the individual. The cognitive state data is analyzed and evaluated. The cognitive state data is analyzed to provide analysis to the individual. The cognitive state data is evaluated to provide evaluation to the content provider.

The live streaming and image analysis 1200 can be facilitated by a video capture device, a local server, a remote server, a semiconductor-based logic, and so on. The streaming can be live streaming and can include cognitive state analysis, cognitive state event signature analysis, etc. Live streaming video is an example of one-to-many social media, where video can be sent over the Internet from one person to a plurality of people using a social media app and/or platform. Live streaming is one of numerous popular techniques used by people who want to disseminate ideas, send information, provide entertainment, share experiences, and so on. Some of the live streams, such as webcasts, online classes, sporting events, news, computer gaming, or video conferences can be scheduled, while others can be impromptu streams that are broadcast as needed or when desirable. Examples of impromptu live stream videos can range from individuals simply wanting to share experiences with their social media followers, to live coverage of breaking news, emergencies, or natural disasters. The latter coverage is known as mobile journalism, or "mo jo", and is becoming increasingly common. With this type of coverage, news reporters can use networked, portable electronic devices to provide mobile journalism content to a plurality of social media followers. Such reporters can be quickly and inexpensively deployed as the need or desire arises.

Several live streaming social media apps and platforms can be used for transmitting video. One such video social media app is Meerkat™ which can link with a user's Twitter™ account. Meerkat™ enables a user to stream video using a handheld, networked electronic device coupled to video capabilities. Viewers of the live stream can comment on the stream using tweets that can be seen and responded to by the broadcaster. Another popular app is Periscope™ which can transmit a live recording from one user to his or her Periscope™ account and to other followers. The Periscope™ app can be executed on a mobile device. The user's Periscope™ followers can receive an alert whenever that user begins a video transmission. Another live-stream video platform is Twitch™ which can be used for video streaming of video gaming and broadcasts of various competitions and events.

The example 1200 shows a user 1210 broadcasting a video live stream and an audio live stream to one or more people as shown by a first person 1250, a second person 1260, and a third person 1270. A portable, network-enabled, electronic device 1220 can be coupled to a front-facing camera 1222. The portable electronic device 1220 can be a smartphone, a PDA, a tablet, a laptop computer, and so on. The camera 1222 coupled to the device 1220 can have a line-of-sight view 1224 to the user 1210 and can capture video of the user 1210. The portable electronic device 1220 can be coupled to a microphone (not shown). The microphone can capture voice data 1228 such as speech and non-speech vocalizations. In embodiments, non-speech vocalizations can include grunts, yelps, squeals, snoring, sighs, laughter, filled pauses, unfilled pauses, yawns, or the like. The captured video and audio can be sent to an analysis or recommendation engine 1240 using a network link 1226 to the Internet 1230. The network link can be a wireless link, a wired link, and so on. The recommendation engine 1240 can recommend to the user 1210 an app and/or platform that can be supported by the server and can be used to provide a video live stream, an audio live stream, or both a video live stream and an audio live stream to one or more followers of the user 1210.

In the example 1200, the user 1210 has three followers: a first person 1250, a second person 1260, and a third person 1270. Each follower has a line-of-sight view to a video screen on a portable, networked electronic device. In other embodiments, one or more followers follow the user 1210 using any other networked electronic device, including a computer. In the example 1200, a first person 1250 has a line-of-sight view 1252 to the video screen of a device 1254; a second person 1260 has a line-of-sight view 1262 to the video screen of a device 1264, and a third person 1270 has a line-of-sight view 1272 to the video screen of a device 1274. The device 1274 can also capture audio data 1278 from the third person 1270. The portable electronic devices 1254, 1264, and 1274 can each be a smartphone, a PDA, a tablet, and so on. Each portable device can receive the video stream and the audio stream being broadcast by the user 1210 through the Internet 1230 using the app and/or platform that can be recommended by the recommendation engine 1240. The device 1254 can receive a video stream and the audio stream using the network link 1256, the device 1264 can receive a video stream and the audio stream using the network link 1266, the device 1274 can receive a video stream and the audio stream using the network link 1276, and so on. The network link can be a wireless link, a wired link, a hybrid link, and so on. Depending on the app and/or platform that can be recommended by the recommendation engine 1240, one or more followers, such as the followers shown 1250, 1260, and 1270, can reply to, comment on, or otherwise provide feedback to the user 1210 using their respective devices 1254, 1264, and 1274.

The human face provides a powerful communications medium through its ability to exhibit numerous expressions that can be captured and analyzed for a variety of purposes. In some cases, media producers are acutely interested in evaluating the effectiveness of message delivery by video media. Such video media includes advertisements, political messages, educational materials, television programs, movies, government service announcements, etc. Automated facial analysis can be performed on one or more video frames containing a face in order to detect facial action. Based on the facial action detected, a variety of parameters can be determined, including affect valence, spontaneous reactions, facial action units, and so on. The parameters that are determined can be used to infer or predict emotional, mental, and cognitive states. For example, determined valence can be used to describe the emotional reaction of a viewer to a video media presentation or another type of presentation. Positive valence provides evidence that a viewer is experiencing a favorable emotional response to the video media presentation, while negative valence provides evidence that a viewer is experiencing an unfavorable emotional response to the video media presentation. Other facial data analysis can include the determination of discrete emotional states of the viewer or viewers.

Facial data can be collected from a plurality of people using any of a variety of cameras. A camera can include a webcam, a video camera, a still camera, a thermal imager, a CCD device, a phone camera, a three-dimensional camera, a depth camera, a light field camera, multiple webcams used to show different views of a person, or any other type of image capture apparatus that can allow captured data to be used in an electronic system. In some embodiments, the person is permitted to "opt-in" to the facial data collection. For example, the person can agree to the capture of facial data using a personal device such as a mobile device or another electronic device by selecting an opt-in choice. Opting-in can then turn on the person's webcam-enabled device and can begin the capture of the person's facial data via a video feed from the webcam or other camera. The video data that is collected can include one or more persons experiencing an event. The one or more persons can be sharing a personal electronic device or can each be using one or more devices for video capture. The videos that are collected can be collected using a web-based framework. The web-based framework can be used to display the video media presentation or event as well as to collect videos from multiple viewers who are online. That is, the collection of videos can be crowdsourced from those viewers who elected to opt-in to the video data collection.

The videos captured from the various viewers who chose to opt-in can be substantially different in terms of video quality, frame rate, etc. As a result, the facial video data can be scaled, rotated, and otherwise adjusted to improve consistency. Human factors further contribute to the capture of the facial video data. The facial data that is captured might or might not be relevant to the video media presentation being displayed. For example, the viewer might not be paying attention, might be fidgeting, might be distracted by an object or event near the viewer, or might be otherwise inattentive to the video media presentation. The behavior exhibited by the viewer can prove challenging to analyze due to viewer actions including eating, speaking to another person or persons, speaking on the phone, etc. The videos collected from the viewers might also include other artifacts that pose challenges during the analysis of the video data. The artifacts can include items such as eyeglasses (because of reflections), eye patches, jewelry, and clothing that occludes or obscures the viewer's face. Similarly, a viewer's hair or hair covering can present artifacts by obscuring the viewer's eyes and/or face.

The captured facial data can be analyzed using the facial action coding system (FACS). The FACS seeks to define groups or taxonomies of facial movements of the human face. The FACS encodes movements of individual muscles of the face, where the muscle movements often include slight, instantaneous changes in facial appearance. The FACS encoding is commonly performed by trained observers, but can also be performed on automated, computer-based systems. Analysis of the FACS encoding can be used to determine emotions of the persons whose facial data is captured in the videos. The FACS is used to encode a wide range of facial expressions that are anatomically possible for the human face. The FACS encodings include action units (AUs) and related temporal segments that are based on the captured facial expression. The AUs are open to higher order interpretation and decision-making. These AUs can be used to recognize emotions experienced by the person who is being observed. Emotion-related facial actions can be identified using the emotional facial action coding system (EM-FACS) and the facial action coding system affect interpretation dictionary (FACSAID). For a given emotion, specific action units can be related to the emotion. For example, the emotion of anger can be related to AUs 4, 5, 7, and 23, while happiness can be related to AUs 6 and 12. Other mappings of emotions to AUs have also been previously associated.

The coding of the AUs can include an intensity scoring that ranges from A (trace) to E (maximum). The AUs can be used for analyzing images to identify patterns indicative of a particular cognitive and/or emotional state. The AUs range in number from 0 (neutral face) to 98 (fast up-down look). The AUs include so-called main codes (inner brow raiser, lid tightener, etc.), head movement codes (head turn left, head up, etc.), eye movement codes (eyes turned left, eyes up, etc.), visibility codes (eyes not visible, entire face not visible, etc.), and gross behavior codes (sniff, swallow, etc.). Emotion scoring can be included where intensity is evaluated, and specific emotions, moods, mental states, or cognitive states can be identified.

The coding of faces identified in videos captured of people observing an event can be automated. The automated systems can detect facial AUs or discrete emotional states. The emotional states can include amusement, fear, anger, disgust, surprise, and sadness. The automated systems can be based on a probability estimate from one or more classifiers, where the probabilities can correlate with an intensity of an AU or an expression. The classifiers can be used to identify into which of a set of categories a given observation can be placed. In some cases, the classifiers can be used to determine a probability that a given AU or expression is present in a given frame of a video. The classifiers can be used as part of a supervised machine learning technique, where the machine learning technique can be trained using "known good" data. Once trained, the machine learning technique can proceed to classify new data that is captured.

The supervised machine learning models can be based on support vector machines (SVMs). An SVM can have an associated learning model that is used for data analysis and pattern analysis. For example, an SVM can be used to classify data that can be obtained from collected videos of people experiencing a media presentation. An SVM can be trained using "known good" data that is labeled as belonging to one of two categories (e.g. smile and no-smile). The SVM can build a model that assigns new data into one of the two categories. The SVM can construct one or more hyperplanes that can be used for classification. The hyperplane that has the largest distance from the nearest training point can be determined to have the best separation. The largest separation can improve the classification technique by increasing the probability that a given data point can be properly classified.

In another example, a histogram of oriented gradients (HoG) can be computed. The HoG can include feature descriptors and can be computed for one or more facial regions of interest. The regions of interest of the face can be located using facial landmark points, where the facial landmark points can include outer edges of nostrils, outer edges of the mouth, outer edges of eyes, etc. A HoG for a given region of interest can count occurrences of gradient orientation within a given section of a frame from a video, for example. The gradients can be intensity gradients and can be used to describe an appearance and a shape of a local object. The HoG descriptors can be determined by dividing an image into small, connected regions, also called cells. A histogram of gradient directions or edge orientations can be computed for pixels in the cell. Histograms can be contrast-normalized based on intensity across a portion of the image or the entire image, thus reducing any influence from differences in illumination or shadowing changes between and among video frames. The HoG can be computed on the image or on an adjusted version of the image, where the adjustment of the image can include scaling, rotation, etc. The image can be adjusted by flipping the image around a vertical line through the middle of a face in the image. The symmetry plane of the image can be determined from the tracker points and landmarks of the image.

In embodiments, an automated facial analysis system identifies five facial actions or action combinations in order to detect spontaneous facial expressions for media research purposes. Based on the facial expressions that are detected, a determination can be made with regard to the effectiveness of a given video media presentation, for example. The system can detect the presence of the AUs or the combination of AUs in videos collected from a plurality of people. The facial analysis technique can be trained using a web-based framework to crowdsource videos of people as they watch online video content. The video can be streamed at a fixed frame rate to a server. Human labelers can code for the presence or absence of facial actions including a symmetric smile, unilateral smile, asymmetric smile, and so on. The trained system can then be used to automatically code the facial data collected from a plurality of viewers experiencing video presentations (e.g. television programs).

Spontaneous asymmetric smiles can be detected in order to understand viewer experiences. Related literature indicates that as many asymmetric smiles occur on the right hemi face as do on the left hemi face, for spontaneous expressions. Detection can be treated as a binary classification problem, where images that contain a right asymmetric expression are used as positive (target class) samples and all other images as negative (non-target class) samples. Classifiers perform the classification, including classifiers such as support vector machines (SVM) and random forests. Random forests can include ensemble-learning methods that use multiple learning algorithms to obtain better predictive performance. Frame-by-frame detection can be performed to recognize the presence of an asymmetric expression in each frame of a video. Facial points can be detected, including the top of the mouth and the two outer eye corners. The face can be extracted, cropped and warped into a pixel image of specific dimension (e.g. 96×96 pixels). In embodiments, the inter-ocular distance and vertical scale in the pixel image are fixed. Feature extraction can be performed using computer vision software such as OpenCV™. Feature extraction can be based on the use of HoGs. HoGs can include feature descriptors and can be used to count occurrences of gradient orientation in localized portions or regions of the image. Other techniques can be used for counting occurrences of gradient orientation, including edge orientation histograms, scale-invariant feature transformation descriptors, etc. The AU recognition tasks can also be performed using Local Binary Patterns (LBP) and Local Gabor Binary Patterns (LGBP). The HoG descriptor represents the face as a distribution of intensity gradients and edge directions and is robust in its ability to translate and scale. Differing patterns, including groupings of cells of various sizes and arranged in variously sized cell blocks, can be used. For example, 4×4 cell blocks of 8×8-pixel cells with an overlap of half of the block can be used. Histograms of channels can be used, including nine channels or bins evenly spread over 0-180 degrees. In this example, the HoG descriptor on a 96×96 image is 25 blocks×16 cells×9 bins=3600, the latter quantity representing the dimension. AU occurrences can be rendered. The videos can be grouped into demographic datasets based on nationality and/or other demographic parameters for further detailed analysis. This grouping and other analyses can be facilitated via semiconductor-based logic.

Figure 13:
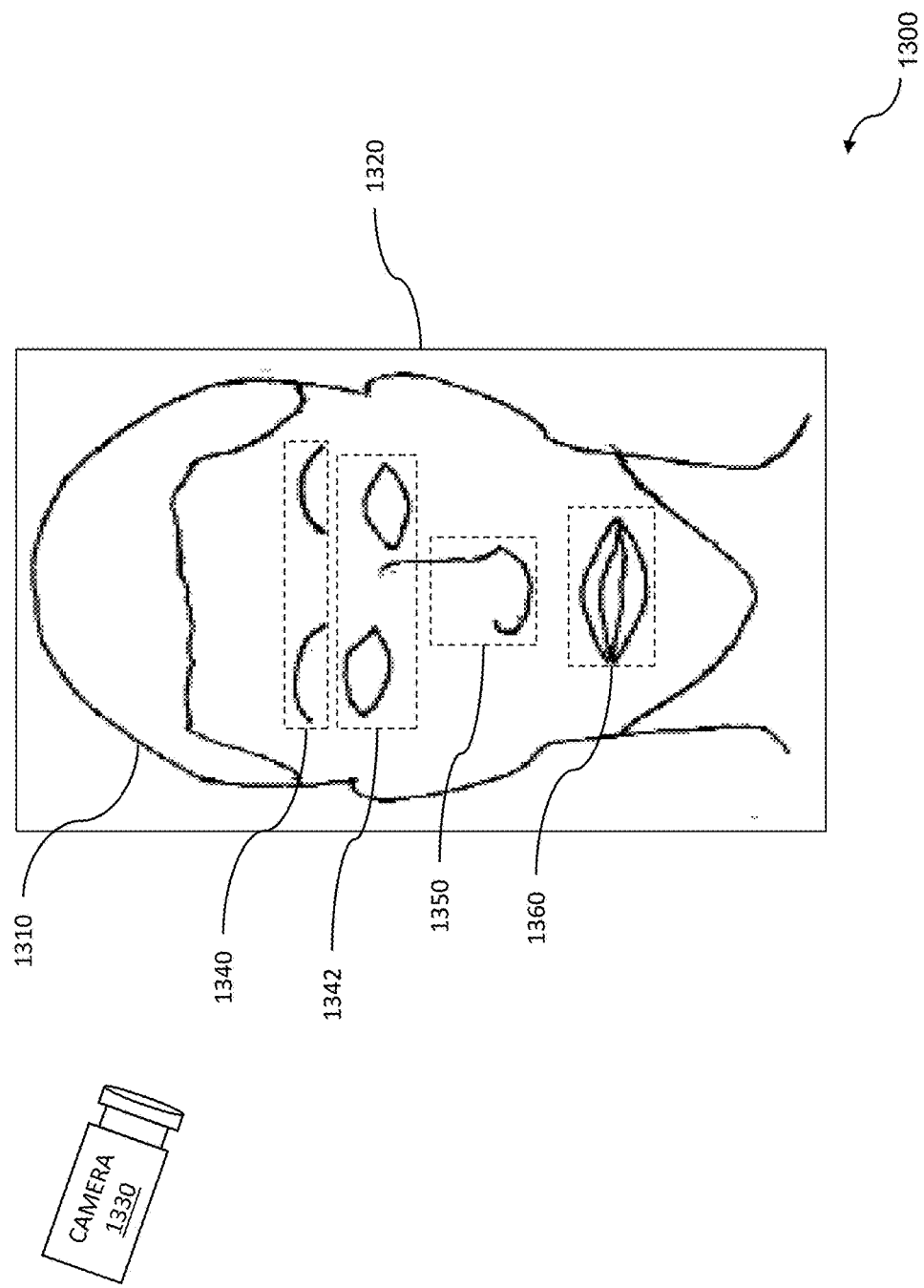
FIG. 13 shows example facial data collection including regions.

FIG. 13 shows example facial data collection including regions. The collecting of facial data including regions can be performed for image analysis for a two-sided data hub. Data received by an individual and a content provider is enabled. The enabling can be accomplished using a cognitive reaction data hub. Cognitive state data, which can include facial data, is collected on the individual. Processors are used for analyzing the cognitive state data and further for providing analysis of the cognitive state data to the individual. The cognitive state data is evaluated and the results are provided to the content provider. The facial data including regions can be collected from people as they interact with the Internet. Various regions of a face can be identified and used for a variety of purposes including facial recognition, facial analysis, and so on. Facial analysis can be used to determine, predict, estimate, etc. cognitive states, emotions, and so on of a person from whom facial data can be collected. The one or more emotions that can be determined by the analysis can be represented by an image, a figure, an icon, etc. The representative icon can include an emoji. One or more emoji can be used to represent a cognitive state, a mood, etc. of an individual, to represent food, a geographic location, weather, and so on. The emoji can include a static image. The static image can be a predefined size such as a certain number of pixels. The emoji can include an animated image. The emoji can be based on a GIF or another animation standard. The emoji can include a cartoon representation. The cartoon representation can be any cartoon type, format, etc. that can be appropriate to representing an emoji.

In the example 1300, facial data can be collected, where the facial data can include regions of a face. The facial data that is collected can be based on sub-sectional components of a population. When more than one face can be detected in an image, facial data can be collected for one face, some faces, all faces, and so on. The facial data which can include facial regions can be collected using any of a variety of electronic hardware and software techniques. The facial data can be collected using sensors including motion sensors, infrared sensors, physiological sensors, imaging sensors, and so on. A face 1310 can be observed using a camera 1330, a sensor, a combination of cameras and/or sensors, and so on. The camera 1330 can be used to collect facial data that can be used to determine if a face is present in an image. When a face is present in an image, a bounding box 1320 can be placed around the face. Placement of the bounding box around the face can be based on detection of facial landmarks. The camera 1330 can be used to collect from the bounding box 1320 facial data, where the facial data can include facial regions. The facial data can be collected from a plurality of people using any of a variety of cameras. As discussed previously, the camera or cameras can include a webcam, where a webcam can include a video camera, a still camera, a thermal imager, a CCD device, a smartphone camera, a three-dimensional camera, a depth camera, a light field camera, multiple webcams used to show different views of a person, or any other type of image capture apparatus that can allow captured data to be used in an electronic system. As discussed previously, the quality and usefulness of the facial data that is captured can depend on, among other examples, the position of the camera 1330 relative to the face 1310, the number of cameras and/or sensors used, the illumination of the face, any obstructions to viewing the face, and so on.

The facial regions that can be collected by the camera 1330, sensor, or combination of cameras and/or sensors can include any of a variety of facial features. The facial features that can be included in the facial regions that are collected can include eyebrows 1340, eyes 1342, a nose 1350, a mouth 1360, ears, hair, texture, tone, and so on. Multiple facial features can be included in one or more facial regions. The number of facial features that can be included in the facial regions can depend on the desired amount of data to be captured, whether a face is in profile, whether the face is partially occluded or obstructed, etc. The facial regions that can include one or more facial features can be analyzed to determine facial expressions. The analysis of the facial regions can also include determining probabilities of occurrence of one or more facial expressions. The facial features that can be analyzed can also include textures, gradients, colors, shapes, etc. The facial features can be used to determine demographic data, where the demographic data can include age, ethnicity, culture, gender, etc. Multiple textures, gradients, colors, shapes, and so on, can be detected by the camera 1330, sensor, or combination of cameras and sensors. Texture, brightness, and color, for example, can be used to detect boundaries in an image for detection of a face, facial features, facial landmarks, and so on.

A texture in a facial region can include facial characteristics, skin types, and so on. In some instances, a texture in a facial region can include smile lines, crow's feet, wrinkles, and so on. Another texture that can be used to evaluate a facial region can include a smooth portion of skin such as a smooth portion of a check. A gradient in a facial region can include values assigned to local skin texture, shading, etc. A gradient can be used to encode, for example, a texture, by computing magnitudes in a local neighborhood or portion of an image. The computed values can be compared to discrimination levels, threshold values, and so on. The gradient can be used to determine gender, facial expression, etc. A color in a facial region can include eye color, skin color, hair color, and so on. A color can be used to determine demographic data, where the demographic data can include ethnicity, culture, age, gender, etc. A shape in a facial region can include shape of a face, eyes, nose, mouth, ears, and so on. As with color in a facial region, shape in a facial region can be used to determine demographic data including ethnicity, culture, age, gender, and so on.

The facial regions can be detected based on edges, boundaries, and so on, of features that can be included in an image. The detection can be based on various types of analysis of the image. The features in the image can include one or more faces. A boundary can refer to a contour in an image plane where the contour can represent ownership of a particular picture element (pixel) from one object, feature, etc. in the image, to another object, feature, and so on, in the image. An edge can be a distinct, low-level change of one or more features in an image. That is, an edge can be detected based on a change, including an abrupt change, in color, brightness, etc. within an image. In embodiments, image classifiers are used for the analysis. The image classifiers can include algorithms, heuristics, and so on, and can be implemented using functions, classes, subroutines, code segments, etc. The classifiers can be used to detect facial regions, facial features, and so on. As discussed above, the classifiers can be used to detect textures, gradients, color, shapes, edges, etc. Any classifier can be used for the analysis, including, but not limited to, density estimation, support vector machines (SVM), logistic regression, classification trees, and so on. By way of example, consider facial features that can include the eyebrows 1340. One or more classifiers can be used to analyze the facial regions that can include the eyebrows to determine a probability for either a presence or an absence of an eyebrow furrow. The probability can include a posterior probability, a conditional probability, and so on. The probabilities can be based on Bayesian Statistics or another statistical analysis technique.

The presence of an eyebrow furrow can indicate the person from whom the facial data can be collected is annoyed, confused, unhappy, and so on. In another example, consider facial features that can include a mouth 1346. One or more classifiers can be used to analyze the facial region that can include the mouth to determine a probability for either a presence or an absence of mouth edges turned up to form a smile. Multiple classifiers can be used to determine one or more facial expressions.

Figure 14:
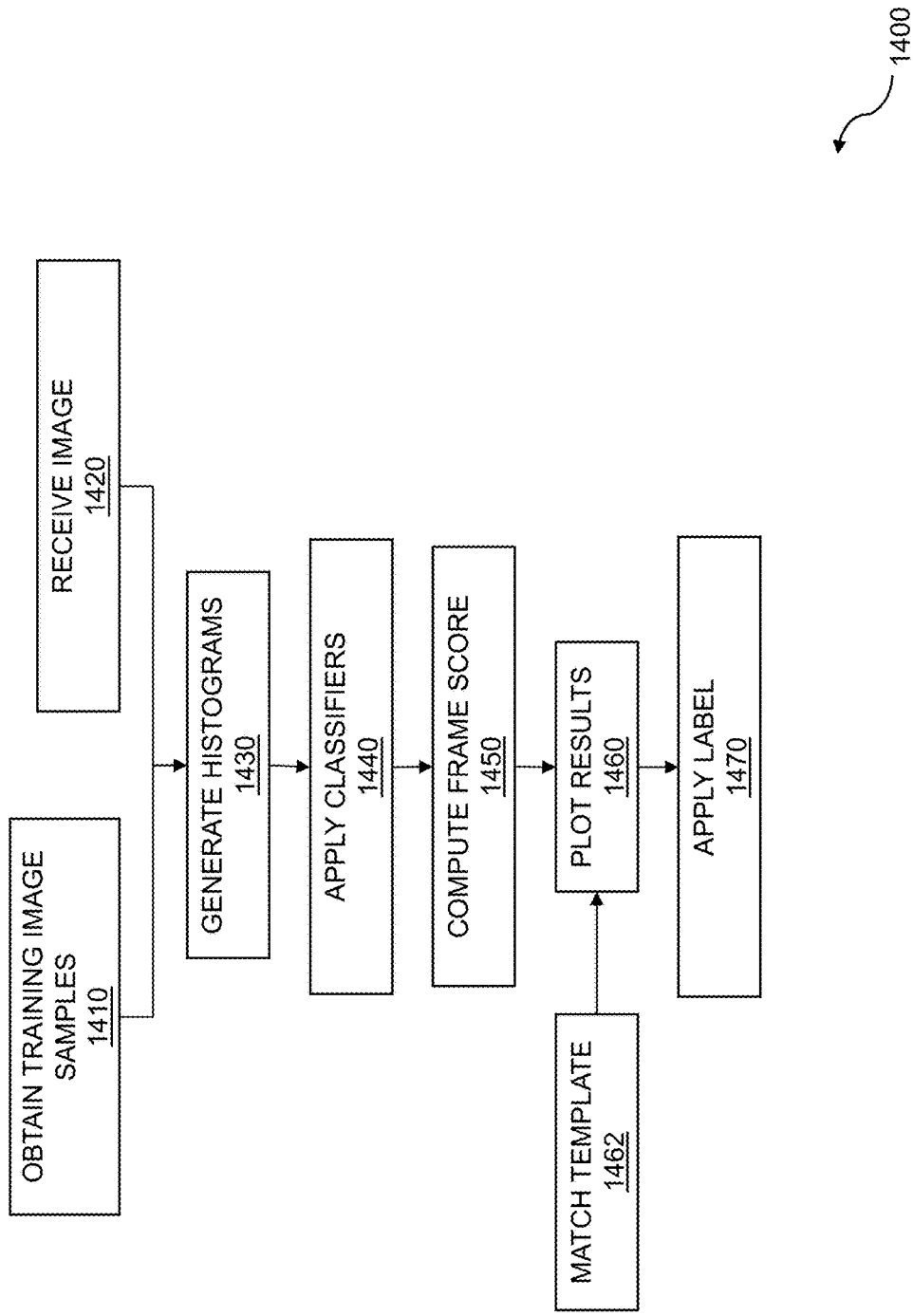
FIG. 14 is a flow diagram for detecting facial expressions.

FIG. 14 is a flow diagram for detecting facial expressions. Cognitive states can be determined by detecting and analyzing facial expressions in images. The cognitive states can be used for image processing for a two-sided data hub. An individual and a content provider enable data reception. Cognitive state data including facial data is collected on the individual. The cognitive state data is analyzed and the results are provided to the individual. The cognitive state data is evaluated and the results are provided to the content provider. A mood dashboard is displayed to the individual based on the analyzing. The flow 1400, or portions thereof, can be implemented in semiconductor logic, can be accomplished using a mobile device, can be accomplished using a server device, and so on. The flow 1400 can be used to automatically detect a wide range of facial expressions. A facial expression can produce strong emotional signals that can indicate valence and discrete emotional states. The discrete emotional states can include contempt, doubt, defiance, happiness, fear, anxiety, and so on. The detection of facial expressions can be based on the location of facial landmarks. The detection of facial expressions can be based on determination of action units (AU), where the action units are determined using FACS coding. The AUs can be used separately or in combination to identify facial expressions. Based on the facial landmarks, one or more AUs can be identified by number and intensity. For example, AU12 can be used to code a lip corner puller and can be used to infer a smirk.

The flow 1400 begins by obtaining training image samples 1410. The image samples can include a plurality of images of one or more people. Human coders who are trained to correctly identify AU codes based on the FACS can code the images. The training or "known good" images can be used as a basis for training a machine learning technique. Once trained, the machine learning technique can be used to identify AUs in other images that can be collected using a camera, a sensor, and so on. The flow 1400 continues with receiving an image 1420. The image 1420 can be received from a camera, a sensor, and so on. As previously discussed, the camera or cameras can include a webcam, where a webcam can include a video camera, a still camera, a thermal imager, a CCD device, a phone camera, a three-dimensional camera, a depth camera, a light field camera, multiple webcams used to show different views of a person, or any other type of image capture apparatus that can allow captured data to be used in an electronic system. The image that is received can be manipulated in order to improve the processing of the image. For example, the image can be cropped, scaled, stretched, rotated, flipped, etc. in order to obtain a resulting image that can be analyzed more efficiently. Multiple versions of the same image can be analyzed. In some cases, the manipulated image and a flipped or mirrored version of the manipulated image can be analyzed alone and/or in combination to improve analysis. The flow 1400 continues with generating histograms 1430 for the training images and the one or more versions of the received image. The histograms can be based on a HoG or another histogram. As described in previous paragraphs, the HoG can include feature descriptors and can be computed for one or more regions of interest in the training images and the one or more received images. The regions of interest in the images can be located using facial landmark points, where the facial landmark points can include outer edges of nostrils, outer edges of the mouth, outer edges of eyes, etc. A HoG for a given region of interest can count occurrences of gradient orientation within a given section of a frame from a video.

The flow 1400 continues with applying classifiers 1440 to the histograms. The classifiers can be used to estimate probabilities, where the probabilities can correlate with an intensity of an AU or an expression. In some embodiments, the choice of classifiers used is based on the training of a supervised learning technique to identify facial expressions. The classifiers can be used to identify into which of a set of categories a given observation can be placed. The classifiers can be used to determine a probability that a given AU or expression is present in a given image or frame of a video. In various embodiments, the one or more AUs that are present include AU01 inner brow raiser, AU12 lip corner puller, AU38 nostril dilator, and so on. In practice, the presence or absence of multiple AUs can be determined. The flow 1400 continues with computing a frame score 1450. The score computed for an image, where the image can be a frame from a video, can be used to determine the presence of a facial expression in the image or video frame. The score can be based on one or more versions of the image 1420 or a manipulated image. The score can be based on a comparison of the manipulated image to a flipped or mirrored version of the manipulated image. The score can be used to predict a likelihood that one or more facial expressions are present in the image. The likelihood can be based on computing a difference between the outputs of a classifier used on the manipulated image and on the flipped or mirrored image, for example. The classifier that is used can be used to identify symmetrical facial expressions (e.g. smile), asymmetrical facial expressions (e.g. outer brow raiser), and so on.

The flow 1400 continues with plotting results 1460. The results that are plotted can include one or more scores for one or more frames computed over a given time t. For example, the plotted results can include classifier probability results from analysis of HoGs for a sequence of images and video frames. The plotted results can be matched with a template 1462. The template can be temporal and can be represented by a centered box function or another function. A best fit with one or more templates can be found by computing a minimum error. Other best-fit techniques can include polynomial curve fitting, geometric curve fitting, and so on. The flow 1400 continues with applying a label 1470. The label can be used to indicate that a particular facial expression has been detected in the one or more images or video frames which constitute the image that was received 1420. The label can be used to indicate that any of a range of facial expressions has been detected, including a smile, an asymmetric smile, a frown, and so on. Various steps in the flow 1400 may be changed in order, repeated, omitted, or the like without departing from the disclosed concepts. Various embodiments of the flow 1400 can be included in a computer program product embodied in a non-transitory computer readable medium that includes code executable by one or more processors. Various embodiments of the flow 1400, or portions thereof, can be included on a semiconductor chip and implemented in special purpose logic, programmable logic, and so on.

Figure 15:
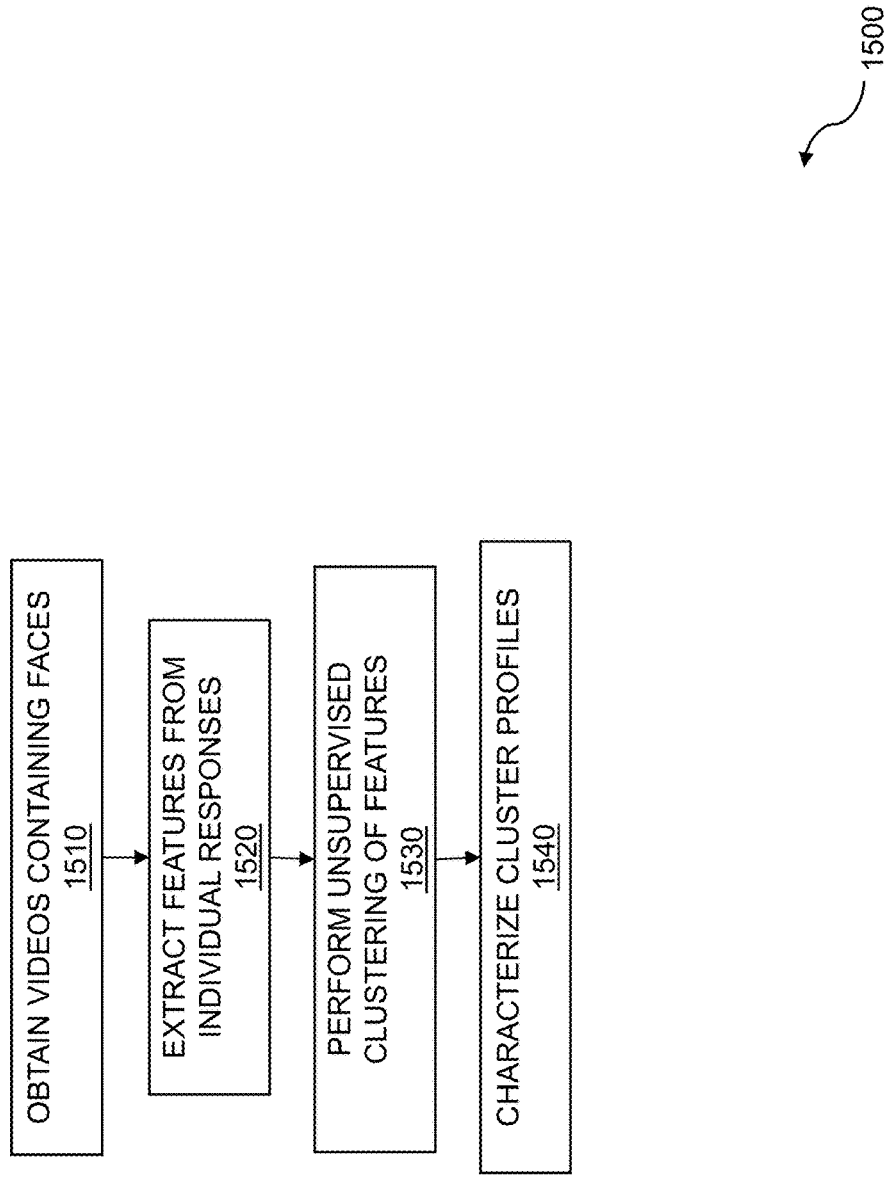
FIG. 15 is a flow diagram for the large-scale clustering of facial events.

FIG. 15 is a flow diagram for the large-scale clustering of facial events. Cognitive state data including facial data can be collected for image analysis. Facial events can be determined based on image analysis, where the facial events can be used by a two-sided data hub. Data reception is enabled by an individual and a content provider. Cognitive state data including facial data is collected on the individual. Analysis of the cognitive state data can be provided to the individual, and evaluation of the cognitive state data can be provided to the content provider. A mood dashboard can be displayed to the individual.

Cognitive state events can include facial events, speech events, etc. The large-scale clustering of facial events can be performed for data collected from a remote computing device. The facial events can be collected from people as they interact with a vehicle. The clustering and evaluation of facial events can be augmented using a mobile device, a server, semiconductor-based logic, and so on. As discussed above, collection of facial video data from one or more people can include a web-based framework. The web-based framework can be used to collect facial video data from large numbers of people located over a wide geographic area. The web-based framework can include an opt-in feature that allows people to agree to facial data collection. The web-based framework can be used to render and display data to one or more people and can collect data from the one or more people. For example, the facial data collection can be based on showing one or more viewers a video media presentation through a website. The web-based framework can be used to display the video media presentation or event and to collect videos from multiple viewers who are online. That is, the collection of videos can be crowdsourced from those viewers who elected to opt-in to the video data collection. The video event can be a commercial, a political ad, an educational segment, and so on.

The flow 1500 includes obtaining videos containing faces 1510. The videos can be obtained using one or more cameras, where the cameras can include a webcam coupled to one or more devices employed by the one or more people using the web-based framework. The flow 1500 continues with extracting features from the individual responses 1520. The individual responses can include videos containing faces observed by the one or more webcams. The features that are extracted can include facial features such as an eyebrow, a nostril, an eye edge, a mouth edge, and so on. The feature extraction can be based on facial coding classifiers, where the facial coding classifiers output a probability that a specified facial action has been detected in a given video frame. The flow 1500 continues with performing unsupervised clustering of features 1530. The unsupervised clustering can be based on an event. The unsupervised clustering can be based on a K-Means, where the K of the K-Means can be computed using a Bayesian Information Criterion (BICk), for example, to determine the smallest value of K that meets system requirements. Any other criterion for K can be used. The K-Means clustering technique can be used to group one or more events into various respective categories.

The flow 1500 includes characterizing cluster profiles 1540. The profiles can include a variety of facial expressions such as smiles, asymmetric smiles, eyebrow raisers, eyebrow lowerers, etc. The profiles can be related to a given event. For example, a humorous video can be displayed in the web-based framework and the video data of people who have opted-in can be collected. The characterization of the collected and analyzed video can depend in part on the number of smiles that occurred at various points throughout the humorous video. Similarly, the characterization can be performed on collected and analyzed videos of people viewing a news presentation. The characterized cluster profiles can be further analyzed based on demographic data. The number of smiles resulting from people viewing a humorous video can be compared across various demographic groups, where the groups can be formed based on geographic location, age, ethnicity, gender, and so on.

The flow 1500 can include determining cognitive state event temporal signatures. The cognitive state event temporal signatures can include information on rise time to facial expression intensity, fall time from facial expression intensity, duration of a facial expression, and so on. In some embodiments, the cognitive state event temporal signatures are associated with certain demographics, ethnicities, cultures, etc. The cognitive state event temporal signatures can be used to identify one or more of sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, depression, envy, sympathy, embarrassment, poignancy, or mirth. Various steps in the flow 1500 may be changed in order, repeated, omitted, or the like without departing from the disclosed concepts. Various embodiments of the flow 1500 can be included in a computer program product embodied in a non-transitory computer readable medium that includes code executable by one or more processors. Various embodiments of the flow 1500, or portions thereof, can be included on a semiconductor chip and implemented in special purpose logic, programmable logic, and so on.

Figure 16A:
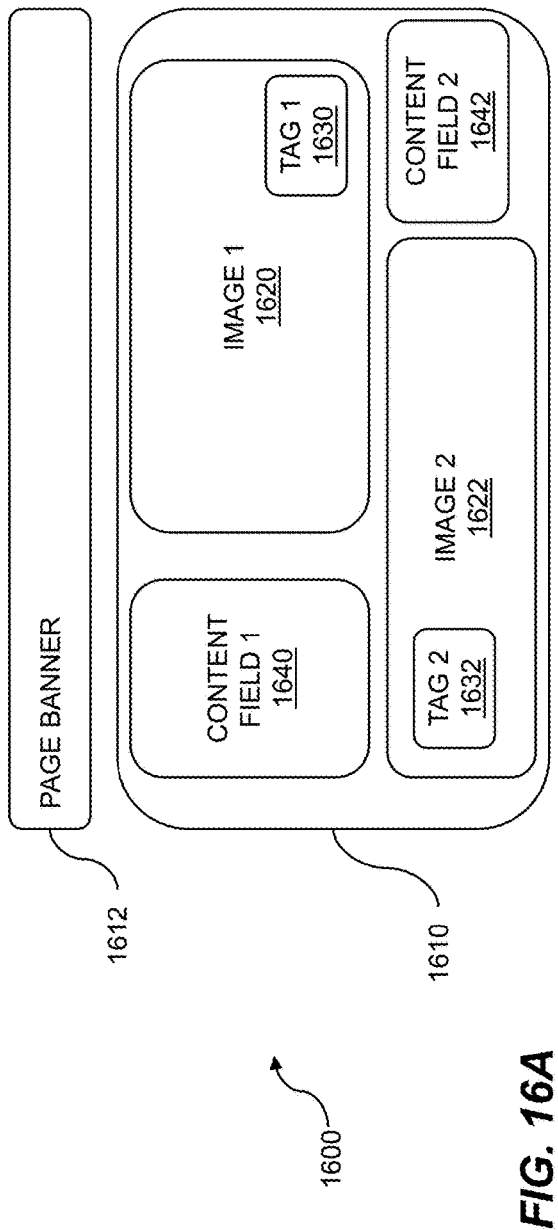
FIG. 16A shows example tags embedded in a webpage.

FIG. 16A shows example tags embedded in a webpage. Tags embedded in a webpage such as a mood dashboard can be used to enable image collection. The images can be analyzed for a two-sided data hub. In some embodiments, screens coupled to a computing device used by an individual can employ embedded tags. Data reception is enabled by both an individual and a content provider. Cognitive state data including facial data is collected on the individual. The cognitive state data is analyzed and the results are provided to the individual. The cognitive state data is evaluated and the results are provided to the content provider.

The tags embedded in the webpage can be used for image analysis for data collected from a remote computing device. The tags embedded in the webpage can be used by people as they interact with a vehicle. Once a tag is detected, a mobile device, a server, semiconductor-based logic, etc. can be used to evaluate associated facial expressions. A webpage 1600 can include a page body 1610, a page banner 1612, and so on. The page body can include one or more objects, where the objects can include text, images, videos, audio, and so on. The example page body 1610 shown includes a first image, image 1 1620; a second image, image 2 1622; a first content field, content field 1 1640; and a second content field, content field 2 1642. In practice, the page body 1610 can contain multiple images and content fields and can include one or more videos, one or more audio presentations, and so on. The page body can include embedded tags, such as tag 1 1630 and tag 2 1632. In the example shown, tag 1 1630 is embedded in image 1 1620, and tag 2 1632 is embedded in image 2 1622. In embodiments, multiple tags are embedded. Tags can also be embedded in content fields, in videos, in audio presentations, etc. When a user mouses over a tag or clicks on an object associated with a tag, the tag can be invoked. For example, when the user mouses over tag 1 1630, tag 1 1630 can then be invoked. Invoking tag 1

1630 can include enabling a camera coupled to a user's device and capturing one or more images of the user as the user views a media presentation (or digital experience). In a similar manner, when the user mouses over tag 2 1632, tag 2 1632 can be invoked. Invoking tag 2 1632 can also include enabling the camera and capturing images of the user. In other embodiments, other actions are taken based on invocation of the one or more tags. Invoking an embedded tag can initiate an analysis technique, post to social media, award the user a coupon or another prize, initiate cognitive state analysis, perform emotion analysis, and so on.

Figure 16B:
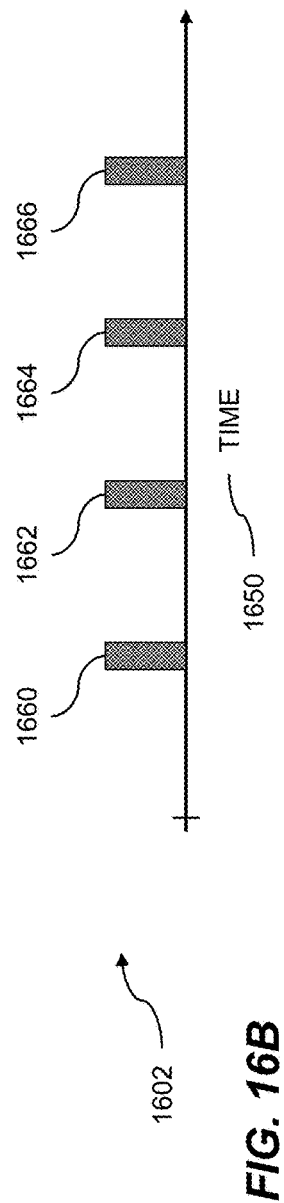
FIG. 16B shows invoking tags to collect images.

FIG. 16B shows invoking tags to collect images. The invoking tags to collect images can be used for image analysis for a two-sided data hub. The invoking tags to collect images can be used for people as they interact with various content provided to them, including content provided over a computer network such as the Internet. The tags can be related to analysis of cognitive state data for an individual and for evaluating cognitive state data based on content provided by a content provider. A mood dashboard can be displayed to the individual based on the analyzing. The content provider can provide content via a website.

As previously stated, a media presentation can be a video, a webpage, and so on. A video 1602 can include one or more embedded tags, such as a tag 1660, another tag 1662, a third tag 1664, a fourth tag 1666, and so on. In practice, multiple tags can be included in the media presentation. The one or more tags can be invoked during the media presentation. The collection of the invoked tags can occur over time, as represented by a timeline 1650. When a tag is encountered in the media presentation, the tag can be invoked. When the tag 1660 is encountered, invoking the tag can enable a camera coupled to a user device and can capture one or more images of the user viewing the media presentation. Invoking a tag can depend on agreement to opt-in by the user. For example, if a user has agreed to participate in a study by indicating an opt-in, then the camera coupled to the user's device can be enabled and one or more images of the user can be captured. If the user has not agreed to participate in the study and has not indicated an opt-in, then invoking the tag 1660 does not enable the camera nor capture images of the user during the media presentation. The user can indicate an opt-in for certain types of participation, where opting-in can be dependent on specific content in the media presentation. The user could opt-in to participate in a study of political campaign messages and not opt-in for a particular advertisement study. In this case, tags that are related to political campaign messages, advertising messages, social media sharing, etc. and that enable the camera and image capture when invoked would be embedded in the media presentation social media sharing, and so on. However, tags embedded in the media presentation that are related to advertisements would not enable the camera when invoked. Various other situations of tag invocation are possible.

The capturing of images, videos, frames from video, audio, etc. of one or more individuals results in substantial quantities of data that is stored for analysis, evaluation, comparison, aggregation, and other purposes. The image and video quality can vary depending on the capabilities of the machine or electronic device that is gathering the image and video data. The video quality can include 15 frames per second (fps), 30 fps, and so on. The data that is received by the one or more individuals, such as content provided by a content provider and delivered over the Internet from a website rendered for the one or more individuals, can also be stored. Further, keystrokes, mouse clicks, invoking tags, and other directed and automatic user actions result in additional data. The result of the capturing of video data, content, user web journey information, and so on is that the volume of data increases over time.

The data, such as the video data collected from an individual, includes cognitive state data, facial data, and so on. The cognitive state data from the one or more individuals can be analyzed to determine one or more moods, one or more cognitive states, one or more emotional states, etc., for the one or more individuals. The purposes of the analysis can vary and can include determining whether a website, web content, and so on makes a given individual happy, sad, angry, and so on. Such analysis can compare recently collected data to data collected in the past, where the past can be earlier in the day, a previous day, an earlier week, last year, etc. This "data telescoping" can be useful to both the individual consumer of web content and to the content provider of the web and other content. The data telescoping can be used to recommend and/or direct an individual to a website that makes her or him happy, to avoid websites that induce anger, and so on. Additionally, the data telescoping can be used by a content provider to send to an individual content in which that individual demonstrates interest, to not send content that makes the individual angry, etc.

The value of the stored data changes over time. Current data can have the highest value and relevance and can be stored in its entirety at a micro level. As the data ages, the typical trend is for the data to become less useful for such actions as predicting a current cognitive or emotional state in an individual, determining which content to provide, and so on. Various techniques can be used to determine what to do with the aging data. For example, after a week, the cognitive state data for an individual may be less relevant for determining current cognitive or emotional state, but can still maintain relevance for making comparisons of moods, emotions, cognitive states, determining trends, and so on. Over time, the data can be aggregated to time intervals. Such time intervals can include aggregating to one second intervals after a week, aggregating to the minute after a month, aggregating to an hour after a year, etc. The aggregation of data can be based on different techniques. One technique for data aggregation can include overall levels identified in the data such as whether the individual is happier, angrier, more confused, etc., when visiting a website or other content conduit. Another technique for data aggregation can include events such as numbers of smiles, eyebrow raises, scowls, etc. Aggregation of the data can also be based on filters used to identify data that should be kept, and other data that should be discarded.

The techniques used for the storage of the data are based on cost of storage, convenience of storage, uses of the data, and so on. Such data "warehousing" typically supports multiple uses of the data. A content provider may want to know the current cognitive and emotional states of an individual in order to provide that individual with content that will make the individual happy. The data storage accessed by the content provider would be fast and "nearby" for ready access immediately. By comparison, data scientists studying the collected data may be satisfied with slower, "farther away" storage. This latter class of storage provides for more inexpensive storage of larger quantities of data than does the former class of storage.

Figure 17:
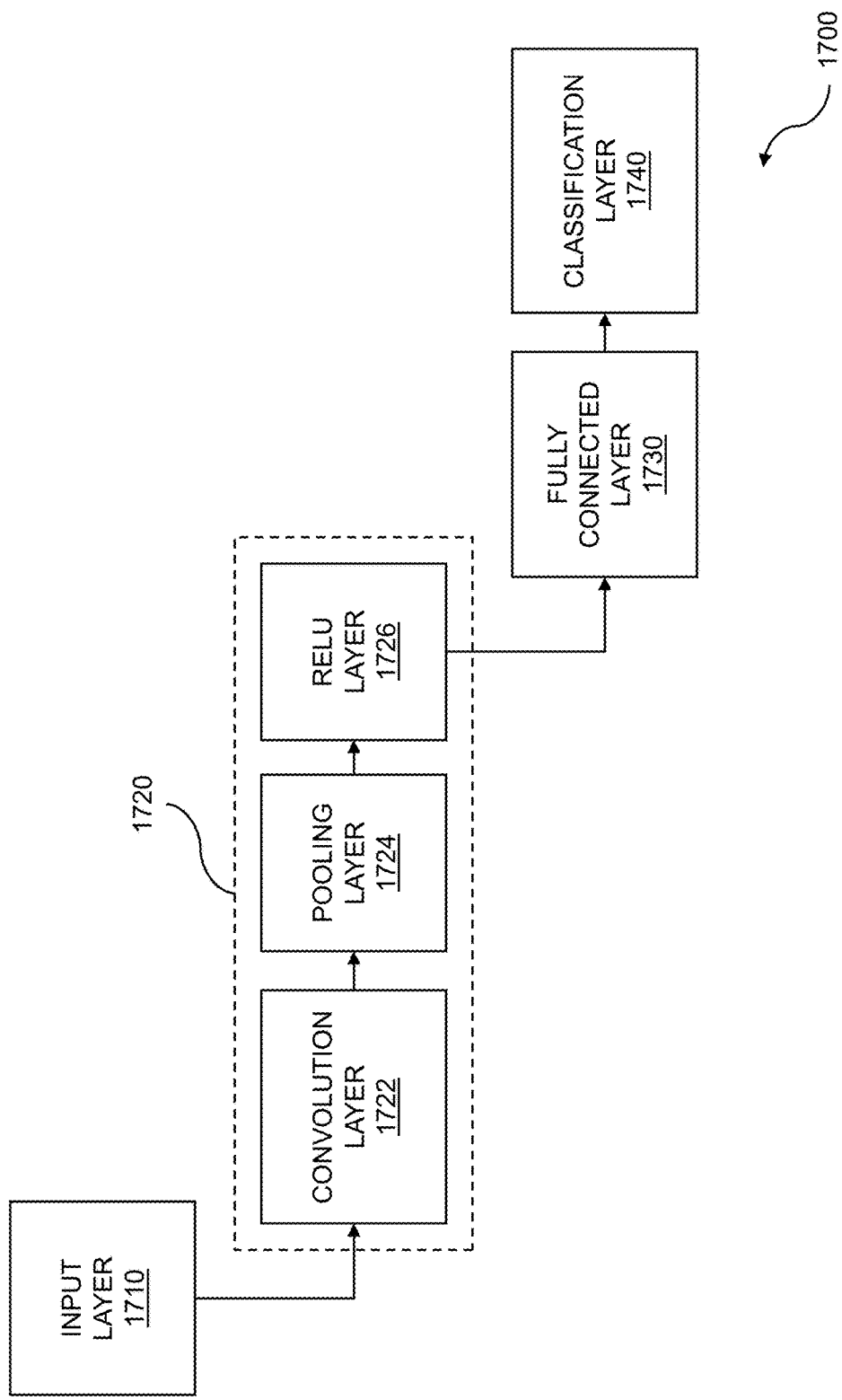
FIG. 17 is an example showing a convolutional neural network.

FIG. 17 is an example showing a convolutional neural network (CNN). The convolutional neural network can be used for deep learning, where the deep learning can be applied to image analysis for two-sided data hub. Data reception is enabled by both an individual and a content provider. Cognitive state data including facial data is collected on the individual. The cognitive state data is analyzed and the results are provided to the individual. The cognitive state data is evaluated and the results are provided to the content provider. The convolutional neural network can be applied to such tasks as cognitive state analysis, mental state analysis, mood analysis, emotional state analysis, and so on. Cognitive state data can include mental processes, where the mental processes can include attention, creativity, memory, perception, problem solving, thinking, use of language, or the like.

Cognitive analysis is a very complex task. Understanding and evaluating moods, emotions, mental states, or cognitive states, require a nuanced evaluation of facial expressions or other cues generated by people. Cognitive state analysis is important in many areas such as research, psychology, business, intelligence, law enforcement, and so on. The understanding of cognitive states can be useful for a variety of business purposes, such as improving marketing analysis, assessing the effectiveness of customer service interactions and retail experiences, and evaluating the consumption of content such as movies and videos. Identifying points of frustration in a customer transaction can allow a company to take action to address the causes of the frustration. By streamlining processes, key performance areas such as customer satisfaction and customer transaction throughput can be improved, resulting in increased sales and revenues. In a content scenario, producing compelling content that achieves the desired effect (e.g. fear, shock, laughter, etc.) can result in increased ticket sales and/or increased advertising revenue. If a movie studio is producing a horror movie, it is desirable to know if the scary scenes in the movie are achieving the desired effect. By conducting tests in sample audiences, and analyzing faces in the audience, a computer-implemented method and system can process thousands of faces to assess the cognitive state at the time of the scary scenes. In many ways, such an analysis can be more effective than surveys that ask audience members questions, since audience members may consciously or subconsciously change answers based on peer pressure or other factors. However, spontaneous facial expressions can be more difficult to conceal. Thus, by analyzing facial expressions en masse in real time, important information regarding the general cognitive state of the audience can be obtained.

Analysis of facial expressions is also a complex task. Image data, where the image data can include facial data, can be analyzed to identify a range of facial expressions. The facial expressions can include a smile, frown, smirk, and so on. The image data and facial data can be processed to identify the facial expressions. The processing can include analysis of expression data, action units, gestures, mental states, cognitive states, physiological data, and so on. Facial data as contained in the raw video data can include information on one or more of action units, head gestures, smiles, brow furrows, squints, lowered eyebrows, raised eyebrows, attention, and the like. The action units can be used to identify smiles, frowns, and other facial indicators of expressions. Gestures can also be identified, and can include a head tilt to the side, a forward lean, a smile, a frown, as well as many other gestures. Other types of data including the physiological data can be collected, where the physiological data can be obtained using a camera or other image capture device, without contacting the person or persons. Respiration, heart rate, heart rate variability, perspiration, temperature, and other physiological indicators of cognitive state can be determined by analyzing the images and video data.

Deep learning is a branch of machine learning which seeks to imitate in software the activity which takes place in layers of neurons in the neocortex of the human brain. This imitative activity can enable software to "learn" to recognize and identify patterns in data, where the data can include digital forms of images, sounds, and so on. The deep learning software is used to simulate the large array of neurons of the neocortex. This simulated neocortex, or artificial neural network, can be implemented using mathematical formulas that are evaluated on processors. With the ever-increasing capabilities of the processors, increasing numbers of layers of the artificial neural network can be processed.

Deep learning applications include processing of image data, audio data, and so on. Image data applications include image recognition, facial recognition, etc. Image data applications can include differentiating dogs from cats, identifying different human faces, and the like. The image data applications can include identifying cognitive states, moods, mental states, emotional states, and so on, from the facial expressions of the faces that are identified. Audio data applications can include analyzing audio such as ambient room sounds, physiological sounds such as breathing or coughing, noises made by an individual such as tapping and drumming, voices, and so on. The voice data applications can include analyzing a voice for timbre, prosody, vocal register, vocal resonance, pitch, loudness, speech rate, or language content. The voice data analysis can be used to determine one or more cognitive states, moods, mental states, emotional states, etc.

The artificial neural network, such as a convolutional neural network, which forms the basis for deep learning is based on layers. The layers can include an input layer, a convolution layer, a fully connected layer, a classification layer, and so on. The input layer can receive input data such as image data, where the image data can include a variety of formats including pixel formats. The input layer can then perform processing such as identifying boundaries of the face, identifying landmarks of the face, extracting features of the face, and/or rotating a face within the plurality of images. The convolution layer can represent an artificial neural network such as a convolutional neural network. A convolutional neural network can contain a plurality of hidden layers. A convolutional layer can reduce the amount of data feeding into a fully connected layer. The fully connected layer processes each pixel/data point from the convolutional layer. A last layer within the multiple layers can provide output indicative of cognitive state. The last layer of the convolutional neural network can be the final classification layer. The output of the final classification layer can be indicative of the cognitive states of faces within the images that are provided to the input layer.

Deep networks including deep convolutional neural networks can be used for facial expression parsing. A first layer of the deep network includes multiple nodes, where each node represents a neuron within a neural network. The first layer can receive data from an input layer. The output of the first layer can feed to a second layer, where the latter layer also includes multiple nodes. A weight can be used to adjust the output of the first layer which is being input to the second layer. Some layers in the convolutional neural network can be hidden layers. The output of the second layer can feed to a third layer. The third layer can also include multiple nodes. A weight can adjust the output of the second layer which is being input to the third layer. The third layer may be a hidden layer. Outputs of a given layer can be fed to next layer. Weights adjust the output of one layer as it is fed to the next layer. When the final layer is reached, the output of the final layer can be a facial expression, a cognitive state, a mental state, a characteristic of a voice, and so on. The facial expression can be identified using a hidden layer from the one or more hidden layers. The weights can be provided on inputs to the multiple layers to emphasize certain facial features within the face. The convolutional neural network can be trained to identify facial expressions, voice characteristics, etc. The training can include assigning weights to inputs on one or more layers within the multilayered analysis engine. One or more of the weights can be adjusted or updated during training. The assigning weights can be accomplished during a feed-forward pass through the multilayered neural network. In a feed-forward arrangement, the information moves forward from the input nodes, through the hidden nodes, and on to the output nodes. Additionally, the weights can be updated during a backpropagation process through the multilayered analysis engine.

Returning to the figure, FIG. 17 is an example showing a convolutional neural network 1700. The convolutional neural network can be used for deep learning, where the deep learning can be applied to avatar image animation using translation vectors. The deep learning system can be accomplished using a convolution neural network or other techniques. The deep learning can accomplish facial recognition and analysis tasks. The network includes an input layer 1710. The input layer 1710 receives image data. The image data can be input in a variety of formats, such as JPEG, TIFF, BMP, and GIF. Compressed image formats can be decompressed into arrays of pixels, wherein each pixel can include an RGB tuple. The input layer 1710 can then perform processing such as identifying boundaries of the face, identifying landmarks of the face, extracting features of the face, and/or rotating a face within the plurality of images.

The network includes a collection of intermediate layers 1720. The multilayered analysis engine can include a convolutional neural network. Thus, the intermediate layers can include a convolution layer 1722. The convolution layer 1722 can include multiple sublayers, including hidden layers. The output of the convolution layer 1722 feeds into a pooling layer 1724. The pooling layer 1724 performs a data reduction, which makes the overall computation more efficient. Thus, the pooling layer reduces the spatial size of the image representation to reduce the number of parameters and computations in the network. In some embodiments, the pooling layer is implemented using filters of size 2×2, applied with a stride of two samples for every depth slice along both width and height, resulting in a reduction of 75-percent of the downstream node activations. The multilayered analysis engine can further include a max pooling layer. Thus, in embodiments, the pooling layer 1724 is a max pooling layer, in which the output of the filters is based on a maximum of the inputs. For example, with a 2×2 filter, the output is based on a maximum value from the four input values. In other embodiments, the pooling layer is an average pooling layer or L2-norm pooling layer. Various other pooling schemes are possible.

The intermediate layers can include a Rectified Linear Units (RELU) layer 1726. The output of the pooling layer 1724 can be input to the RELU layer 1726. In embodiments, the RELU layer implements an activation function such as $f(x)=\max(0,x)$, thus providing an activation with a threshold at zero. In some embodiments, the RELU layer 1726 is a leaky RELU layer. In this case, instead of the activation function providing zero when x<0, a small negative slope is used, resulting in an activation function such as $f(x)=1(x<0)(ax)+1(x>=0)(x)$. This can reduce the risk of "dying RELU"
syndrome, where portions of the network can be "dead" with nodes/neurons that do not activate across the training dataset. The image analysis can comprise training a multilayered analysis engine using the plurality of images, wherein the multilayered analysis engine can include multiple layers that include one or more convolutional layers 1722 and one or more hidden layers, and wherein the multilayered analysis engine can be used for emotional analysis.

The example 1700 includes a fully connected layer 1730. The fully connected layer 1730 processes each pixel/data point from the output of the collection of intermediate layers 1720. The fully connected layer 1730 takes all neurons in the previous layer and connects them to every single neuron it has. The output of the fully connected layer 1730 provides input to a classification layer 1740. The output of the classification layer 1740 provides a facial expression and/or cognitive state as its output. Thus, a multilayered analysis engine such as the one depicted in FIG. 17 processes image data using weights, models the way the human visual cortex performs object recognition and learning, and is effective for analysis of image data to infer facial expressions and cognitive states.

Machine learning for generating parameters, analyzing data such as facial data and audio data, and so on, can be based on a variety of computational techniques. Generally, machine learning can be used for constructing algorithms and models. The constructed algorithms, when executed, can be used to make a range of predictions relating to data. The predictions can include whether an object in an image is a face, a box, or a puppy, whether a voice is female, male, or robotic, whether a message is legitimate email or a "spam" message, and so on. The data can include unstructured data and can be of large quantity. The algorithms that can be generated by machine learning techniques are particularly useful to data analysis because the instructions that comprise the data analysis technique do not need to be static. Instead, the machine learning algorithm or model, generated by the machine learning technique, can adapt. Adaptation of the learning algorithm can be based on a range of criteria such as success rate, failure rate, and so on. A successful algorithm is one that can adapt—or learn—as more data is presented to the algorithm. Initially, an algorithm can be "trained" by presenting it with a set of known data (supervised learning). Another approach, called unsupervised learning, can be used to identify trends and patterns within data. Unsupervised learning is not trained using known data prior to data analysis.

Reinforced learning is an approach to machine learning that is inspired by behaviorist psychology. The underlying premise of reinforced learning (also called reinforcement learning) is that software agents can take actions in an environment. The actions that are taken by the agents should maximize a goal such as a "cumulative reward". A software agent is a computer program that acts on behalf of a user or other program. The software agent is implied to have the authority to act on behalf of the user or program. The actions taken are decided by action selection to determine what to do next. In machine learning, the environment in which the agents act can be formulated as a Markov decision process (MDP). The MDPs provide a mathematical framework for modeling of decision making in environments where the outcomes can be partly random (stochastic) and partly under the control of the decision maker. Dynamic programming techniques can be used for reinforced learning algorithms. Reinforced learning is different from supervised learning in that correct input/output pairs are not presented, and suboptimal actions are not explicitly corrected. Rather, on-line or computational performance is the focus. On-line performance includes finding a balance between exploration of new (uncharted) territory or spaces, and exploitation of current knowledge. That is, there is a tradeoff between exploration and exploitation.

Machine learning based on reinforced learning adjusts or learns based on learning an action, a combination of actions, and so on. An outcome results from taking an action. Thus, the learning model, algorithm, etc., learns from the outcomes that result from taking the action or combination of actions. The reinforced learning can include identifying positive outcomes, where the positive outcomes are used to adjust the learning models, algorithms, and so on. A positive outcome can be dependent on a context. When the outcome is based on a mood, emotional state, mental state, cognitive state, etc., of an individual, then a positive mood, emotion, mental state, or cognitive state can be used to adjust the model and algorithm. Positive outcomes can include a person being more engaged, where engagement is based on affect, the person spending more time playing an online game or navigating a webpage, the person converting by buying a product or service, and so on. The reinforced learning can be based on exploring a solution space and adapting the model, algorithm, etc., based on outcomes of the exploration. When positive outcomes are encountered, the positive outcomes can be reinforced by changing the weighting values within the model, algorithm, etc. Positive outcomes may result in increasing the weighting values. Negative outcomes can also be considered, where weighting values may be reduced or otherwise adjusted.

Figure 18:
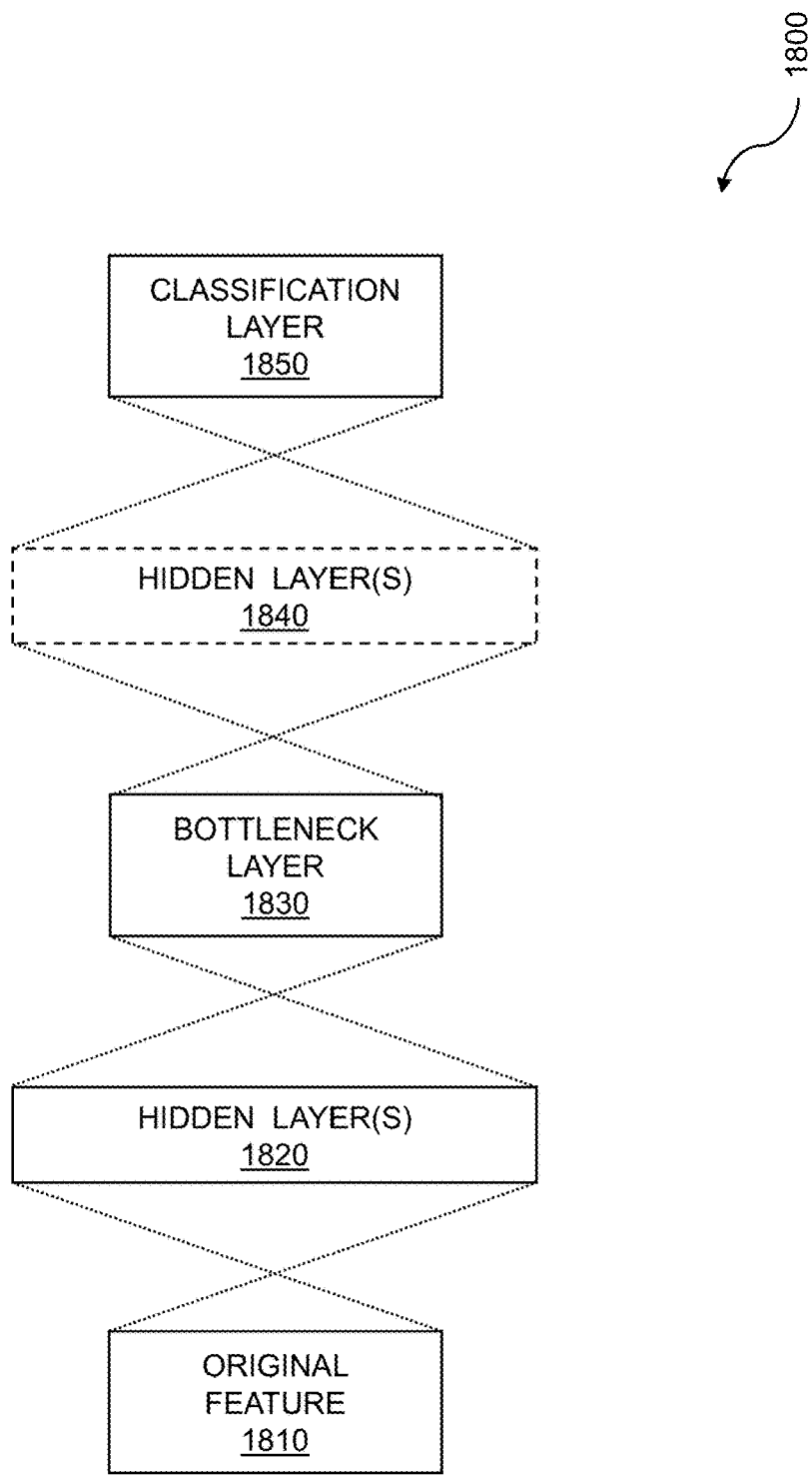
FIG. 18 illustrates a bottleneck layer within a deep learning environment.

FIG. 18 illustrates a bottleneck layer within a deep learning environment. A bottleneck layer can be one of a plurality of layers in a deep neural network. The bottleneck layer can be used for image analysis for a two-sided data hub. A deep neural network can apply classifiers such as image classifiers, audio classifiers, and so on. The classifiers can be learned by analyzing cognitive state data which can include facial data, speech data, etc. Data reception is enabled by an individual and a content provider. Cognitive state data including facial data, audio data, etc., is collected on the individual. The cognitive state data is analyzed and the analysis is provided to the individual. The cognitive state data is evaluated and the evaluation is provided to the content provider. A mood dashboard is displayed to the individual based on the analyzing.

Layers of a deep neural network can include a bottleneck layer 1800. A bottleneck layer can be used for a variety of applications such as facial recognition, voice recognition, emotional state recognition, and so on. The deep neural network in which the bottleneck layer is located can include a plurality of layers. The plurality of layers can include an original feature layer 1810. A feature such as an image feature can include points, edges, objects, boundaries between and among regions, properties, and so on. The deep neural network can include one or more hidden layers 1820. The one or more hidden layers can include nodes, where the nodes can include nonlinear activation functions and other techniques. The bottleneck layer can be a layer that learns translation vectors to transform a neutral face to an emotional or expressive face. In some embodiments, the translation vectors can transform a neutral sounding voice to an emotional or expressive voice. Specifically, activations of the bottleneck layer determine how the transformation occurs. A single bottleneck layer can be trained to transform a neutral face or voice to a different emotional face or voice. In some cases, an individual bottleneck layer can be trained for a transformation pair. At runtime, once the user's emotion has been identified and an appropriate response to it can be determined (mirrored or complementary), the trained bottleneck layer can be used to perform the needed transformation.

The deep neural network can include a bottleneck layer 1830. The bottleneck layer can include a fewer number of nodes than the one or more preceding hidden layers. The bottleneck layer can create a constriction in the deep neural network or other network. The bottleneck layer can force information that is pertinent to a classification, for example, into a low dimensional representation. The bottleneck features can be extracted using an unsupervised technique. In other embodiments, the bottleneck features can be extracted in a supervised manner. The supervised technique can include training the deep neural network with a known dataset. The features can be extracted from an autoencoder such as a variational autoencoder, a generative autoencoder, and so on. The deep neural network can include hidden layers 1840. The number of the hidden layers can include zero hidden layers, one hidden layer, a plurality of hidden layers, and so on. The hidden layers following the bottleneck layer can include more nodes than the bottleneck layer. The deep neural network can include a classification layer 1850. The classification layer can be used to identify the points, edges, objects, boundaries, and so on, described above. The classification layer can be used to identify cognitive states, mental states, emotional states, moods, and the like. The output of the final classification layer can be indicative of the emotional states of faces within the images, where the images can be processed using the deep neural network.

Figure 19:
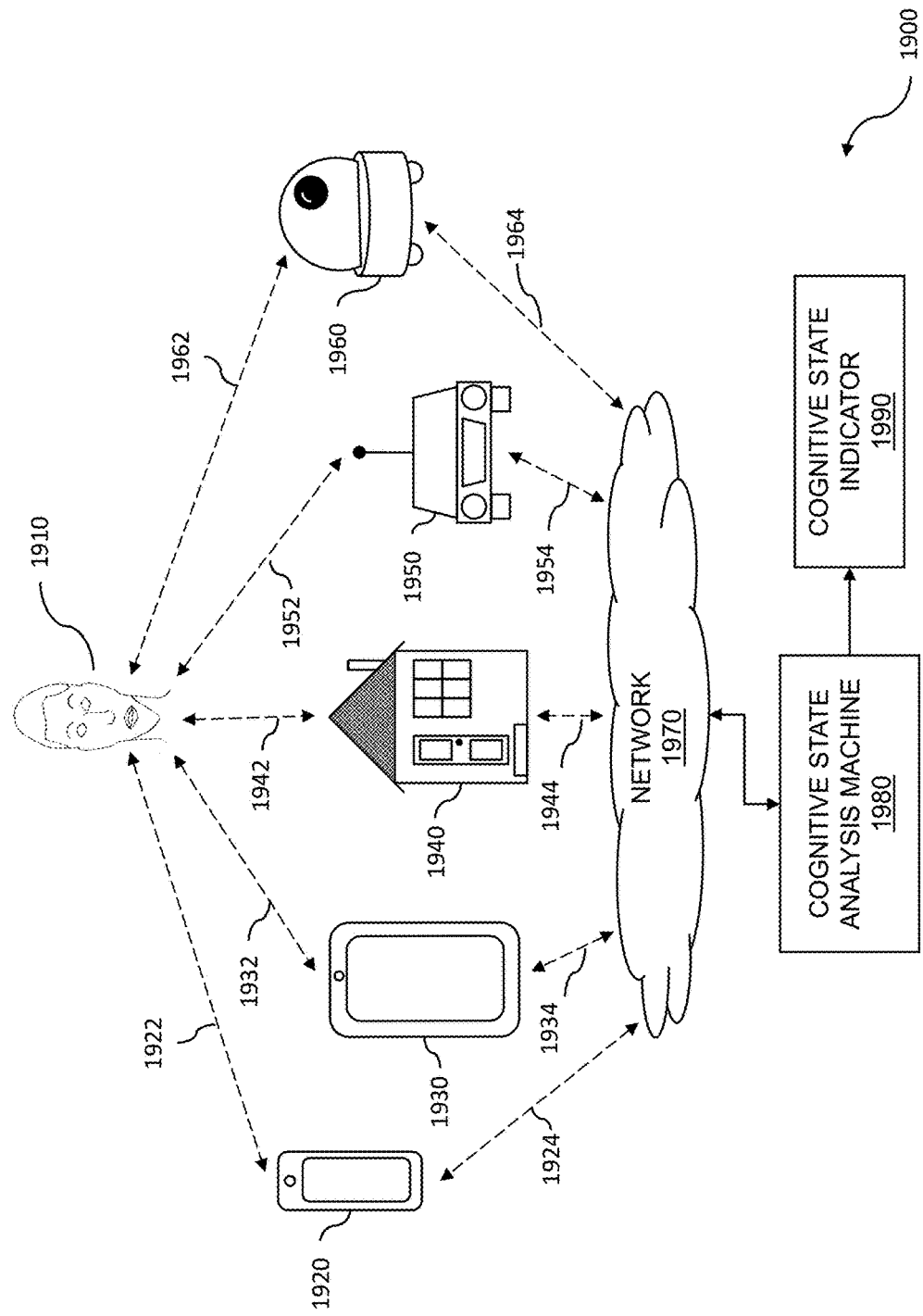
FIG. 19 shows data collection including devices and locations.

FIG. 19 shows data collection including devices and locations 1900. Cognitive state data, facial data, or audio data can be collected for image analysis for a two-sided data hub. Data is enabled reception by both an individual and a content provider. Cognitive state data including facial data is collected on the individual. The cognitive state data is analyzed and the results are provided to the individual, and the cognitive state data is evaluated and the results are provided to the content provider.

Multiple mobile devices, vehicles, and locations, can be used separately or in combination to collect video data or audio data on a user 1910. While one person is shown, the video data can be collected on multiple people. A user 1910 can be observed as she or he is performing a task, experiencing an event, viewing a media presentation, and so on. The user 1910 can be shown one or more media presentations, political presentations, social media, or another form of displayed media. The one or more media presentations can be shown to a plurality of people. The media presentations can be displayed on an electronic display coupled to a client device. The data collected on the user 1910 or on a plurality of users can be in the form of one or more videos, video frames, or still images, audio streams or audio clips, etc. The plurality of videos can be of people who are experiencing different situations. Some example situations can include the user or plurality of users being exposed to TV programs, movies, video clips, social media, social sharing, and other such media. The situations could also include exposure to media such as advertisements, political messages, news programs, and so on.

As noted before, video data can be collected on one or more users in substantially identical or different situations and viewing either a single media presentation or a plurality of presentations. The data collected on the user 1910 can be analyzed and viewed for a variety of purposes including expression analysis, mental state analysis, cognitive state analysis, and so on. The electronic display can be on a smartphone 1920 as shown, a tablet computer 1930, a personal digital assistant, a television, a mobile monitor, or any other type of electronic device. In one embodiment, expression data is collected on a mobile device such as a cell phone or smartphone 1920, a tablet computer 1930, a laptop computer, or a watch. Thus, the multiple sources can include at least one mobile device, such as a smartphone 1920 or a tablet computer 1930, or a wearable device such as a watch or glasses (not shown). A mobile device can include a front-side camera and/or a back-side camera that can be used to collect expression data. Sources of expression data can include a webcam, a phone camera, a tablet camera, a wearable camera, and a mobile camera. A wearable camera can comprise various camera devices, such as a watch camera. In addition to using client devices for data collection from the user 1910, data can be collected in a house 1940 using a web camera or the like; in a vehicle 1950 using a web camera, client device, etc.; by a social robot 1960; and so on.

As the user 1910 is monitored, the user 1910 might move due to the nature of the task, boredom, discomfort, distractions, or for another reason. As the user moves, the camera with a view of the user's face can be changed. Thus, as an example, if the user 1910 is looking in a first direction, the line of sight 1922 from the smartphone 1920 is able to observe the user's face, but if the user is looking in a second direction, the line of sight 1932 from the tablet computer 1930 is able to observe the user's face. Furthermore, in other embodiments, if the user is looking in a third direction, the line of sight 1942 from a camera in the house 1940 is able to observe the user's face, and if the user is looking in a fourth direction, the line of sight 1952 from the camera in the vehicle 1950 is able to observe the user's face. If the user is looking in a fifth direction, the line of sight 1962 from the social robot 1960 is able to observe the user's face. If the user is looking in a sixth direction, a line of sight from a wearable watch-type device, with a camera included on the device, is able to observe the user's face. In other embodiments, the wearable device is another device, such as an earpiece with a camera, a helmet or hat with a camera, a clip-on camera attached to clothing, or any other type of wearable device with a camera or other sensor for collecting expression data. The user 1910 can also use a wearable device including a camera for gathering contextual information and/or collecting expression data on other users. Because the user 1910 can move her or his head, the facial data can be collected intermittently when she or he is looking in a direction of a camera. In some cases, multiple people can be included in the view from one or more cameras, and some embodiments include filtering out faces of one or more other people to determine whether the user 1910 is looking toward a camera. All or some of the expression data can be continuously or sporadically available from the various devices and other devices.

The captured video data can include cognitive content, such as facial expressions, etc., and can be transferred over a network 1970. The network can include the Internet or other computer network. The smartphone 1920 can share video using a link 1924, the tablet computer 1930 using a link 1934, the house 1940 using a link 1944, the vehicle 1950 using a link 1954, and the social robot 1960 using a link 1964. The links 1924, 1934, 1944, 1954, and 1964 can be wired, wireless, and hybrid links. The captured video data, including facial expressions, can be analyzed on a cognitive state analysis engine 1980, on a computing device such as the video capture device, or on another separate device. The analysis could take place on one of the mobile devices discussed above, on a local server, on a remote server, and so on. In embodiments, some of the analysis takes place on the mobile device, while other analysis takes place on a server device. The analysis of the video data can include the use of a classifier. The video data can be captured using one of the mobile devices discussed above and sent to a server or another computing device for analysis. However, the captured video data including expressions can also be analyzed on the device which performed the capturing. The analysis can be performed on a mobile device where the videos were obtained with the mobile device and wherein the mobile device includes one or more of a laptop computer, a tablet, a PDA, a smartphone, a wearable device, and so on. In another embodiment, the analyzing comprises using a classifier on a server or another computing device other than the capture device. The analysis data from the cognitive state analysis engine can be processed by a cognitive state indicator 1990. The cognitive state indicator 1990 can indicate cognitive states, mental states, moods, emotions, etc. In embodiments, the cognitive content can include detection of one or more of drowsiness, fatigue, distraction, sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, depression, envy, sympathy, embarrassment, poignancy, or mirth.

Figure 20:
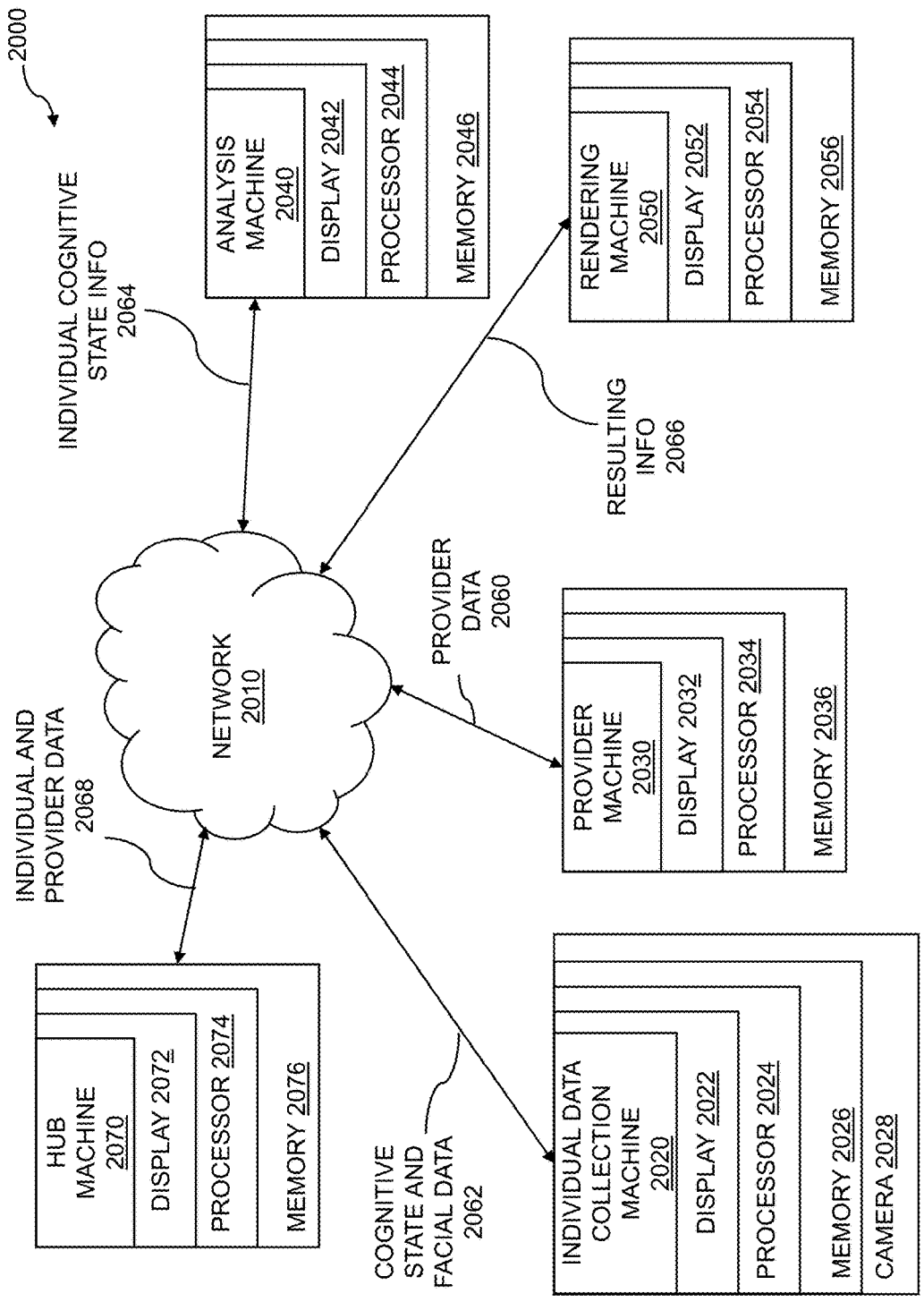
FIG. 20 is a diagram of a system for image analysis for two-sided data hub.

FIG. 20 is a diagram of a system 2000 for image analysis for two-sided data hub. Data reception is enabled on a first computing device by both an individual and a content provider. Cognitive state data including facial data on the individual is collected on a second computing device. The cognitive state data is analyzed on a third computing device and the results are provided to the individual. The cognitive state data is evaluated and the results are provided to the content provider.

The network 2010, Internet, intranet, or another wired, wireless, or hybrid computer network can be used for communicating among the various machines that comprise a system for image analysis. An individual data collection machine 2020 has a memory 2026 which stores instructions and one or more processors 2024 attached to the memory 2026, wherein the one or more processors 2024 can execute instructions. The individual data collection machine 2020 can also have a network connection to carry cognitive state and facial data 2062, and a display 2022 that can present various renderings to a user. The individual data collection machine 2020 can collect cognitive state data from a plurality of people as they interact with a rendering. The individual data collection machine 2020 can include a camera 2028. The camera 2028 can include a webcam, a video camera, a still camera, a thermal imager, a CCD device, a smartphone camera, a three-dimensional camera, a depth camera, a light field camera, multiple webcams used to show different views of a person from different angles, or any other type of image capture technique that can allow captured data to be used in an electronic system. In some embodiments, there are multiple individual data collection machines 2020 that each collect cognitive state data including facial data from one person or a plurality of people as they interact with a rendering. The individual data collection machine 2020 can communicate with an analysis server 2040 and other machines over the network 2010, some other computer network, or by another method suitable for communication between two computers. In some embodiments, the server 2040 functionality is embodied in the individual data collection machine 2020.

A provider machine 2030 can have a network connection for provider data 2060, a memory 2036 which stores instructions, and one or more processors 2034 attached to the memory 2036, wherein the one or more processors 2034 can execute instructions. The provider machine 2030 can give provider data to one or more individuals interacting with one or more individual data collection machines 2020. The provider machine 2030 can provide images, videos, webpages, web content, etc. In some embodiments, the provider machine 2030 renders content on a display 2032. The display 2032 can be any electronic display, including but not limited to, a computer display, a laptop screen, a tablet computer screen, a smartphone display, a mobile device display, a remote with a display, a television, a projector, or the like.

An analysis machine 2040 can have a network connection for individual cognitive state information 2064, a memory 2046 which stores instructions, and one or more processors 2044 attached to the memory 2046, wherein the one or more processors 2044 can execute instructions. The analysis machine 2040 can receive individual cognitive state information 2064 collected from one or more people as they interact with a rendering from the individual data collection machine 2020 and can analyze, aggregate, etc., the cognitive state information on the plurality of people who interact with the rendering. In some embodiments, the analysis machine 2040 also allows a user to view and evaluate the individual cognitive state information that is associated with the rendering on a display 2042.

A rendering machine 2050 can have a memory 2056 which stores instructions, and one or more processors 2054 attached to the memory 2056, wherein the one or more processors 2054 can execute instructions. The rendering machine 2050 can use a network connection 2066, or another computer communication technique, to send and receive resulting information 2066. The rendering machine 2050 can receive aggregated cognitive state and facial information 2062, provider data 2060, individual cognitive state information 2064, individual and provider data 2068, etc. The data and information can be rendered on a display 2052.

A hub machine 2070 can have a network connection for individual and provider data 2068, a memory 2076 which stores instructions, and one or more processors 2074 attached to the memory 2076, where the one or more processors 2074 can execute instructions. The hub machine 2070 can receive individual and provider data collected from one or more individual data collection machines 2020 and provided by one or more provider machines 2030. In some embodiments, the hub machine 2070 can render content and data on a display 2072. The content and data can include provider data 2060 from a content provider machine 2030, cognitive state and facial data 2062 from an individual data collection machine 2020, individual cognitive state information 2064 from an analysis server 2040, resulting information 2066 from a rendering machine 2050, and so on.

The system 2000 can include a computer program product embodied in a non-transitory computer readable medium for image analysis, the computer program product comprising code which causes one or more processors to perform operations of: enabling, on a first computing device, data reception by an individual and a content provider; collecting, on a second computing device, cognitive state data including facial data on the individual; analyzing, on a third computing device, the cognitive state data for providing analysis of the cognitive state data to the individual; and evaluating the cognitive state data for providing evaluation of the cognitive state data to the content provider.

Each of the above methods may be executed on one or more processors on one or more computer systems. Embodiments may include various forms of distributed computing, client/server computing, and cloud-based computing. Further, it will be understood that for each flow chart in this disclosure, the depicted steps or boxes are provided for purposes of illustration and explanation only. The steps may be modified, omitted, or re-ordered and other steps may be added without departing from the scope of this disclosure. Further, each step may contain one or more sub-steps. While the foregoing drawings and description set forth functional aspects of the disclosed systems, no particular arrangement of software and/or hardware for implementing these functional aspects should be inferred from these descriptions unless explicitly stated or otherwise clear from the context. All such arrangements of software and/or hardware are intended to fall within the scope of this disclosure.

The block diagrams and flowchart illustrations depict methods, apparatus, systems, and computer program products. Each element of the block diagrams and flowchart illustrations, as well as each respective combination of elements in the block diagrams and flowchart illustrations, illustrates a function, step or group of steps of the methods, apparatus, systems, computer program products and/or computer-implemented methods. Any and all such functions may be implemented by computer program instructions, by special-purpose hardware-based computer systems, by combinations of special purpose hardware and computer instructions, by combinations of general purpose hardware and computer instructions, and so on. Any and all of which may be generally referred to herein as a "circuit," "module," or "system."

A programmable apparatus which executes any of the above-mentioned computer program products or computer implemented methods may include one or more microprocessors, microcontrollers, embedded microcontrollers, programmable digital signal processors, programmable devices, programmable gate arrays, programmable array logic, memory devices, application specific integrated circuits, or the like. Each may be suitably employed or configured to process computer program instructions, execute computer logic, store computer data, and so on.

It will be understood that a computer may include a computer program product from a computer-readable storage medium and that this medium may be internal or external, removable and replaceable, or fixed. In addition, a computer may include a Basic Input/Output System (BIOS), firmware, an operating system, a database, or the like that may include, interface with, or support the software and hardware described herein.

Embodiments of the present invention are not limited to applications involving conventional computer programs or programmable apparatus that run them. It is contemplated, for example, that embodiments of the presently claimed invention could include an optical computer, quantum computer, analog computer, or the like. A computer program may be loaded onto a computer to produce a particular machine that may perform any and all of the depicted functions. This particular machine provides a means for carrying out any and all of the depicted functions.

Any combination of one or more computer readable media may be utilized. The computer readable medium may be a non-transitory computer readable medium for storage. A computer readable storage medium may be electronic, magnetic, optical, electromagnetic, infrared, semiconductor, or any suitable combination of the foregoing. Further computer readable storage medium examples may include an electrical connection having one or more wires, a portable computer diskette, a hard disk, a random-access memory (RAM), a read-only memory (ROM), an erasable programmable read-only memory (EPROM, Flash, MRAM, FeRAM, or phase change memory), an optical fiber, a portable compact disc read-only memory (CD-ROM), an optical storage device, a magnetic storage device, or any suitable combination of the foregoing. In the context of this document, a computer readable storage medium may be any tangible medium that can contain or store a program for use by or in connection with an instruction execution system, apparatus, or device.

It will be appreciated that computer program instructions may include computer executable code. A variety of languages for expressing computer program instructions may include without limitation C, C++, Java, JavaScript™, ActionScript™, assembly language, Lisp, Perl, Tcl, Python, Ruby, hardware description languages, database programming languages, functional programming languages, imperative programming languages, and so on. In embodiments, computer program instructions may be stored, compiled, or interpreted to run on a computer, a programmable data processing apparatus, a heterogeneous combination of processors or processor architectures, and so on. Without limitation, embodiments of the present invention may take the form of web-based computer software, which includes client/server software, software-as-a-service, peer-to-peer software, or the like.

In embodiments, a computer may enable execution of computer program instructions including multiple programs or threads. The multiple programs or threads may be processed more or less simultaneously to enhance utilization of the processor and to facilitate substantially simultaneous functions. By way of implementation, any and all methods, program codes, program instructions, and the like described herein may be implemented in one or more thread. Each thread may spawn other threads, which may themselves have priorities associated with them. In some embodiments, a computer may process these threads based on priority or other order.

Unless explicitly stated or otherwise clear from the context, the verbs "execute" and "process" may be used interchangeably to indicate execute, process, interpret, compile, assemble, link, load, or a combination of the foregoing. Therefore, embodiments that execute or process computer program instructions, computer-executable code, or the like may act upon the instructions or code in any and all of the ways described. Further, the method steps shown are intended to include any suitable method of causing one or more parties or entities to perform the steps. The parties performing a step, or portion of a step, need not be located within a particular geographic location or country boundary. For instance, if an entity located within the United States causes a method step, or portion thereof, to be performed outside of the United States then the method is considered to be performed in the United States by virtue of the entity causing the step to be performed.

While the invention has been disclosed in connection with preferred embodiments shown and described in detail, various modifications and improvements thereon will become apparent to those skilled in the art. Accordingly, the spirit and scope of the present invention is not to be limited by the foregoing examples, but is to be understood in the broadest sense allowable by law.

What is claimed is:

1. A computer-implemented method for image analysis comprising:
   collecting cognitive state data including facial data on an individual in a first vehicle;
   analyzing the cognitive state data using a neural network trained to identify facial expressions and cognitive states;
   generating a cognitive state profile for the individual in the first vehicle based on the analyzing;
   transmitting the cognitive state profile to a two-sided data hub; and
   providing vehicular manipulation of a second vehicle from the two-sided data hub.

2. The method of claim 1 wherein the collecting cognitive state data, including facial data on the individual, is accomplished using a webcam.

3. The method of claim 2 wherein the collecting cognitive state data further includes capturing physiological data.

4. The method of claim 1 wherein the collecting of cognitive state data is accomplished within the first vehicle.

5. The method of claim 1 wherein the analyzing further comprises comparing the cognitive state data with collected cognitive state data from other individuals.

6. The method of claim 5 wherein the comparing provides quantified self-information on cognitive states for the individual.

7. The method of claim 1 wherein the analyzing includes using an image classifier from a plurality of image classifiers to detect emotional content within the facial data for the individual.

8. The method of claim 1 wherein the analyzing the cognitive state data is used to enable the individual to track cognitive health.

9. The method of claim 1 further comprising augmenting the analyzing using audio data from the individual.

10. The method of claim 9 wherein the audio data includes voice data from the individual.

11. The method of claim 1 wherein the cognitive state data is indicative of drowsiness, fatigue, distraction, impairment, sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, depression, envy, sympathy, embarrassment, poignancy, or mirth.

12. A computer program product embodied in a non-transitory computer readable medium for image analysis, the computer program product comprising code which causes one or more processors to perform operations of:
    collecting cognitive state data including facial data on an individual in a first vehicle;
    analyzing the cognitive state data using a neural network trained to identify facial expressions and cognitive states;
    generating a cognitive state profile for the individual in the first vehicle based on the analyzing;
    transmitting the cognitive state profile to a two-sided data hub; and
    providing vehicular manipulation of a second vehicle from the two-sided data hub.

13. A computer system for image analysis comprising:
    a memory which stores instructions;
    one or more processors attached to the memory wherein the one or more processors, when executing the instructions which are stored, are configured to:
       collect cognitive state data including facial data on an individual in a first vehicle;

analyze the cognitive state data using a neural network trained to identify facial expressions and cognitive states;

generate a cognitive state profile for the individual in the first vehicle based on the analyzing;

transmit the cognitive state profile to a two-sided data hub; and provide vehicular manipulation of a second vehicle from the two-sided data hub.

14. The method of claim 1, further comprising providing driving directions to the individual; identifying a change in a cognitive state of the individual; modifying the driving directions as a function of the change; and providing the modified driving directions to the individual.

15. The method of claim 1, further comprising:

collecting further cognitive state data including facial data on an individual in the second vehicle;

analyzing the further cognitive state data using a neural network trained to identify facial expressions and cognitive states;

generating a cognitive state profile for the individual in the second vehicle based on the analyzing the further cognitive state data;

transmitting the cognitive state profile for the individual in the second vehicle to the two-sided data hub; and providing vehicular manipulation of the first or second vehicle from the two-sided data hub.

16. The method of claim 1 wherein the vehicular manipulation includes adjusting an interior temperature.

17. The method of claim 1 wherein the vehicular manipulation includes brake activation.

* * * * *